US010087483B2

(12) United States Patent
Solstad et al.

(10) Patent No.: US 10,087,483 B2
(45) Date of Patent: Oct. 2, 2018

(54) THERMOLABILE EXONUCLEASES

(71) Applicants: ArcticZymes AS, Tromsø (NO); Universitetet I Tromsø—Norges Arktiske Universitet, Tromsø (NO)

(72) Inventors: Terese Solstad, Kvaløysletta (NO); Elisabeth Lill Andreassen, Tromsø (NO); Marit Sjo Lorentzen, Krokelvdalen (NO); Olav Lanes, Tromsø (NO); Morten Elde, Tromsø (NO); Atle Noralf Larsen, Kvaløysletta (NO); Yvonne Piotrowski, Tomasjord (NO); Nils Peder Willassen, Tomasjord (NO)

(73) Assignees: ARCTICZYMES AS, Tromsø (NO); UNIVERSITETET I TROMSØ—NORGES ARKTISKE UNIVERSITET, Tromsø (NO)

( * ) Notice: Subject to any disclaimer, the term of this patent is extended or adjusted under 35 U.S.C. 154(b) by 0 days.

(21) Appl. No.: 15/504,507

(22) PCT Filed: Aug. 19, 2015

(86) PCT No.: PCT/EP2015/001703
§ 371 (c)(1),
(2) Date: Feb. 16, 2017

(87) PCT Pub. No.: WO2016/026574
PCT Pub. Date: Feb. 25, 2016

(65) Prior Publication Data
US 2017/0233800 A1    Aug. 17, 2017

(30) Foreign Application Priority Data

Aug. 19, 2014   (GB) .................................. 1414745.8

(51) Int. Cl.
| | |
|---|---|
| *C12N 9/22* | (2006.01) |
| *C12Q 1/686* | (2018.01) |
| *C12Q 1/6844* | (2018.01) |
| *C12Q 1/6848* | (2018.01) |
| *C12Q 1/34* | (2006.01) |
| *G01N 1/30* | (2006.01) |

(52) U.S. Cl.
CPC ............. *C12Q 1/6848* (2013.01); *C12N 9/22* (2013.01); *C12Q 1/34* (2013.01); *C12Y 301/11001* (2013.01); *G01N 1/30* (2013.01); *C12Q 2521/325* (2013.01); *G01N 2333/922* (2013.01)

(58) Field of Classification Search
CPC ......... C12Q 1/686; C12Q 1/6844; C12N 9/22
See application file for complete search history.

(56) References Cited

U.S. PATENT DOCUMENTS

| | | | |
|---|---|---|---|
| 5,741,676 A | 4/1998 | Fuller | |
| 5,756,285 A | 5/1998 | Fuller | |
| 5,922,539 A * | 7/1999 | Modrich | ............ C12N 15/1003 |
| | | | 435/183 |
| 5,985,619 A | 11/1999 | Sutherland et al. | |
| 6,379,940 B2 | 4/2002 | Moffett et al. | |
| 6,387,634 B2 | 5/2002 | Moffett et al. | |
| 7,378,262 B2 | 5/2008 | Sobek et al. | |
| 7,449,304 B2 | 11/2008 | Sudor | |
| 8,211,673 B2 | 7/2012 | Lee | |
| 2001/0051362 A1 | 12/2001 | Moffett et al. | |
| 2003/0087278 A1 | 5/2003 | Sayers et al. | |
| 2004/0096870 A1 | 5/2004 | Slepnev | |
| 2007/0122811 A1 | 5/2007 | Buzby | |
| 2008/0044851 A1 | 2/2008 | Jendrisak et al. | |
| 2009/0047705 A1 | 2/2009 | Awazu et al. | |
| 2014/0030721 A1 | 1/2014 | Fredriksson et al. | |

FOREIGN PATENT DOCUMENTS

| | | |
|---|---|---|
| CA | 2137728 C | 7/1998 |
| CN | 1665938 A | 9/2005 |
| EP | 0585660 A2 | 3/1994 |
| EP | 2670860 B1 | 8/2017 |

(Continued)

OTHER PUBLICATIONS

Copeland et al., Uniprot database, Accession No. A8H5H0, 2007.*
Database Uniprot [Online] Mar. 3, 2009, "Exodeoxyribonuclease I" Database accession No. B8CR82 XP-002749256 (1 page).
Database Uniprot [Online] Feb. 22, 2012, "Exodeoxyribonuclease I" Database accession No. G9E9Z0 XP-002749257 (1 page).
Database Uniprot [Online] Nov. 25, 2008, "Exodeoxyribonuclease I" Database accession No. B6EMI0 XP-002749258 (1 page).
Database REFSEQ [Online] NCBI: "Exonuclease I [*Psychromonas* sp. SP041]" Database accession No. WP_025564239 XP-002749259 (2 page).

(Continued)

*Primary Examiner* — Maryam Monshipouri
(74) *Attorney, Agent, or Firm* — Rothwell, Figg, Ernst & Manbeck, P.C.

(57) ABSTRACT

The invention provides an exonuclease or an enzymatically active fragment thereof, said exonuclease having the amino acid sequence of SEQ ID No. 1 or an amino acid sequence which is at least about 50% identical thereto, wherein said exonuclease or enzymatically active fragment thereof (i) is substantially irreversibly inactivated by heating at a temperature of about 55° C. for 10 minutes in a buffer consisting of 10 mM Tris-HCl, pH 8.5 at 25° C., 50 mM KCl and 5 mM $MgCl_2$; (ii) is substantially specific for single stranded DNA; and (iii) has a 3'-5' exonuclease activity. The invention further provides a method of removing single stranded DNA from a sample, a method of nucleic acid amplification, a method of reverse transcription and a method of nucleic acid sequence analysis in which the exonuclease or enzymatically active fragment thereof is used. The invention still further provides nucleic acids encoding said exonuclease or an enzymatically active fragment thereof and kits or compositions comprising the same.

14 Claims, 32 Drawing Sheets

Specification includes a Sequence Listing.

(56) References Cited

FOREIGN PATENT DOCUMENTS

| JP | 2003199592 | A | 7/2003 |
|----|------------|---|--------|
| JP | 2004057055 | A | 2/2004 |
| WO | 0109343 | A1 | 2/2001 |
| WO | 2004/003136 | A2 | 1/2004 |
| WO | 2004003136 | A2 | 1/2004 |
| WO | 2004061135 | A1 | 7/2004 |
| WO | 2009077411 | A1 | 6/2009 |
| WO | 2009154303 | A2 | 12/2009 |
| WO | 2010045326 | A1 | 4/2010 |
| WO | 2010086603 | A1 | 8/2010 |
| WO | 2011010094 | A1 | 1/2011 |
| WO | 2013079924 | A2 | 6/2013 |
| WO | 2013121228 | A1 | 8/2013 |

OTHER PUBLICATIONS

Database Uniprot [Online] Jul. 24, 2007, "Exodeoxyribonuclease I" Database accession No. A6FJ54 XP-002749260 (1 page).
Database Uniprot [Online] May 27, 2015, "Exodeoxyribonuclease I" Database accession No. A0A0D6EEQ6 XP-002749261 (1 page).
Database Uniprot [Online] Nov. 26, 2014, "Exodeoxyribonuclease I" Database accession No. A0A090IMI7 XP-002749262 (1 page).
Database Uniprot [Online] Nov. 26, 2014, "Exodeoxyribonuclease I" Database accession No. A0A090IE98 XP-002749263 (1 page).
Gibson, Daniel et al. "Enzymatic assembly of DNA molecules up to several hundred kilobases." Nature Methods. May 2009, pp. 343-345, vol. 6, No. 5.
International Search Report and Written Opinion issued in PCT/EP2015/001703 dated Nov. 27, 2015 (14 pages).
Ruby, E. G., et al., "Complete genome sequence of Vibrio fischeri: A symbiotic bacterium with pathogenic congeners," PNAS, 102(8), Feb. 22, 2005, 3004-3009.
Heidelberg, J. F., et al., "Genome sequence of the dissimilatory metal ion-reducing bacterium Shewanella oneidensis," Nature Biotechnology, 20, Nov. 2002, 1118-1123.
Medigue, C., et al., "Coping with cold: The genome of the versatile marine Antarctica bacterium Pseudoalteromonas haloplanktis TAC125," Genome Research, 15, 2005, 1325-1335.
Methe, B. A., et al., "The psychrophilic lifestyle as revealed by the genome sequence of Colwellia psychrerythraea 34H through genomic and protemoic analyses," PNAS, 102(31), Aug. 2, 2005, 10913-10918.
Yang, W., "Nucleases: Diversity of structure, function and mechanism," Quarterly Review of Biophysics, 44, 2011, 1-93.
Bryksin, A. V., and Matsumura, I., "Overlap extension PCR cloning: A simple and reliable way to create recombinant plasmids," Biotechniques, 48(6), Jun. 2010, 463-465.
Korada, S. K. C., et al., "Crystal structures of *Escherichia coli* exonuclease I in complex with single-stranded DNA provide insights into the mechanism of process digestion," Nucleic Acids Research, 41(11), 2013, 5887-5897.
Prasher, D. C., et al., "Amplification and purification of exonuclease I from *Escherichia coli* K12," The Journal of Biological Chemistry, 258(10), 1983, 6340-6343.
Somoskeoy, S., et al., "Purification and characterization of a 5' to 3' exoribinuclease from rabbit reticulocytes that degrades capped and uncapped RNAs," Eur. J. Biochem., 237, 1996, 171-179.
Dynlacht, J. R., et al., "Identification of Mre11 as a target for heat radiosensitization," Radiat Res., 176(3), Sep. 2011, 323-332.
Exodeoxyribonuclease I [Shewanella piezotolerans], NCBI Reference Sequence: WP_020913106.1, Jul. 25, 2013, 1 page.
Exonuclease I [*Halomonas* sp. 19A_GOM-1509m], NCBI Reference Sequence: WP_027957731.1, Jun. 12, 2014, 1 page.
Exonuclease I [Aliivibrio logei], NCBI Reference Sequence: WP_017021278.1, Jun. 27, 2013, 1 page.
Exonuclease I [*Psychromonas* sp. SP041], NCBI Reference Sequence: WP_025564239.1, Jun. 5, 2014, 1 page.
Exonuclease I [*Moritella* sp. PE36], NCBI Reference Sequence: WP_006034409.1, May 25, 2013, 1 page.
Chinese Office Action issued in Application No. 201580043582.4 dated Dec. 15, 2017, 24 pages.
Genbank, ID: CP000472.1, Shewanella piezotolerans WP3, complete genome, Jan. 31, 2014, 962 pages.
Genbank, ID: CP007757.1, Halomonas companiensis strain LS21, complete genome, published May 30, 2014, 254 pages.
Genbank, ID: FM178379.1, Aliivibrio salmonicida LFI1238 chromosome 1, published Sep. 23, 2011, 622 pages.
Genbank, ID: NZ CBRF010000144.1, *Psychromonas* sp. SP041, whole genome shotgun sequence, published Jun. 25, 2014, 6 pages.
Genbank, ID: NZ ABCQ01000081.1, *Moritella* sp. PE361099400000749, whole genome shotgun sequence, published May 8, 2013, 6 pages.

\* cited by examiner

Figure 1: Shewanella sp. exonuclease

*Nucleotide sequence (SEQ ID NO. 6)* atgaacaacactaagaaacagccaactttattttggcacgattatgaaacatttggtgctaatccagccaaagataggccatcgcagtttgctgg tgtgcgtaccgacatggatctcaatatcattgctgagcctgtcacattttactgtaaagtcgcgaatgactacctgccctcacctgaagctattttaat tacaggtataacaccacagcttgctaaccttaaagggatgcctgaagctgagtttatggcacaaatccaccagttgtttagccaagaaaatacc tgtgttgtgggttacaactcaattagatttgatgatgaagtctcccgctatggcttttaccgtaacttttttgacccgtatgctagagaatggaaaaac ggtaatagtcgctgggatatcattgatttagtacgtgcttgttatgcctttaggcccgatggaataaactggccacaaaaagaagatggctctcca agttttaaactcgaacacttaaccgttgccaatggccttagccatgaaaaagcccacgatgctatgtctgatgtgtatgccactattgcgatggct aagcttatcaaatcagtgcagcctaaattgtttgaatattacttcaatctgcgccgaaaacaggaagtttcgaagctaatcgacgtactagaaat gaaaccgttagtgcatgtaagttcaaagattagcgcgctaaatggctgtaccacattaatcgcgccgctggccttcacacgactaataaaaat gcggttatctgtgtcaatttagccatggatgtcacgccgctcattgagttgaccgccgagcaaattcgagagcgcatgtacacaaggcgtgatg atttagcggaagatgagttacctattggcatcaaacaaatccatatcaacaaaagtccatttattgccggtgctaaatcattaaccgatgaaaat gccgctcgtcttgatattgataaagcatttgcaagagatcaatataagcggcttagacagcacccagagatacgagaaaagctcgttgcggtgt ttgacatcgagtccgatcgtatcattaccgatcccgatcttcagctttatagcggtggcttttttagccatgcggataaagcaaaaatggagatgat ccgtaataccaaacctattaatttagccgcactggagctgtcatttgacgatgagcgcttaccagaaatgttgtatcgatatagagcacgtaattat cctgaaacactggatgaatctgagagcattcgttggcgtgaattctgtcaatcaaggctcaatgatcctgattacatgataaaacttgaaaacatt attgaacaaaccgagcaagatgaagtaaagcaaaaattattacaggctttgtgtcattatcttagaaatctttag

*Amino acid sequence (SEQ ID No. 1)*

MNNTKKQPTLFWHDYETFGANPAKDRPSQFAGVRTDMDLNIIAEPVTFYCKVANDYLPSPEAILITGIT
PQLANLKGMPEAEFMAQIHQLFSQENTCVVGYNSIRFDDEVSRYGFYRNFFDPYAREWKNGNSRW
DIIDLVRACYAFRPDGINWPQKEDGSPSFKLEHLTVANGLSHEKAHDAMSDVYATIAMAKLIKSVQPKL
FEYYFNLRRKQEVSKLIDVLEMKPLVHVSSKISALNGCTTLIAPLAFHTTNKNAVICVNLAMDVTPLIELT
AEQIRERMYTRRDDLAEDELPIGIKQIHINKSPFIAGAKSLTDENAARLDIDKAFARDQYKRLRQHPEIR
EKLVAVFDIESDRIITDPDLQLYSGGFFSHADKAKMEMIRNTKPINLAALELSFDDERLPEMLYRYRAR
NYPETLDESESIRWREFCQSRLNDPDYMIKLENIIEQTEQDEVKQKLLQALCHYLRNL*

Figure 2: Halomonas sp. exonuclease

*Nucleotide sequence (SEQ ID No. 7)* atggcatcacccaatgctgcccctgccagttttctctggcatgattatgaaaccttcggggctgacccgcgccgcgatcggcccgctcagttcgct
gcactgcgcacggatgcagaactgaacgagatcggtgagcccatcgagctctactgcaaacccgccgatgactacctgcctcatcctgctgc
ctgtttgatcaccggtattaccccctcaaaaagcccagcgccatggtctccccgaagcagagttcgcgggtgagattcagcgccacatgagcga
gccgggtacctgcgtagtgggctacaacagcctgcgttttgatgacgaagtttcgcgccacctgttttaccgcaatttgcttgaccttattcccgcg
agtggcaaaacggcaattcccgctgggatttaatcgatattgtgcgcgcctttttatgcgctgcgcccggatggcattgaatggccgctgcgcgaa
gacggtgcacccagctttaagctcgagcacttaactgccgccaacggcattgcccatgagggtgcccacgatgcggtggcagatgtccgcgc
tactatcgccttggcgcggttgctcaaagtgcgcaatgccaagctgtttgactatctgctcggcctgcgcggtaagcgcgcggtggccaagcag
ctcgacttgcccaacgccaaaccgctgctgcatatctcccgccgttatcctgctagccggggctgtagtgcactagtcatgccgctggccgagc
acccgacaaaccctaatggggtgattgtttacgatttgagcgttgatcccagcgatatgctgagcatgtcggcggagcaaattcgtgagcgggt
gtttgtcagtcagcaggatctcgccgaaggcgaggcgcgcattccgctaaagatcatccatatcaaccgctgcccagtggtgttccccgctagt
gctttgaaagacgttgaggggcctcatcagggcgagtatggcaccatcgtcgcgcgcttaggcttagatgtggctgcctgtcggcagcactgg
aaaaccctgcgcgatgccagcggtgtcgccgctaaggtcgccgaggtgtttagtgccggttacgacgatgtaccccaagaccctgatctaatg
ctctattcgggcagtttcttctccgctgctgaccgtcagcagatggagcgggtgcgagagatggaaccgtgggacctggtcggtcagcgctttgc
gtttcaggatccgcgtttggaagagatgctgtttcgctttcgtgcgcgcagttaccccgacacgttggaaggcgaagagcgcgagcagtggga
ggcgtttcgctggatgcggatcaatgacccggccttggcgggctttacgcttaaggcgtttgcgcgggaaatcgagcagtacaatcagcaaac
cctcactgatcgcgagcggcaggttctggaagagctggtgatgttcgtggaagccatgatgccggcccaggcatttgatgcctga

*Amino acid sequence (SEQ ID NO. 2)*

MASPNAAPASFLWHDYETFGADPRRDRPAQFAALRTDAELNEIGEPIELYCKPADDYLPHPAACLITG
ITPQKAQRHGLPEAEFAGEIQRHMSEPGTCVVGYNSLRFDDEVSRHLFYRNLLDPYSREWQNGNSR
WDLIDIVRAFYALRPDGIEWPLREDGAPSFKLEHLTAANGIAHEGAHDAVADVRATIALARLLKVRNAK
LFDYLLGLRGKRAVAKQLDLPNAKPLLHISRRYPASRGCSALVMPLAEHPTNPNGVIVYDLSVDPSDM
LSMSAEQIRERVFVSQQDLAEGEARIPLKIIHINRCPVVFPASALKDVEGPHQGEYGTIVARLGLDVAA
CRQHWKTLRDASGVAAKVAEVFSAGYDDVPQDPDLMLYSGSFFSAADRQQMERVREMEPWDLVG
QRFAFQDPRLEEMLFRFRARSYPDTLEGEEREQWEAFRWMRINDPALAGFTLKAFAREIEQYNQQT
LTDRERQVLEELVMFVEAMMPAQAFDA*

Figure 3: Vibrio wodanis exonulcease

*Nucleotide sequence (SEQ ID No. 8)* atgccgcaggataacgcaccaagtttcttcttttttgattatgaaacatggggaactagcccatctctcgatcgcccatgccaatttgctggagttcg
taccgatgaagatttcaatatcattggtgagccattagttatttactgtcgccctccaattgattatttaccttctcctgaagcctgtttaattactggcat
cacgccacaaactgcggtaaataaaggcctgtctgagcctgagttcattactcaaatccataacgaattatcaaaaccaaatacttgctcgcta
ggctataacaacattcgttttgatgatgaagtttctcgctacaccttatatcgtaacttctttgaaccgtatggctggagctggcaaaacggcaactc
gcgttgggatctacttgatgtaatgcgtgctgtgtatgctctgcgtcctgaaggcattaaatggccaaaagacgaagaaggcaaaccaagcttt
agattagaaaaactctcgcaagcaaatggcattgaacatgaaaatgcccacgatgcgatggccgatgttattgccaccatcgagttagctaaa
gtcgttaaaaaagcacaacctaaaatgtttaactacctgctttctatgcgtcataaaaagaaagcggcaacgttaatcgatattgttgaaatgac
accgttaatgcacgtgtctggtatgtttggcgtagatagaggcaatattagttggattgtgcctgttgcttggcatcctaccaataacaacgccgtca
ttacgattgatttagcgttagacccaagtgtgttcctagaattagatgcagagcaattacatcaacgcatgtataccaaacgtgctgatctagccc
ctgacgaattgcctgttcctgtaaaattagtacatttaaacaagtgccctattcttgcgcctgctaaaacattgacggctgagaatgctgaaaatct
aaatgtggacagagccgcctgtttaaaaaatcttaaagtgatccgtgataaccctgagatcagacaaaagctaattgcgctttacagcattgag
cctaattatgagaaatcaaccaatgtagataccctctatatgatggtttcttctctcatgctgataaaacgacgattgatattatccgtcagtcaacg
cctgagcagcttatcgattttgaaccaaatgtcagtgacccacgcattaaacctctattattccgctatcgtgcgcgcaatttcccgcatacgcttaa
tgagacagagcaactgaaatggcaatcacatttacaagattacttccaaactcatttacctgaatacgaatcaagctttgagaatttatatcttga
atctgaaggcaatgagaaaaagactgcgatccttcgcgccgtttataattacgtacaacagttagtatcatga

*Amino acid sequence (SEQ ID No. 3)*

MPQDNAPSFFFFDYETWGTSPSLDRPCQFAGVRTDEDFNIIGEPLVIYCRPPIDYLPSPEACLITGITP
QTAVNKGLSEPEFITQIHNELSKPNTCSLGYNNIRFDDEVSRYTLYRNFFEPYGWSWQNGNSRWDLL
DVMRAVYALRPEGIKWPKDEEGKPSFRLEKLSQANGIEHENAHDAMADVIATIELAKVVKKAQPKMF
NYLLSMRHKKKAATLIDIVEMTPLMHVSGMFGVDRGNISWIVPVAWHPTNNNAVITIDLALDPSVFLEL
DAEQLHQRMYTKRADLAPDELPVPVKLVHLNKCPILAPAKTLTAENAENLNVDRAACLKNLKVIRDNP
EIRQKLIALYSIEPNYEKSTNVDTLLYDGFFSHADKTTIDIIRQSTPEQLIDFEPNVSDPRIKPLLFRYRAR
NFPHTLNETEQLKWQSHLQDYFQTHLPEYESSFENLYLESEGNEKKTAILRAVYNYVQQLVS

Figure 4: Psychromonas sp. exonuclease

*Nucleotide sequence (SEQ ID No 9)* atgaatcaagaatcccccaagccttctttggcacgattatgaaaccttcgggttaaacccaggaacggatcgcccttctcagtttgcaggcattcgt
actgatcttgatttaaatatcatttctgagccttatcaatggtactgcagaccacccaacgattatttacctgctcctgaagcgtgtttagtaacggga
ataacaccacaatatgcgttgcaacatggtgaatttgaaaaccaatttatatttaatatattgcagcaattccaacagcaaaacacgtgcgttgtt
gggtataacaatattcgctttgatgatgaagtcacacgctttactttgtatcgtaattttcatgacccttatcaaagagaatggcaaaatggctgctct
cgctgggacattattgacatggttcgcgcttgctatgcactcagaccagaaggtattgaatgggtatttgatgaaaatgatgcgccaagttttaaa
cttgagttattaactaaagctaatgacattgttcatcagcaagcacatgatgcgatgtcggatgtttatgccactatcgccatggcaaaactaatta
agacagcacatccaaagctatatgactattgttatagtttgagacaaaaaaataaagtattaaacgaactgaagcttggtacatttaaacctttag
ttcatatctctggtatgttttctgcgatgcaaggctgttgttcttatattttacctatcgcacaacacccaagtaacaataatgcagtgatagtgcttgatt
taaataaagatatttcacaacttttatcgttgagtgttgaagatatccaatcttacttatataccgctacggataatttaccagagggtattaatagac
cccctattaaattaatccatattaataaatgccctatcgtagcaagtgcaaaaacattaagtgcagagagagcaaaagaattaggggttgatgc
aaaacaatgccgtcaatcaatggatacgttctcagaaaataaacatttggttgagaaactgattgcagtgtttgacactgaatccaaaagcagc
aaggaacaacaaccagaacaaaaattgtattctggcggtttccctactgctaacgacaaaaatcaagcaaaagcgatcaccagtttgtcgcc
acaacaaattgctaattaccaagttacttttgatgatcctaattttgataatttatggtggcgatacaaagcaagaaattatccgcaaatgttatcact
tgaagagcaacaaaaatggggtagacacagagaagcttatcttattgaacatgtagataattatgttgcacgcttagaaatgctagtgattgag
catcaacatagcccagaaaagatcgaagtattgcaaaaactgggacattacttagagttttgacagggaatacataa

*Amino acid sequence (SEQ ID No 4)*

MNQESPSLLWHDYETFGLNPGTDRPSQFAGIRTDLDLNIISEPYQWYCRPPNDYLPAPEACLVTGITP
QYALQHGEFENQFIFNILQQFQQQNTCVVGYNNIRFDDEVTRFTLYRNFHDPYQREWQNGCSRWDII
DMVRACYALRPEGIEWVFDENDAPSFKLELLTKANDIVHQQAHDAMSDVYATIAMAKLIKTAHPKLYD
YCYSLRQKNKVLNELKLGTFKPLVHISGMFSAMQGCCSYILPIAQHPSNNNAVIVLDLNKDISQLLSLS
VEDIQSYLYTATDNLPEGINRPPIKLIHINKCPIVASAKTLSAERAKELGVDAKQCRQSMDTFSENKHLV
EKLIAVFDTESKSSKEQQPEQKLYSGGFPTANDKNQAKAITSLSPQQIANYQVTFDDPNFDNLWWRY
KARNYPQMLSLEEQQKWGRHREAYLIEHVDNYVARLEMLVIEHQHSPEKIEVLQKLGHYLEFLTGNT*

Figure 5: Moritella viscosa exonuclease

*Nucleotide sequence (SEQ ID No. 10)* atggataacaattcgaacaaaacagcaacagatctgcccactttttactggcatgattatgagacttttggcttaagtccgtcactggatcgcccttctcaatttgctggtattcgcaccgacatggactttaatgtgatcggcgaaccagatatgttttactgccgccaatcagatgattaccttccttcgccagaagctgccatgattactgggataacacctcaaaagacccaagcagaaggtgtaagtgaagcagagttcagtaaacgtattgaagcgcaattcagtcaaaaaaacacctgtatcattggttataacaacattcgctttgatgatgaagtaacacgtaatatcttctaccgtaatttctacgacccatacgcacacacctggaaagatggtaattcgcgctgggatattattgacttgatgcgcgcttgttatgctctgcgccctgaaggtattgtatggccagaaaatgatgatggtctaccaagtatgcgtcttgaattattaaccgccgcaaatggcattgagcacgctaatgcccatgatgctacttctgatgtatatgcaactatcgcgatggcgaagctagttaaagaaaaacaacctaagctgtttgatttcttatttaacctacgtagcaaacgtaaagttgaatccttggttgatatcatcaacatgacaccattagtgcatgtaagcggcatgtttggtgcagatcgcggattcacaagctgggtagtgccactggcttggcaccaaccaacaacaacgctgtgattgtagctgacttagcccaagacattacgccattattagaattgagcgcggatgaactgcgcgaacgtttatatacgccaaagaaagatctcggtgacttaaccccctatcccgctgaaacttattcatatcaacaagtgtccagtactcgcgccagcgaaaactctattacctgaaaacgcagaacgtttagggattgatcgcagcgcctgcctcgcaaacctaaaacgtttaaaagaaagcgcaacactgcgtgaaaatgttgtgggtgtttatcaagtagaacgtgaatatccaaaatcaaccaatgtggatgcaatgatctacgatggtttctttagtgcaggtgataaagcaaactttgaaatactacgtgaaacagcaccagagcaacttacaggactgcaactgaaagtcagtgattcgcgttttaatgaattattcttccgctatcgagcacgtaacttcccgcatttattcaatgcctgagcaacaaaaatggcttgaccactgccgaactgtgctagaagacagtgccccagcctatttgcacgtttagatgcattagcgatcgaaaacagccatgacgagcgaaaaatgaaactacttcaacagttatacctttatggtcaaaaaataattggcgcataa

*Amino acid sequence (SEQ ID No. 5)*

MDNNSNKTATDLPTFYWHDYETFGLSPSLDRPSQFAGIRTDMDFNVIGEPDMFYCRQSDDYLPSPE
AAMITGITPQKTQAEGVSEAEFSKRIEAQFSQKNTCIIGYNNIRFDDEVTRNIFYRNFYDPYAHTWKDG
NSRWDIIDLMRACYALRPEGIVWPENDDGLPSMRLELLTAANGIEHANAHDATSDVYATIAMAKLVKE
KQPKLFDFLFNLRSKRKVESLVDIINMTPLVHVSGMFGADRGFTSWVVPLAWHPTNNNAVIVADLAQ
DITPLLELSADELRERLYTPKKDLGDLTPIPLKLIHINKCPVLAPAKTLLPENAERLGIDRSACLANLKRL
KESATLRENVVGVYQVEREYPKSTNVDAMIYDGFFSAGDKANFEILRETAPEQLTGLQLKVSDSRFN
ELFFRYRARNFPHLLSMPEQQKWLDHCRTVLEDSAPAYFARLDALAIENSHDERKMKLLQQLYLYGQ
KIIGA

Figure 6: Alignment of the amino acid sequences of ExoI from different sources

```
                        ....|....| ....|....| ....|....| ....|....| ....|....|
                                10         20         30         40         50
E. coli K12             MMNDGKQQS- ---TFLFHDY ETFGTHPALD RPAQFAAIRT DSEFNVIGEP
Halomonas sp            MASPN----A APASFLWHDY ETFGADPRRD RPAQFAALRT DAELNEIGEP
Vibrio wodanis          MPQD------ NAPSFFFFDY ETWGTSPSLD RPCQFAGVRT DEDFNIIGEP
Shewanella sp           MNNTK----- KQPTLFWHDY ETFGANPAKD RPSQFAGVRT DMDLNIIAEP
Psychromonas sp         MNQE------ -SPSLLWHDY ETFGLNPGTD RPSQFAGIRT DLDLNIISEP
Moritella viscosa       MDNNSNKTAT DLPTFYWHDY ETFGLSPSLD RPSQFAGIRT DMDFNVIGEP
Consensus               * .          :: :.** **:*  *   * **.***.:** * ::* *.**

....|....| ....|....| ....|....| ....|....| ....|....|
                                60         70         80         90        100
E. coli K12             EVFYCKPADD YLPQPGAVLI TGITPQEARA KGENEAAFAA RIHSLFTVPK
Halomonas               IELYCKPADD YLPHPAACLI TGITPQKAQR HGLPEAEFAG EIQRHMSEPG
Vibrio wodanis          LVIYCRPPID YLPSPEACLI TGITPQTAVN KGLSEPEFIT QIHNELSKPN
Shewanella              VTFYCKVAND YLPSPEAILI TGITPQLANL KGMPEAEFMA QIHQLFSQEN
Psychromonas            YQWYCRPPND YLPAPEACLV TGITPQYALQ HGEFENQFIF NILQQFQQQN
Moritella viscosa       DMFYCRQSDD YLPSPEAAMI TGITPQKTQA EGVSEAEFSK RIEAQFSQKN
Consensus                **: . * *** * * :: ****** :   .*   *   .*    :

....|....| ....|....| ....|....| ....|....| ....|....|
                               110        120        130        140        150
E. coli K12             TCILGYNNVR FDDEVTRNIF YRNFYDPYAW SWQHDNSRWD LLDVMRACYA
Halomonas               TCVVGYNSLR FDDEVSRHLF YRNLLDPYSR EWQNGNSRWD LIDIVRAFYA
Vibrio wodanis          TCSLGYNNIR FDDEVSRYTL YRNFFEPYGW SWQNGNSRWD LLDVMRAVYA
Shewanella              TCVVGYNSIR FDDEVSRYGF YRNFFDPYAR EWKNGNSRWD IIDLVRACYA
Psychromonas            TCVVGYNNIR FDDEVTRFTL YRNFHDPYQR EWQNGCSRWD IIDMVRACYA
Moritella viscosa       TCIIGYNNIR FDDEVTRNIF YRNFYDPYAH TWKDGNSRWD IIDLMRACYA
Consensus               ** :***.:* ******:*  : ***: :**   *:.. **** ::*::** **

....|....| ....|....| ....|....| ....|....| ....|....|
                               160        170        180        190        200
E. coli K12             LRPEGINWPE NDDGLPSFRL EHLTKANGIE HSNAHDAMAD VYATIAMAKL
Halomonas               LRPDGIEWPL REDGAPSFKL EHLTAANGIA HEGAHDAVAD VRATIALARL
Vibrio wodanis          LRPEGIKWPK DEEGKPSFRL EKLSQANGIE HENAHDAMAD VIATIELAKV
Shewanella              FRPDGINWPQ KEDGSPSFKL EHLTVANGLS HEKAHDAMSD VYATIAMAKL
Psychromonas            LRPEGIEWVF DENDAPSFKL ELLTKANDIV HQQAHDAMSD VYATIAMAKL
Moritella viscosa       LRPEGIVWPE NDDGLPSMRL ELLTAANGIE HANAHDATSD VYATIAMAKL
Consensus               :**:** *    ::. **::* * *: **.:  *  **** :*  * *** :*::

....|....| ....|....| ....|....| ....|....| ....|....|
                               210        220        230        240        250
E. coli K12             VKTRQPRLFD YLFTHRNKHK LMALIDVPQM KPLVHVSGMF GAWRGNTSWV
Halomonas               LKVRNAKLFD YLLGLRGKRA VAKQLDLPNA KPLLHISRRY PASRGCSALV
Vibrio wodanis          VKKAQPKMFN YLLSMRHKKK AATLIDIVEM TPLMHVSGMF GVDRGNISWI
Shewanella              IKSVQPKLFE YYFNLRRKQE VSKLIDVLEM KPLVHVSSKI SALNGCTTLI
Psychromonas            IKTAHPKLYD YCYSLRQKNK VLNELKLGTF KPLVHISGMF SAMQGCCSYI
Moritella viscosa       VKEKQPKLFD FLFNLRSKRK VESLVDIINM TPLVHVSGMF GADRGFTSWV
Consensus               :*  :.:::: :  * *.    :.:    .**:*:*   . .*  : :
```

Figure 6 (cont.)

```
                 ....|....| ....|....| ....|....| ....|....| ....|....|
                        260        270        280        290        300
E. coli K12      APLAWHPENR NAVIMVDLAG DISPLLELDS DTLRERLYTA KTDLG-DNAA
Halomonas        MPLAEHPTNP NGVIVYDLSV DPSDMLSMSA EQIRERVFVS QQDLAEGEAR
Vibrio wodanis   VPVAWHPTNN NAVITIDLAL DPSVFLELDA EQLHQRMYTK RADLAPDELP
Shewanella       APLAFHTTNK NAVICVNLAM DVTPLIELTA EQIRERMYTR RDDLAEDELP
Psychromonas     LPIAQHPSNN NAVIVLDLNK DISQLLSLSV EDIQSYLYTA TDNLPEGINR
Moritella viscosa VPLAWHPTNN NAVIVADLAQ DITPLLELSA DELRERLYTP KKDLG-DLTP
Consensus        *:* *. *   *.**   :*   *  : ::.:   :  ::. ::.   :*   .

....|....| ....|....| ....|....| ....|....| ....|....|
                        310        320        330        340        350
E. coli K12      VPVKLVHINK CPVLAQANTL RPED------ ----ADRLGI NRQHCLDNLK
Halomonas        IPLKIIHINR CPVVFPASAL KDVEGPHQGE YGTIVARLGL DVAACRQHWK
Vibrio wodanis   VPVKLVHLNK CPILAPAKTL TAEN------ ----AENLNV DRAACLKNLK
Shewanella       IGIKQIHINK SPFIAGAKSL TDEN------ ----AARLDI DKAFARDQYK
Psychromonas     PPIKLIHINK CPIVASAKTL SAER------ ----AKELGV DAKQCRQSMD
Moritella viscosa IPLKLIHINK CPVLAPAKTL LPEN------ ----AERLGI DRSACLANLK
Consensus           :*  :*:*:  .*.:   *.:*              . .*.:  :   .   .

....|....| ....|....| ....|....| ....|....| ....|....|
                        360        370        380        390        400
E. coli K12      ILRENPQVRE KVVAIFAEAE PFTPSDNVDA QLYNG-FFSD ADRAAMKIVL
Halomonas        TLRDASGVAA KVAEVFSAGY D-DVPQDPDL MLYSGSFFSA ADRQQMERVR
Vibrio wodanis   VIRDNPEIRQ KLIALYSIEP NYEKSTNVDT LLYDG-FFSH ADKTTIDIIR
Shewanella       RLRQHPEIRE KLVAVFDIES D-RIITDPDL QLYSGGFFSH ADKAKMEMIR
Psychromonas     TFSENKHLVE KLIAVFDTES KSSKEQQPEQ KLYSGGFPTA NDKNQAKAIT
Moritella viscosa RLKESATLRE NVVGVYQVER EYPKSTNVDA MIYDG-FFSA GDKANFEILR
Consensus          :  :    :     ::   ::         : :    :*.* * :   *:    . :

....|....| ....|....| ....|....| ....|....| ....|....|
                        410        420        430        440        450
E. coli K12      ETEPRNLPAL DITFVDKRIE KLLFNYRARN FPGTLDYAEQ Q-----RWLE
Halomonas        EMEPWDLVGQ RFAFQDPRLE EMLFRFRARS YPDTLEGEER EQWEAFRWMR
Vibrio wodanis   QSTPEQLIDF EPNVSDPRIK PLLFRYRARN FPHTLNETEQ L-----KWQS
Shewanella       NTKPINLAAL ELSFDDERLP EMLYRYRARN YPETLDESES I-----RWRE
Psychromonas     SLSPQQIANY QVTFDDPNFD NLWWRYKARN YPQMLSLEEQ Q-----KWGR
Moritella viscosa ETAPEQLTGL QLKVSDSRFN ELFFRYRARN FPHLLSMPEQ Q-----KWLD
Consensus        .  *  ::       . * .:     : :.:** . :*  *.  *             :*

....|....| ....|....| ....|....| ....|....| ....|....|
                        460        470        480        490        500
E. coli K12      HRRQVFTPEF LQGYADELQM LVQQYADDKE KVALLKALWQ YAEEIV----
Halomonas        INDPALAGFT LKAFAREIEQ YNQQTLTD-R ERQVLEELVM FVEAMMPAQA
Vibrio wodanis   HLQDYFQTH- LPEYESSFEN LYLESEGNEK KTAILRAVYN YVQQLVS---
Shewanella       FCQSRLND-- -PDYMIKLEN IIEQTEQDEV KQKLLQALCH YLRNL-----
Psychromonas     HREAYLIEH- VDNYVARLEM LVIEHQHSPE KIEVLQKLGH YLEFLTGNT-
Moritella viscosa HCRTVLEDS- APAYFARLDA LAIENSHDER KMKLLQQLYL YGQKIIGA--
Consensus            :            :    ::     :    .    :*. :    :  . :
```

Figure 6 (cont.)

```
                        ...
E. coli K12             ---
Halomonas               FDA
Vibrio wodanis          ---
Shewanella              ---
Psychromonas            ---
Moritella viscosa       ---
Consensus
```

Figure 7: His-tagged Shewanella sp. exonuclease (amino acid SEQ ID No. 11; nucleotide SEQ ID No. 16)

```
1     ATG AAC AAC ACT AAG AAA CAG CCA ACT TTA TTT TGG CAC GAT TAT    45
1      M   N   N   T   K   K   Q   P   T   L   F   W   H   D   Y    15

46    GAA ACA TTT GGT GCT AAT CCA GCC AAA GAT AGG CCA TCG CAG TTT    90
16     E   T   F   G   A   N   P   A   K   D   R   P   S   Q   F    30

91    GCT GGT GTG CGT ACC GAC ATG GAT CTC AAT ATC ATT GCT GAG CCT   135
31     A   G   V   R   T   D   M   D   L   N   I   I   A   E   P    45

136   GTC ACA TTT TAC TGT AAA GTC GCG AAT GAC TAC CTG CCC TCA CCT   180
46     V   T   F   Y   C   K   V   A   N   D   Y   L   P   S   P    60

181   GAA GCT ATT TTA ATT ACA GGT ATA ACA CCA CAG CTT GCT AAC CTT   225
61     E   A   I   L   I   T   G   I   T   P   Q   L   A   N   L    75

226   AAA GGG ATG CCT GAA GCT GAG TTT ATG GCA CAA ATC CAC CAG TTG   270
76     K   G   M   P   E   A   E   F   M   A   Q   I   H   Q   L    90

271   TTT AGC CAA GAA AAT ACC TGT GTT GTG GGT TAC AAC TCA ATT AGA   315
91     F   S   Q   E   N   T   C   V   V   G   Y   N   S   I   R   105

316   TTT GAT GAT GAA GTC TCC CGC TAT GGC TTT TAC CGT AAC TTT TTT   360
106    F   D   D   E   V   S   R   Y   G   F   Y   R   N   F   F   120

361   GAC CCG TAT GCT AGA GAA TGG AAA AAC GGT AAT AGT CGC TGG GAT   405
121    D   P   Y   A   R   E   W   K   N   G   N   S   R   W   D   135

406   ATC ATT GAT TTA GTA CGT GCT TGT TAT GCC TTT AGG CCC GAT GGA   450
136    I   I   D   L   V   R   A   C   Y   A   F   R   P   D   G   150

451   ATA AAC TGG CCA CAA AAA GAA GAT GGC TCT CCA AGT TTT AAA CTC   495
151    I   N   W   P   Q   K   E   D   G   S   P   S   F   K   L   165

496   GAA CAC TTA ACC GTT GCC AAT GGC CTT AGC CAT GAA AAA GCC CAC   540
166    E   H   L   T   V   A   N   G   L   S   H   E   K   A   H   180

541   GAT GCT ATG TCT GAT GTG TAT GCC ACT ATT GCG ATG GCT AAG CTT   585
181    D   A   M   S   D   V   Y   A   T   I   A   M   A   K   L   195

586   ATC AAA TCA GTG CAG CCT AAA TTG TTT GAA TAT TAC TTC AAT CTG   630
196    I   K   S   V   Q   P   K   L   F   E   Y   Y   F   N   L   210

631   CGC CGA AAA CAG GAA GTT TCG AAG CTA ATC GAC GTA CTA GAA ATG   675
211    R   R   K   Q   E   V   S   K   L   I   D   V   L   E   M   225

676   AAA CCG TTA GTG CAT GTA AGT TCA AAG ATT AGC GCG CTA AAT GGC   720
226    K   P   L   V   H   V   S   S   K   I   S   A   L   N   G   240

721   TGT ACC ACA TTA ATC GCG CCG CTG GCC TTT CAC ACG ACT AAT AAA   765
241    C   T   T   L   I   A   P   L   A   F   H   T   T   N   K   255

766   AAT GCG GTT ATC TGT GTC AAT TTA GCC ATG GAT GTC ACG CCG CTC   810
256    N   A   V   I   C   V   N   L   A   M   D   V   T   P   L   270

811   ATT GAG TTG ACC GCC GAG CAA ATT CGA GAG CGC ATG TAC ACA AGG   855
271    I   E   L   T   A   E   Q   I   R   E   R   M   Y   T   R   285

856   CGT GAT GAT TTA GCG GAA GAT GAG TTA CCT ATT GGC ATC AAA CAA   900
286    R   D   D   L   A   E   D   E   L   P   I   G   I   K   Q   300

901   ATC CAT ATC AAC AAA AGT CCA TTT ATT GCC GGT GCT AAA TCA TTA   945
301    I   H   I   N   K   S   P   F   I   A   G   A   K   S   L   315
```

Figure 7 (cont.)

```
946   ACC GAT GAA AAT GCC GCT CGT CTT GAT ATT GAT AAA GCA TTT GCA   990
316    T   D   E   N   A   A   R   L   D   I   D   K   A   F   A   330

991   AGA GAT CAA TAT AAG CGG CTT AGA CAG CAC CCA GAG ATA CGA GAA   1035
331    R   D   Q   Y   K   R   L   R   Q   H   P   E   I   R   E   345

1036  AAG CTC GTT GCG GTG TTT GAC ATC GAG TCC GAT CGT ATC ATT ACC   1080
346    K   L   V   A   V   F   D   I   E   S   D   R   I   I   T   360

1081  GAT CCC GAT CTT CAG CTT TAT AGC GGT GGC TTT TTT AGC CAT GCG   1125
361    D   P   D   L   Q   L   Y   S   G   G   F   F   S   H   A   375

1126  GAT AAA GCA AAA ATG GAG ATG ATC CGT AAT ACC AAA CCT ATT AAT   1170
376    D   K   A   K   M   E   M   I   R   N   T   K   P   I   N   390

1171  TTA GCC GCA CTG GAG CTG TCA TTT GAC GAT GAG CGC TTA CCA GAA   1215
391    L   A   A   L   E   L   S   F   D   D   E   R   L   P   E   405

1216  ATG TTG TAT CGA TAT AGA GCA CGT AAT TAT CCT GAA ACA CTG GAT   1260
406    M   L   Y   R   Y   R   A   R   N   Y   P   E   T   L   D   420

1261  GAA TCT GAG AGC ATT CGT TGG CGT GAA TTC TGT CAA TCA AGG CTC   1305
421    E   S   E   S   I   R   W   R   E   F   C   Q   S   R   L   435

1306  AAT GAT CCT GAT TAC ATG ATA AAA CTT GAA AAC ATT ATT GAA CAA   1350
436    N   D   P   D   Y   M   I   K   L   E   N   I   I   E   Q   450

1351  ACC GAG CAA GAT GAA GTA AAG CAA AAA TTA TTA CAG GCT TTG TGT   1395
451    T   E   Q   D   E   V   K   Q   K   L   L   Q   A   L   C   465

1396  CAT TAT CTT AGA AAT CTT TCT GCA GGC CAT CAC CAT CAC CAT CAC   1440
466    H   Y   L   R   N   L   S   A   G   H   H   H   H   H   H   480

1441  TGA   1443
481    *
```

Figure 8: His-tagged Halomonas sp. exonuclease (amino acid SEQ ID No. 12; nucleotide SEQ ID No. 17)

```
1     ATG GCA TCA CCC AAT GCT GCC CCT GCC AGT TTT CTC TGG CAT GAT   45
1      M   A   S   P   N   A   A   P   A   S   F   L   W   H   D   15

46    TAT GAA ACC TTC GGG GCT GAC CCG CGC CGC GAT CGG CCC GCT CAG   90
16     Y   E   T   F   G   A   D   P   R   R   D   R   P   A   Q   30

91    TTC GCT GCA CTG CGC ACG GAT GCA GAA CTG AAC GAG ATC GGT GAG   135
31     F   A   A   L   R   T   D   A   E   L   N   E   I   G   E   45

136   CCC ATC GAG CTC TAC TGC AAA CCC GCC GAT GAC TAC CTG CCT CAT   180
46     P   I   E   L   Y   C   K   P   A   D   D   Y   L   P   H   60

181   CCT GCT GCC TGT TTG ATC ACC GGT ATT ACC CCT CAA AAA GCC CAG   225
61     P   A   A   C   L   I   T   G   I   T   P   Q   K   A   Q   75

226   CGC CAT GGT CTC CCC GAA GCA GAG TTC GCG GGT GAG ATT CAG CGC   270
76     R   H   G   L   P   E   A   E   F   A   G   E   I   Q   R   90

271   CAC ATG AGC GAG CCG GGT ACC TGC GTA GTG GGC TAC AAC AGC CTG   315
91     H   M   S   E   P   G   T   C   V   V   G   Y   N   S   L   105

316   CGT TTT GAT GAC GAA GTT TCG CGC CAC CTG TTT TAC CGC AAT TTG   360
106    R   F   D   D   E   V   S   R   H   L   F   Y   R   N   L   120

361   CTT GAC CCT TAT TCC CGC GAG TGG CAA AAC GGC AAT TCC CGC TGG   405
121    L   D   P   Y   S   R   E   W   Q   N   G   N   S   R   W   135

406   GAT TTA ATC GAT ATT GTG CGC GCC TTT TAT GCG CTG CGC CCG GAT   450
136    D   L   I   D   I   V   R   A   F   Y   A   L   R   P   D   150

451   GGC ATT GAA TGG CCG CTG CGC GAA GAC GGT GCA CCC AGC TTT AAG   495
151    G   I   E   W   P   L   R   E   D   G   A   P   S   F   K   165

496   CTC GAG CAC TTA ACT GCC GCC AAC GGC ATT GCC CAT GAG GGT GCC   540
166    L   E   H   L   T   A   A   N   G   I   A   H   E   G   A   180

541   CAC GAT GCG GTG GCA GAT GTC CGC GCT ACT ATC GCC TTG GCG CGG   585
181    H   D   A   V   A   D   V   R   A   T   I   A   L   A   R   195

586   TTG CTC AAA GTG CGC AAT GCC AAG CTG TTT GAC TAT CTG CTC GGC   630
196    L   L   K   V   R   N   A   K   L   F   D   Y   L   L   G   210

631   CTG CGC GGT AAG CGC GCG GTG GCC AAG CAG CTC GAC TTG CCC AAC   675
211    L   R   G   K   R   A   V   A   K   Q   L   D   L   P   N   225

676   GCC AAA CCG CTG CTG CAT ATC TCC CGC CGT TAT CCT GCT AGC CGG   720
226    A   K   P   L   L   H   I   S   R   R   Y   P   A   S   R   240

721   GGC TGT AGT GCA CTA GTC ATG CCG CTG GCC GAG CAC CCG ACA AAC   765
241    G   C   S   A   L   V   M   P   L   A   E   H   P   T   N   255

766   CCT AAT GGG GTG ATT GTT TAC GAT TTG AGC GTT GAT CCC AGC GAT   810
256    P   N   G   V   I   V   Y   D   L   S   V   D   P   S   D   270

811   ATG CTG AGC ATG TCG GCG GAG CAA ATT CGT GAG CGG GTG TTT GTC   855
271    M   L   S   M   S   A   E   Q   I   R   E   R   V   F   V   285

856   AGT CAG CAG GAT CTC GCC GAA GGC GAG GCG CGC ATT CCG CTA AAG   900
286    S   Q   Q   D   L   A   E   G   E   A   R   I   P   L   K   300
```

Figure 8 (cont.)

```
901   ATC ATC CAT ATC AAC CGC TGC CCA GTG GTG TTC CCC GCT AGT GCT   945
301    I   I   H   I   N   R   C   P   V   V   F   P   A   S   A   315

946   TTG AAA GAC GTT GAG GGG CCT CAT CAG GGC GAG TAT GGC ACC ATC   990
316    L   K   D   V   E   G   P   H   Q   G   E   Y   G   T   I   330

991   GTC GCG CGC TTA GGC TTA GAT GTG GCT GCC TGT CGG CAG CAC TGG   1035
331    V   A   R   L   G   L   D   V   A   A   C   R   Q   H   W   345

1036  AAA ACC CTG CGC GAT GCC AGC GGT GTC GCC GCT AAG GTC GCC GAG   1080
346    K   T   L   R   D   A   S   G   V   A   A   K   V   A   E   360

1081  GTG TTT AGT GCC GGT TAC GAC GAT GTA CCC CAA GAC CCT GAT CTA   1125
361    V   F   S   A   G   Y   D   D   V   P   Q   D   P   D   L   375

1126  ATG CTC TAT TCG GGC AGT TTC TTC TCC GCT GCT GAC CGT CAG CAG   1170
376    M   L   Y   S   G   S   F   F   S   A   A   D   R   Q   Q   390

1171  ATG GAG CGG GTG CGA GAG ATG GAA CCG TGG GAC CTG GTC GGT CAG   1215
391    M   E   R   V   R   E   M   E   P   W   D   L   V   G   Q   405

1216  CGC TTT GCG TTT CAG GAT CCG CGT TTG GAA GAG ATG CTG TTT CGC   1260
406    R   F   A   F   Q   D   P   R   L   E   E   M   L   F   R   420

1261  TTT CGT GCG CGC AGT TAC CCC GAC ACG TTG GAA GGC GAA GAG CGC   1305
421    F   R   A   R   S   Y   P   D   T   L   E   G   E   E   R   435

1306  GAG CAG TGG GAG GCG TTT CGC TGG ATG CGG ATC AAT GAC CCG GCC   1350
436    E   Q   W   E   A   F   R   W   M   R   I   N   D   P   A   450

1351  TTG GCG GGC TTT ACG CTT AAG GCG TTT GCG CGG GAA ATC GAG CAG   1395
451    L   A   G   F   T   L   K   A   F   A   R   E   I   E   Q   465

1396  TAC AAT CAG CAA ACC CTC ACT GAT CGC GAG CGG CAG GTT CTG GAA   1440
466    Y   N   Q   Q   T   L   T   D   R   E   R   Q   V   L   E   480

1441  GAG CTG GTG ATG TTC GTG GAA GCC ATG ATG CCG GCC CAG GCA TTT   1485
481    E   L   V   M   F   V   E   A   M   M   P   A   Q   A   F   495

1486  GAT GCC TCT GCA GGC CAT CAC CAT CAC CAT CAC TGA   1521
496    D   A   S   A   G   H   H   H   H   H   H   *
```

Figure 9: His-tagged *Vibrio wodanis* exonuclease (amino acid SEQ ID No. 13; nucleotide SEQ ID No. 18)

```
1     ATG CCG CAG GAT AAC GCA CCA AGT TTC TTC TTT TTT GAT TAT GAA   45
1      M   P   Q   D   N   A   P   S   F   F   F   F   D   Y   E    15

46    ACA TGG GGA ACT AGC CCA TCT CTC GAT CGC CCA TGC CAA TTT GCT   90
16     T   W   G   T   S   P   S   L   D   R   P   C   Q   F   A    30

91    GGA GTT CGT ACC GAT GAA GAT TTC AAT ATC ATT GGT GAG CCA TTA  135
31     G   V   R   T   D   E   D   F   N   I   I   G   E   P   L    45

136   GTT ATT TAC TGT CGC CCT CCA ATT GAT TAT TTA CCT TCT CCT GAA  180
46     V   I   Y   C   R   P   P   I   D   Y   L   P   S   P   E    60

181   GCC TGT TTA ATT ACT GGC ATC ACG CCA CAA ACT GCG GTA AAT AAA  225
61     A   C   L   I   T   G   I   T   P   Q   T   A   V   N   K    75

226   GGC CTG TCT GAG CCT GAG TTC ATT ACT CAA ATC CAT AAC GAA TTA  270
76     G   L   S   E   P   E   F   I   T   Q   I   H   N   E   L    90

271   TCA AAA CCA AAT ACT TGC TCG CTA GGC TAT AAC AAC ATT CGT TTT  315
91     S   K   P   N   T   C   S   L   G   Y   N   N   I   R   F   105

316   GAT GAT GAA GTT TCT CGC TAC ACC TTA TAT CGT AAC TTC TTT GAA  360
106    D   D   E   V   S   R   Y   T   L   Y   R   N   F   F   E   120

361   CCG TAT GGC TGG AGC TGG CAA AAC GGC AAC TCG CGT TGG GAT CTA  405
121    P   Y   G   W   S   W   Q   N   G   N   S   R   W   D   L   135

406   CTT GAT GTA ATG CGT GCT GTG TAT GCT CTG CGT CCT GAA GGC ATT  450
136    L   D   V   M   R   A   V   Y   A   L   R   P   E   G   I   150

451   AAA TGG CCA AAA GAC GAA GAA GGC AAA CCA AGC TTT AGA TTA GAA  495
151    K   W   P   K   D   E   E   G   K   P   S   F   R   L   E   165

496   AAA CTC TCG CAA GCA AAT GGC ATT GAA CAT GAA AAT GCC CAC GAT  540
166    K   L   S   Q   A   N   G   I   E   H   E   N   A   H   D   180

541   GCG ATG GCC GAT GTT ATT GCC ACC ATC GAG TTA GCT AAA GTC GTT  585
181    A   M   A   D   V   I   A   T   I   E   L   A   K   V   V   195

586   AAA AAA GCA CAA CCT AAA ATG TTT AAC TAC CTG CTT TCT ATG CGT  630
196    K   K   A   Q   P   K   M   F   N   Y   L   L   S   M   R   210

631   CAT AAA AAG AAA GCG GCA ACG TTA ATC GAT ATT GTT GAA ATG ACA  675
211    H   K   K   K   A   A   T   L   I   D   I   V   E   M   T   225

676   CCG TTA ATG CAC GTG TCT GGT ATG TTT GGC GTA GAT AGA GGC AAT  720
226    P   L   M   H   V   S   G   M   F   G   V   D   R   G   N   240

721   ATT AGT TGG ATT GTG CCT GTT GCT TGG CAT CCT ACC AAT AAC AAC  765
241    I   S   W   I   V   P   V   A   W   H   P   T   N   N   N   255

766   GCC GTC ATT ACG ATT GAT TTA GCG TTA GAC CCA AGT GTG TTC CTA  810
256    A   V   I   T   I   D   L   A   L   D   P   S   V   F   L   270

811   GAA TTA GAT GCA GAG CAA TTA CAT CAA CGC ATG TAT ACC AAA CGT  855
271    E   L   D   A   E   Q   L   H   Q   R   M   Y   T   K   R   285

856   GCT GAT CTA GCC CCT GAC GAA TTG CCT GTT CCT GTA AAA TTA GTA  900
286    A   D   L   A   P   D   E   L   P   V   P   V   K   L   V   300
```

Figure 9 (cont.)

```
901   CAT TTA AAC AAG TGC CCT ATT CTT GCG CCT GCT AAA ACA TTG ACG   945
301    H   L   N   K   C   P   I   L   A   P   A   K   T   L   T   315

946   GCT GAG AAT GCT GAA AAT CTA AAT GTG GAC AGA GCC GCC TGT TTA   990
316    A   E   N   A   E   N   L   N   V   D   R   A   A   C   L   330

991   AAA AAT CTT AAA GTG ATC CGT GAT AAC CCT GAG ATC AGA CAA AAG  1035
331    K   N   L   K   V   I   R   D   N   P   E   I   R   Q   K   345

1036  CTA ATT GCG CTT TAC AGC ATT GAG CCT AAT TAT GAG AAA TCA ACC  1080
346    L   I   A   L   Y   S   I   E   P   N   Y   E   K   S   T   360

1081  AAT GTA GAT ACC CTT CTA TAT GAT GGT TTC TTC TCT CAT GCT GAT  1125
361    N   V   D   T   L   L   Y   D   G   F   F   S   H   A   D   375

1126  AAA ACG ACG ATT GAT ATT ATC CGT CAG TCA ACG CCT GAG CAG CTT  1170
376    K   T   T   I   D   I   I   R   Q   S   T   P   E   Q   L   390

1171  ATC GAT TTT GAA CCA AAT GTC AGT GAC CCA CGC ATT AAA CCT CTA  1215
391    I   D   F   E   P   N   V   S   D   P   R   I   K   P   L   405

1216  TTA TTC CGC TAT CGT GCG CGC AAT TTC CCG CAT ACG CTT AAT GAG  1260
406    L   F   R   Y   R   A   R   N   F   P   H   T   L   N   E   420

1261  ACA GAG CAA CTG AAA TGG CAA TCA CAT TTA CAA GAT TAC TTC CAA  1305
421    T   E   Q   L   K   W   Q   S   H   L   Q   D   Y   F   Q   435

1306  ACT CAT TTA CCT GAA TAC GAA TCA AGC TTT GAG AAT TTA TAT CTT  1350
436    T   H   L   P   E   Y   E   S   S   F   E   N   L   Y   L   450

1351  GAA TCT GAA GGC AAT GAG AAA AAG ACT GCG ATC CTT CGC GCC GTT  1395
451    E   S   E   G   N   E   K   K   T   A   I   L   R   A   V   465

1396  TAT AAT TAC GTA CAA CAG TTA GTA TCA TCT GCA GGC CAT CAC CAT  1440
466    Y   N   Y   V   Q   Q   L   V   S   S   A   G   H   H   H   480

1441  CAC CAT CAC TGA  1452
481    H   H   H   *
```

Figure 10: His-tagged Psychromonas sp. exonuclease (amino acid SEQ ID No. 14; nucleotide SEQ ID No. 19)

```
1     ATG AAT CAA GAA TCC CCA AGC CTT CTT TGG CAC GAT TAT GAA ACC    45
1      M   N   Q   E   S   P   S   L   L   W   H   D   Y   E   T    15

46    TTC GGG TTA AAC CCA GGA ACG GAT CGC CCT TCT CAG TTT GCA GGC    90
16     F   G   L   N   P   G   T   D   R   P   S   Q   F   A   G    30

91    ATT CGT ACT GAT CTT GAT TTA AAT ATC ATT TCT GAG CCT TAT CAA   135
31     I   R   T   D   L   D   L   N   I   I   S   E   P   Y   Q    45

136   TGG TAC TGC AGA CCA CCC AAC GAT TAT TTA CCT GCT CCT GAA GCG   180
46     W   Y   C   R   P   P   N   D   Y   L   P   A   P   E   A    60

181   TGT TTA GTA ACG GGA ATA ACA CCA CAA TAT GCG TTG CAA CAT GGT   225
61     C   L   V   T   G   I   T   P   Q   Y   A   L   Q   H   G    75

226   GAA TTT GAA AAC CAA TTT ATA TTT AAT ATA TTG CAG CAA TTC CAA   270
76     E   F   E   N   Q   F   I   F   N   I   L   Q   Q   F   Q    90

271   CAG CAA AAC ACG TGC GTT GTT GGG TAT AAC AAT ATT CGC TTT GAT   315
91     Q   Q   N   T   C   V   V   G   Y   N   N   I   R   F   D   105

316   GAT GAA GTC ACA CGC TTT ACT TTG TAT CGT AAT TTT CAT GAC CCT   360
106    D   E   V   T   R   F   T   L   Y   R   N   F   H   D   P   120

361   TAT CAA AGA GAA TGG CAA AAT GGC TGC TCT CGC TGG GAC ATT ATT   405
121    Y   Q   R   E   W   Q   N   G   C   S   R   W   D   I   I   135

406   GAC ATG GTT CGC GCT TGC TAT GCA CTC AGA CCA GAA GGT ATT GAA   450
136    D   M   V   R   A   C   Y   A   L   R   P   E   G   I   E   150

451   TGG GTA TTT GAT GAA AAT GAT GCG CCA AGT TTT AAA CTT GAG TTA   495
151    W   V   F   D   E   N   D   A   P   S   F   K   L   E   L   165

496   TTA ACT AAA GCT AAT GAC ATT GTT CAT CAG CAA GCA CAT GAT GCG   540
166    L   T   K   A   N   D   I   V   H   Q   Q   A   H   D   A   180

541   ATG TCG GAT GTT TAT GCC ACT ATC GCC ATG GCA AAA CTA ATT AAG   585
181    M   S   D   V   Y   A   T   I   A   M   A   K   L   I   K   195

586   ACA GCA CAT CCA AAG CTA TAT GAC TAT TGT TAT AGT TTG AGA CAA   630
196    T   A   H   P   K   L   Y   D   Y   C   Y   S   L   R   Q   210

631   AAA AAT AAA GTA TTA AAC GAA CTG AAG CTT GGT ACA TTT AAA CCT   675
211    K   N   K   V   L   N   E   L   K   L   G   T   F   K   P   225

676   TTA GTT CAT ATC TCT GGT ATG TTT TCT GCG ATG CAA GGC TGT TGT   720
226    L   V   H   I   S   G   M   F   S   A   M   Q   G   C   C   240

721   TCT TAT ATT TTA CCT ATC GCA CAA CAC CCA AGT AAC AAT AAT GCA   765
241    S   Y   I   L   P   I   A   Q   H   P   S   N   N   N   A   255

766   GTG ATA GTG CTT GAT TTA AAT AAA GAT ATT TCA CAA CTT TTA TCG   810
256    V   I   V   L   D   L   N   K   D   I   S   Q   L   L   S   270

811   TTG AGT GTT GAA GAT ATC CAA TCT TAC TTA TAT ACC GCT ACG GAT   855
271    L   S   V   E   D   I   Q   S   Y   L   Y   T   A   T   D   285
```

Figure 10 (cont.)

```
856   AAT TTA CCA GAG GGT ATT AAT AGA CCC CCT ATT AAA TTA ATC CAT   900
286    N   L   P   E   G   I   N   R   P   P   I   K   L   I   H   300

901   ATT AAT AAA TGC CCT ATC GTA GCA AGT GCA AAA ACA TTA AGT GCA   945
301    I   N   K   C   P   I   V   A   S   A   K   T   L   S   A   315

946   GAG AGA GCA AAA GAA TTA GGG GTT GAT GCA AAA CAA TGC CGT CAA   990
316    E   R   A   K   E   L   G   V   D   A   K   Q   C   R   Q   330

991   TCA ATG GAT ACG TTC TCA GAA AAT AAA CAT TTG GTT GAG AAA CTG   1035
331    S   M   D   T   F   S   E   N   K   H   L   V   E   K   L   345

1036  ATT GCA GTG TTT GAC ACT GAA TCC AAA AGC AGC AAG GAA CAA CAA   1080
346    I   A   V   F   D   T   E   S   K   S   S   K   E   Q   Q   360

1081  CCA GAA CAA AAA TTG TAT TCT GGC GGT TTC CCT ACT GCT AAC GAC   1125
361    P   E   Q   K   L   Y   S   G   G   F   P   T   A   N   D   375

1126  AAA AAT CAA GCA AAA GCG ATC ACC AGT TTG TCG CCA CAA CAA ATT   1170
376    K   N   Q   A   K   A   I   T   S   L   S   P   Q   Q   I   390

1171  GCT AAT TAC CAA GTT ACT TTT GAT GAT CCT AAT TTT GAT AAT TTA   1215
391    A   N   Y   Q   V   T   F   D   D   P   N   F   D   N   L   405

1216  TGG TGG CGA TAC AAA GCA AGA AAT TAT CCG CAA ATG TTA TCA CTT   1260
406    W   W   R   Y   K   A   R   N   Y   P   Q   M   L   S   L   420

1261  GAA GAG CAA CAA AAA TGG GGT AGA CAC AGA GAA GCT TAT CTT ATT   1305
421    E   E   Q   Q   K   W   G   R   H   R   E   A   Y   L   I   435

1306  GAA CAT GTA GAT AAT TAT GTT GCA CGC TTA GAA ATG CTA GTG ATT   1350
436    E   H   V   D   N   Y   V   A   R   L   E   M   L   V   I   450

1351  GAG CAT CAA CAT AGC CCA GAA AAG ATC GAA GTA TTG CAA AAA CTG   1395
451    E   H   Q   H   S   P   E   K   I   E   V   L   Q   K   L   465

1396  GGA CAT TAC TTA GAG TTT TTG ACA GGG AAT ACA TCT GCA GGC CAT   1440
466    G   H   Y   L   E   F   L   T   G   N   T   S   A   G   H   480

1441  CAC CAT CAC CAT CAC TGA   1455
481    H   H   H   H   H   *
```

**Figure 11: His-tagged *Moritella viscosa* exonuclease (amino acid SEQ ID No. 15; nucleotide SEQ ID No. 20)**

```
1    ATG GAT AAC AAT TCG AAC AAA ACA GCA ACA GAT CTG CCC ACT TTT    45
1     M   D   N   N   S   N   K   T   A   T   D   L   P   T   F    15

46   TAC TGG CAT GAT TAT GAG ACT TTT GGC TTA AGT CCG TCA CTG GAT    90
16    Y   W   H   D   Y   E   T   F   G   L   S   P   S   L   D    30

91   CGC CCT TCT CAA TTT GCT GGT ATT CGC ACC GAC ATG GAC TTT AAT    135
31    R   P   S   Q   F   A   G   I   R   T   D   M   D   F   N    45

136  GTG ATC GGC GAA CCA GAT ATG TTT TAC TGC CGC CAA TCA GAT GAT    180
46    V   I   G   E   P   D   M   F   Y   C   R   Q   S   D   D    60

181  TAC CTT CCT TCG CCA GAA GCT GCC ATG ATT ACT GGG ATA ACA CCT    225
61    Y   L   P   S   P   E   A   A   M   I   T   G   I   T   P    75

226  CAA AAG ACC CAA GCA GAA GGT GTA AGT GAA GCA GAG TTC AGT AAA    270
76    Q   K   T   Q   A   E   G   V   S   E   A   E   F   S   K    90

271  CGT ATT GAA GCG CAA TTC AGT CAA AAA AAC ACC TGT ATC ATT GGT    315
91    R   I   E   A   Q   F   S   Q   K   N   T   C   I   I   G    105

316  TAT AAC AAC ATT CGC TTT GAT GAT GAA GTA ACA CGT AAT ATC TTC    360
106   Y   N   N   I   R   F   D   D   E   V   T   R   N   I   F    120

361  TAC CGT AAT TTC TAC GAC CCA TAC GCA CAC ACC TGG AAA GAT GGT    405
121   Y   R   N   F   Y   D   P   Y   A   H   T   W   K   D   G    135

406  AAT TCG CGC TGG GAT ATT ATT GAC TTG ATG CGC GCT TGT TAT GCT    450
136   N   S   R   W   D   I   I   D   L   M   R   A   C   Y   A    150

451  CTG CGC CCT GAA GGT ATT GTA TGG CCA GAA AAT GAT GAT GGT CTA    495
151   L   R   P   E   G   I   V   W   P   E   N   D   D   G   L    165

496  CCA AGT ATG CGT CTT GAA TTA TTA ACC GCC GCA AAT GGC ATT GAG    540
166   P   S   M   R   L   E   L   L   T   A   A   N   G   I   E    180

541  CAC GCT AAT GCC CAT GAT GCT ACT TCT GAT GTA TAT GCA ACT ATC    585
181   H   A   N   A   H   D   A   T   S   D   V   Y   A   T   I    195

586  GCG ATG GCG AAG CTA GTT AAA GAA AAA CAA CCT AAG CTG TTT GAT    630
196   A   M   A   K   L   V   K   E   K   Q   P   K   L   F   D    210

631  TTC TTA TTT AAC CTA CGT AGC AAA CGT AAA GTT GAA TCC TTG GTT    675
211   F   L   F   N   L   R   S   K   R   K   V   E   S   L   V    225

676  GAT ATC ATC AAC ATG ACA CCA TTA GTG CAT GTA AGC GGC ATG TTT    720
226   D   I   I   N   M   T   P   L   V   H   V   S   G   M   F    240

721  GGT GCA GAT CGC GGA TTC ACA AGC TGG GTA GTG CCA CTG GCT TGG    765
241   G   A   D   R   G   F   T   S   W   V   V   P   L   A   W    255

766  CAC CCA ACC AAC AAC AAC GCT GTG ATT GTA GCT GAC TTA GCC CAA    810
256   H   P   T   N   N   N   A   V   I   V   A   D   L   A   Q    270

811  GAC ATT ACG CCA TTA TTA GAA TTG AGC GCG GAT GAA CTG CGC GAA    855
271   D   I   T   P   L   L   E   L   S   A   D   E   L   R   E    285

856  CGT TTA TAT ACG CCA AAG AAA GAT CTC GGT GAC TTA ACC CCT ATC    900
286   R   L   Y   T   P   K   K   D   L   G   D   L   T   P   I    300

901  CCG CTG AAA CTT ATT CAT ATC AAC AAG TGT CCA GTA CTC GCG CCA    945
301   P   L   K   L   I   H   I   N   K   C   P   V   L   A   P    315
```

Figure 11 (cont.)

```
946   GCG AAA ACT CTA TTA CCT GAA AAC GCA GAA CGT TTA GGG ATT GAT   990
316    A   K   T   L   L   P   E   N   A   E   R   L   G   I   D   330

991   CGC AGC GCC TGC CTC GCA AAC CTA AAA CGT TTA AAA GAA AGC GCA   1035
331    R   S   A   C   L   A   N   L   K   R   L   K   E   S   A   345

1036  ACA CTG CGT GAA AAT GTT GTG GGT GTT TAT CAA GTA GAA CGT GAA   1080
346    T   L   R   E   N   V   V   G   V   Y   Q   V   E   R   E   360

1081  TAT CCA AAA TCA ACC AAT GTG GAT GCA ATG ATC TAC GAT GGT TTC   1125
361    Y   P   K   S   T   N   V   D   A   M   I   Y   D   G   F   375

1126  TTT AGT GCA GGT GAT AAA GCA AAC TTT GAA ATA CTA CGT GAA ACA   1170
376    F   S   A   G   D   K   A   N   F   E   I   L   R   E   T   390

1171  GCA CCA GAG CAA CTT ACA GGA CTG CAA CTG AAA GTC AGT GAT TCG   1215
391    A   P   E   Q   L   T   G   L   Q   L   K   V   S   D   S   405

1216  CGT TTT AAT GAA TTA TTC TTC CGC TAT CGA GCA CGT AAC TTC CCG   1260
406    R   F   N   E   L   F   F   R   Y   R   A   R   N   F   P   420

1261  CAT TTA TTA TCA ATG CCT GAG CAA CAA AAA TGG CTT GAC CAC TGC   1305
421    H   L   L   S   M   P   E   Q   Q   K   W   L   D   H   C   435

1306  CGA ACT GTG CTA GAA GAC AGT GCC CCA GCC TAT TTT GCA CGT TTA   1350
436    R   T   V   L   E   D   S   A   P   A   Y   F   A   R   L   450

1351  GAT GCA TTA GCG ATC GAA AAC AGC CAT GAC GAG CGA AAA ATG AAA   1395
451    D   A   L   A   I   E   N   S   H   D   E   R   K   M   K   465

1396  CTA CTT CAA CAG TTA TAC CTT TAT GGT CAA AAA ATA ATT GGC GCA   1440
466    L   L   Q   Q   L   Y   L   Y   G   Q   K   I   I   G   A   480

1441  TCT GCA GGC CAT CAC CAT CAC CAT CAC TGA    1470
481    S   A   G   H   H   H   H   H   H   *
```

HL-Exo I (Ha)

HL-Exo I (Ps)

HL-Exo I (Sh)

HL-Exo I (Mv)

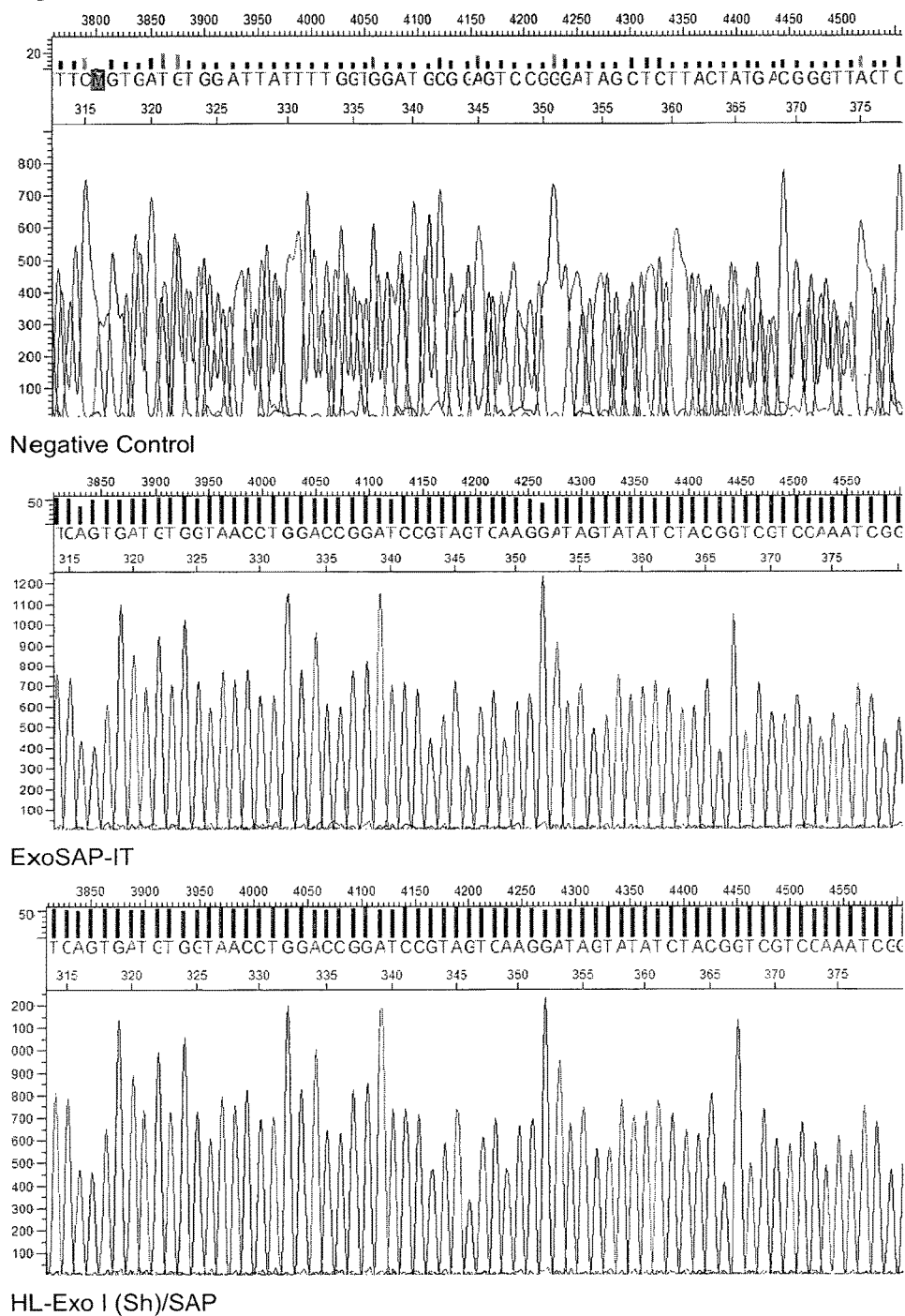

Negative Control

ExoSAP-IT

HL-Exo I (Sh)/SAP

ExoSAP-IT

HL-Exo I (Sh)/SAP

Negative control

ExoSAP-IT

HL-ExoI (Sh)/SAP

HL-ExoI (Ps)/SAP

HL-ExoI (Mw)/SAP

HL-ExoI (Vw)/SAP

SEQUENCE LISTING

<160> NUMBER OF SEQ ID NOS: 32

<210> SEQ ID NO 1
<211> LENGTH: 471
<212> TYPE: PRT
<213> ORGANISM: Shewanella sp.

<400> SEQUENCE: 1

```
Met Asn Asn Thr Lys Lys Gln Pro Thr Leu Phe Trp His Asp Tyr Glu
1               5                   10                  15

Thr Phe Gly Ala Asn Pro Ala Lys Asp Arg Pro Ser Gln Phe Ala Gly
            20                  25                  30

Val Arg Thr Asp Met Asp Leu Asn Ile Ile Ala Glu Pro Val Thr Phe
        35                  40                  45

Tyr Cys Lys Val Ala Asn Asp Tyr Leu Pro Ser Pro Glu Ala Ile Leu
    50                  55                  60

Ile Thr Gly Ile Thr Pro Gln Leu Ala Asn Leu Lys Gly Met Pro Glu
65                  70                  75                  80

Ala Glu Phe Met Ala Gln Ile His Gln Leu Phe Ser Gln Glu Asn Thr
                85                  90                  95

Cys Val Val Gly Tyr Asn Ser Ile Arg Phe Asp Asp Glu Val Ser Arg
            100                 105                 110

Tyr Gly Phe Tyr Arg Asn Phe Phe Asp Pro Tyr Ala Arg Glu Trp Lys
        115                 120                 125

Asn Gly Asn Ser Arg Trp Asp Ile Ile Asp Leu Val Arg Ala Cys Tyr
    130                 135                 140

Ala Phe Arg Pro Asp Gly Ile Asn Trp Pro Gln Lys Glu Asp Gly Ser
145                 150                 155                 160

Pro Ser Phe Lys Leu Glu His Leu Thr Val Ala Asn Gly Leu Ser His
                165                 170                 175

Glu Lys Ala His Asp Ala Met Ser Asp Val Tyr Ala Thr Ile Ala Met
            180                 185                 190

Ala Lys Leu Ile Lys Ser Val Gln Pro Lys Leu Phe Glu Tyr Tyr Phe
        195                 200                 205

Asn Leu Arg Arg Lys Gln Glu Val Ser Lys Leu Ile Asp Val Leu Glu
    210                 215                 220

Met Lys Pro Leu Val His Val Ser Ser Lys Ile Ser Ala Leu Asn Gly
225                 230                 235                 240

Cys Thr Thr Leu Ile Ala Pro Leu Ala Phe His Thr Thr Asn Lys Asn
                245                 250                 255

Ala Val Ile Cys Val Asn Leu Ala Met Asp Val Thr Pro Leu Ile Glu
            260                 265                 270

Leu Thr Ala Glu Gln Ile Arg Glu Arg Met Tyr Thr Arg Arg Asp Asp
        275                 280                 285

Leu Ala Glu Asp Glu Leu Pro Ile Gly Ile Lys Gln Ile His Ile Asn
    290                 295                 300

Lys Ser Pro Phe Ile Ala Gly Ala Lys Ser Leu Thr Asp Glu Asn Ala
305                 310                 315                 320

Ala Arg Leu Asp Ile Asp Lys Ala Phe Ala Arg Asp Gln Tyr Lys Arg
                325                 330                 335
```

```
Leu Arg Gln His Pro Glu Ile Arg Glu Lys Leu Val Ala Val Phe Asp
                340                 345                 350

Ile Glu Ser Asp Arg Ile Ile Thr Asp Pro Asp Leu Gln Leu Tyr Ser
            355                 360                 365

Gly Gly Phe Phe Ser His Ala Asp Lys Ala Lys Met Glu Met Ile Arg
        370                 375                 380

Asn Thr Lys Pro Ile Asn Leu Ala Ala Leu Glu Leu Ser Phe Asp Asp
385                 390                 395                 400

Glu Arg Leu Pro Glu Met Leu Tyr Arg Tyr Arg Ala Arg Asn Tyr Pro
                405                 410                 415

Glu Thr Leu Asp Glu Ser Glu Ser Ile Arg Trp Arg Glu Phe Cys Gln
            420                 425                 430

Ser Arg Leu Asn Asp Pro Asp Tyr Met Ile Lys Leu Glu Asn Ile Ile
        435                 440                 445

Glu Gln Thr Glu Gln Asp Glu Val Lys Gln Lys Leu Leu Gln Ala Leu
    450                 455                 460

Cys His Tyr Leu Arg Asn Leu
465                 470

<210> SEQ ID NO 2
<211> LENGTH: 497
<212> TYPE: PRT
<213> ORGANISM: Halamonas sp

<400> SEQUENCE: 2

Met Ala Ser Pro Asn Ala Ala Pro Ala Ser Phe Leu Trp His Asp Tyr
1               5                   10                  15

Glu Thr Phe Gly Ala Asp Pro Arg Arg Asp Arg Pro Ala Gln Phe Ala
            20                  25                  30

Ala Leu Arg Thr Asp Ala Glu Leu Asn Glu Ile Gly Glu Pro Ile Glu
        35                  40                  45

Leu Tyr Cys Lys Pro Ala Asp Asp Tyr Leu Pro His Pro Ala Ala Cys
    50                  55                  60

Leu Ile Thr Gly Ile Thr Pro Gln Lys Ala Gln Arg His Gly Leu Pro
65                  70                  75                  80

Glu Ala Glu Phe Ala Gly Glu Ile Gln Arg His Met Ser Glu Pro Gly
                85                  90                  95

Thr Cys Val Val Gly Tyr Asn Ser Leu Arg Phe Asp Asp Glu Val Ser
            100                 105                 110

Arg His Leu Phe Tyr Arg Asn Leu Leu Asp Pro Tyr Ser Arg Glu Trp
        115                 120                 125

Gln Asn Gly Asn Ser Arg Trp Asp Leu Ile Asp Ile Val Arg Ala Phe
    130                 135                 140

Tyr Ala Leu Arg Pro Asp Gly Ile Glu Trp Pro Leu Arg Glu Asp Gly
145                 150                 155                 160

Ala Pro Ser Phe Lys Leu Glu His Leu Thr Ala Ala Asn Gly Ile Ala
                165                 170                 175

His Glu Gly Ala His Asp Ala Val Ala Asp Val Arg Ala Thr Ile Ala
            180                 185                 190

Leu Ala Arg Leu Leu Lys Val Arg Asn Ala Lys Leu Phe Asp Tyr Leu
        195                 200                 205

Leu Gly Leu Arg Gly Lys Arg Ala Val Ala Lys Gln Leu Asp Leu Pro
    210                 215                 220

Asn Ala Lys Pro Leu Leu His Ile Ser Arg Arg Tyr Pro Ala Ser Arg
225                 230                 235                 240
```

Gly Cys Ser Ala Leu Val Met Pro Leu Ala Glu His Pro Thr Asn Pro
            245                 250                 255

Asn Gly Val Ile Val Tyr Asp Leu Ser Val Asp Pro Ser Asp Met Leu
        260                 265                 270

Ser Met Ser Ala Glu Gln Ile Arg Glu Arg Val Phe Val Ser Gln Gln
    275                 280                 285

Asp Leu Ala Glu Gly Glu Ala Arg Ile Pro Leu Lys Ile Ile His Ile
290                 295                 300

Asn Arg Cys Pro Val Val Phe Pro Ala Ser Ala Leu Lys Asp Val Glu
305                 310                 315                 320

Gly Pro His Gln Gly Glu Tyr Gly Thr Ile Val Ala Arg Leu Gly Leu
                325                 330                 335

Asp Val Ala Ala Cys Arg Gln His Trp Lys Thr Leu Arg Asp Ala Ser
            340                 345                 350

Gly Val Ala Ala Lys Val Ala Glu Val Phe Ser Ala Gly Tyr Asp Asp
        355                 360                 365

Val Pro Gln Asp Pro Asp Leu Met Leu Tyr Ser Gly Ser Phe Phe Ser
    370                 375                 380

Ala Ala Asp Arg Gln Gln Met Glu Arg Val Arg Glu Met Glu Pro Trp
385                 390                 395                 400

Asp Leu Val Gly Gln Arg Phe Ala Phe Gln Asp Pro Arg Leu Glu Glu
                405                 410                 415

Met Leu Phe Arg Phe Arg Ala Arg Ser Tyr Pro Asp Thr Leu Glu Gly
            420                 425                 430

Glu Glu Arg Glu Gln Trp Glu Ala Phe Arg Trp Met Arg Ile Asn Asp
        435                 440                 445

Pro Ala Leu Ala Gly Phe Thr Leu Lys Ala Phe Ala Arg Glu Ile Glu
    450                 455                 460

Gln Tyr Asn Gln Gln Thr Leu Thr Asp Arg Gly Arg Gln Val Leu Glu
465                 470                 475                 480

Glu Leu Val Met Phe Val Glu Ala Met Met Pro Ala Gln Ala Phe Asp
                485                 490                 495

Ala

<210> SEQ ID NO 3
<211> LENGTH: 474
<212> TYPE: PRT
<213> ORGANISM: Vibrio wodanis

<400> SEQUENCE: 3

Met Pro Gln Asp Asn Ala Pro Ser Phe Phe Phe Phe Asp Tyr Glu Thr
1               5                   10                  15

Trp Gly Thr Ser Pro Ser Leu Asp Arg Pro Cys Gln Phe Ala Gly Val
            20                  25                  30

Arg Thr Asp Glu Asp Phe Asn Ile Ile Gly Glu Pro Leu Val Ile Tyr
        35                  40                  45

Cys Arg Pro Pro Ile Asp Tyr Leu Pro Ser Pro Glu Ala Cys Leu Ile
    50                  55                  60

Thr Gly Ile Thr Pro Gln Thr Ala Val Asn Lys Gly Leu Ser Glu Pro
65                  70                  75                  80

Glu Phe Ile Thr Gln Ile His Asn Glu Leu Ser Lys Pro Asn Thr Cys
                85                  90                  95

Ser Leu Gly Tyr Asn Asn Ile Arg Phe Asp Asp Glu Val Ser Arg Tyr
            100                 105                 110

Thr Leu Tyr Arg Asn Phe Phe Glu Pro Tyr Gly Trp Ser Trp Gln Asn
            115                 120                 125

Gly Asn Ser Arg Trp Asp Leu Leu Asp Val Met Arg Ala Val Tyr Ala
        130                 135                 140

Leu Arg Pro Glu Gly Ile Lys Trp Pro Lys Asp Glu Glu Gly Lys Pro
145                 150                 155                 160

Ser Phe Arg Leu Glu Lys Leu Ser Gln Ala Asn Gly Ile Glu His Glu
                165                 170                 175

Asn Ala His Asp Ala Met Ala Asp Val Ile Ala Thr Ile Glu Leu Ala
            180                 185                 190

Lys Val Val Lys Lys Ala Gln Pro Lys Met Phe Asn Tyr Leu Leu Ser
        195                 200                 205

Met Arg His Lys Lys Lys Ala Ala Thr Leu Ile Asp Ile Val Glu Met
210                 215                 220

Thr Pro Leu Met His Val Ser Gly Met Phe Gly Val Asp Arg Gly Asn
225                 230                 235                 240

Ile Ser Trp Ile Val Pro Val Ala Trp His Pro Thr Asn Asn Asn Ala
                245                 250                 255

Val Ile Thr Ile Asp Leu Ala Leu Asp Pro Ser Val Phe Leu Glu Leu
            260                 265                 270

Asp Ala Glu Gln Leu His Gln Arg Met Tyr Thr Lys Arg Ala Asp Leu
        275                 280                 285

Ala Pro Asp Glu Leu Pro Val Pro Val Lys Leu Val His Leu Asn Lys
    290                 295                 300

Cys Pro Ile Leu Ala Pro Ala Lys Thr Leu Thr Ala Glu Asn Ala Glu
305                 310                 315                 320

Asn Leu Asn Val Asp Arg Ala Ala Cys Leu Lys Asn Leu Lys Val Ile
                325                 330                 335

Arg Asp Asn Pro Glu Ile Arg Gln Lys Leu Ile Ala Leu Tyr Ser Ile
            340                 345                 350

Glu Pro Asn Tyr Glu Lys Ser Thr Asn Val Asp Thr Leu Leu Tyr Asp
        355                 360                 365

Gly Phe Phe Ser His Ala Asp Lys Thr Thr Ile Asp Ile Ile Arg Gln
    370                 375                 380

Ser Thr Pro Glu Gln Leu Ile Asp Phe Glu Pro Asn Val Ser Asp Pro
385                 390                 395                 400

Arg Ile Lys Pro Leu Leu Phe Arg Tyr Arg Ala Arg Asn Phe Pro His
                405                 410                 415

Thr Leu Asn Glu Thr Glu Gln Leu Lys Trp Gln Ser His Leu Gln Asp
            420                 425                 430

Tyr Phe Gln Thr His Leu Pro Glu Tyr Glu Ser Ser Phe Glu Asn Leu
        435                 440                 445

Tyr Leu Glu Ser Glu Gly Asn Glu Lys Lys Thr Ala Ile Leu Arg Ala
    450                 455                 460

Val Tyr Asn Tyr Val Gln Gln Leu Val Ser
465                 470

<210> SEQ ID NO 4
<211> LENGTH: 476
<212> TYPE: PRT
<213> ORGANISM: Psychromonas sp

<400> SEQUENCE: 4

Met Asn Gln Glu Ser Pro Ser Leu Leu Trp His Asp Tyr Glu Thr Phe

```
1               5                   10                  15
Gly Leu Asn Pro Gly Thr Asp Arg Pro Ser Gln Phe Ala Gly Ile Arg
                20                  25                  30
Thr Asp Leu Asp Leu Asn Ile Ile Ser Glu Pro Tyr Gln Trp Tyr Cys
                35                  40                  45
Arg Pro Pro Asn Asp Tyr Leu Pro Ala Pro Glu Ala Cys Leu Val Thr
50                  55                  60
Gly Ile Thr Pro Gln Tyr Ala Leu Gln His Gly Glu Phe Glu Asn Gln
65                  70                  75                  80
Phe Ile Phe Asn Ile Leu Gln Gln Phe Gln Gln Asn Thr Cys Val
                85                  90                  95
Val Gly Tyr Asn Asn Ile Arg Phe Asp Asp Glu Val Thr Arg Phe Thr
                100                 105                 110
Leu Tyr Arg Asn Phe His Asp Pro Tyr Gln Arg Glu Trp Gln Asn Gly
                115                 120                 125
Cys Ser Arg Trp Asp Ile Ile Asp Met Val Arg Ala Cys Tyr Ala Leu
                130                 135                 140
Arg Pro Glu Gly Ile Glu Trp Val Phe Asp Glu Asn Asp Ala Pro Ser
145                 150                 155                 160
Phe Lys Leu Glu Leu Leu Thr Lys Ala Asn Asp Ile Val His Gln Gln
                165                 170                 175
Ala His Asp Ala Met Ser Asp Val Tyr Ala Thr Ile Ala Met Ala Lys
                180                 185                 190
Leu Ile Lys Thr Ala His Pro Lys Leu Tyr Asp Tyr Cys Tyr Ser Leu
                195                 200                 205
Arg Gln Lys Asn Lys Val Leu Asn Glu Leu Lys Leu Gly Thr Phe Lys
                210                 215                 220
Pro Leu Val His Ile Ser Gly Met Phe Ser Ala Met Gln Gly Cys Cys
225                 230                 235                 240
Ser Tyr Ile Leu Pro Ile Ala Gln His Pro Ser Asn Asn Ala Val
                245                 250                 255
Ile Val Leu Asp Leu Asn Lys Asp Ile Ser Gln Leu Leu Ser Leu Ser
                260                 265                 270
Val Glu Asp Ile Gln Ser Tyr Leu Tyr Thr Ala Thr Asp Asn Leu Pro
                275                 280                 285
Glu Gly Ile Asn Arg Pro Pro Ile Lys Leu Ile His Ile Asn Lys Cys
                290                 295                 300
Pro Ile Val Ala Ser Ala Lys Thr Leu Ser Ala Glu Arg Ala Lys Glu
305                 310                 315                 320
Leu Gly Val Asp Ala Lys Gln Cys Arg Gln Ser Met Asp Thr Phe Ser
                325                 330                 335
Glu Asn Lys His Leu Val Glu Lys Leu Ile Ala Val Phe Asp Thr Glu
                340                 345                 350
Ser Lys Ser Ser Lys Glu Gln Gln Pro Glu Gln Lys Leu Tyr Ser Gly
                355                 360                 365
Gly Phe Pro Thr Ala Asn Asp Lys Asn Gln Ala Lys Ala Ile Thr Ser
                370                 375                 380
Leu Ser Pro Gln Gln Ile Ala Asn Tyr Gln Val Thr Phe Asp Asp Pro
385                 390                 395                 400
Asn Phe Asp Asn Leu Trp Trp Arg Tyr Lys Ala Arg Asn Tyr Pro Gln
                405                 410                 415
Met Leu Ser Leu Glu Glu Gln Gln Lys Trp Gly Arg His Arg Glu Ala
                420                 425                 430
```

```
Tyr Leu Ile Glu His Val Asp Asn Tyr Val Ala Arg Leu Glu Met Leu
        435                 440                 445

Val Ile Glu His Gln His Ser Pro Glu Lys Ile Glu Val Leu Gln Lys
    450                 455                 460

Leu Gly His Tyr Leu Glu Phe Leu Thr Gly Asn Thr
465                 470                 475

<210> SEQ ID NO 5
<211> LENGTH: 480
<212> TYPE: PRT
<213> ORGANISM: Moritella viscosa

<400> SEQUENCE: 5

Met Asp Asn Asn Ser Asn Lys Thr Ala Thr Asp Leu Pro Thr Phe Tyr
1               5                   10                  15

Trp His Asp Tyr Glu Thr Phe Gly Leu Ser Pro Ser Leu Asp Arg Pro
            20                  25                  30

Ser Gln Phe Ala Gly Ile Arg Thr Asp Met Asp Phe Asn Val Ile Gly
        35                  40                  45

Glu Pro Asp Met Phe Tyr Cys Arg Gln Ser Asp Asp Tyr Leu Pro Ser
    50                  55                  60

Pro Glu Ala Ala Met Ile Thr Gly Ile Thr Pro Gln Lys Thr Gln Ala
65                  70                  75                  80

Glu Gly Val Ser Glu Ala Glu Phe Ser Lys Arg Ile Glu Ala Gln Phe
                85                  90                  95

Ser Gln Lys Asn Thr Cys Ile Ile Gly Tyr Asn Asn Ile Arg Phe Asp
            100                 105                 110

Asp Glu Val Thr Arg Asn Ile Phe Tyr Arg Asn Phe Tyr Asp Pro Tyr
        115                 120                 125

Ala His Thr Trp Lys Asp Gly Asn Ser Arg Trp Asp Ile Ile Asp Leu
    130                 135                 140

Met Arg Ala Cys Tyr Ala Leu Arg Pro Glu Gly Ile Val Trp Pro Glu
145                 150                 155                 160

Asn Asp Asp Gly Leu Pro Ser Met Arg Leu Glu Leu Leu Thr Ala Ala
                165                 170                 175

Asn Gly Ile Glu His Ala Asn Ala His Asp Ala Thr Ser Asp Val Tyr
            180                 185                 190

Ala Thr Ile Ala Met Ala Lys Leu Val Lys Glu Lys Gln Pro Lys Leu
        195                 200                 205

Phe Asp Phe Leu Phe Asn Leu Arg Ser Lys Arg Lys Val Glu Ser Leu
    210                 215                 220

Val Asp Ile Ile Asn Met Thr Pro Leu Val His Val Ser Gly Met Phe
225                 230                 235                 240

Gly Ala Asp Arg Gly Phe Thr Ser Trp Val Val Pro Leu Ala Trp His
                245                 250                 255

Pro Thr Asn Asn Asn Ala Val Ile Val Ala Asp Leu Ala Gln Asp Ile
            260                 265                 270

Thr Pro Leu Leu Glu Leu Ser Ala Asp Glu Leu Arg Glu Arg Leu Tyr
        275                 280                 285

Thr Pro Lys Lys Asp Leu Gly Asp Leu Thr Pro Ile Pro Leu Lys Leu
    290                 295                 300

Ile His Ile Asn Lys Cys Pro Val Leu Ala Pro Ala Lys Thr Leu Leu
305                 310                 315                 320

Pro Glu Asn Ala Glu Arg Leu Gly Ile Asp Arg Ser Ala Cys Leu Ala
```

|     |     |     |     |     | 325 |     |     |     | 330 |     |     |     |     | 335 |
| --- | --- | --- | --- | --- | --- | --- | --- | --- | --- | --- | --- | --- | --- | --- |
| Asn | Leu | Lys | Arg | Leu | Lys | Glu | Ser | Ala | Thr | Leu | Arg | Glu | Asn | Val | Val |
|     |     |     |     | 340 |     |     |     |     | 345 |     |     |     | 350 |     |

Gly Val Tyr Gln Val Glu Arg Glu Tyr Pro Lys Ser Thr Asn Val Asp
        355                 360                 365

Ala Met Ile Tyr Asp Gly Phe Phe Ser Ala Gly Asp Lys Ala Asn Phe
    370                 375                 380

Glu Ile Leu Arg Glu Thr Ala Pro Glu Gln Leu Thr Gly Leu Gln Leu
385                 390                 395                 400

Lys Val Ser Asp Ser Arg Phe Asn Glu Leu Phe Phe Arg Tyr Arg Ala
                405                 410                 415

Arg Asn Phe Pro His Leu Leu Ser Met Pro Glu Gln Gln Lys Trp Leu
                420                 425                 430

Asp His Cys Arg Thr Val Leu Glu Asp Ser Ala Pro Ala Tyr Phe Ala
                435                 440                 445

Arg Leu Asp Ala Leu Ala Ile Glu Asn Ser His Asp Glu Arg Lys Met
450                 455                 460

Lys Leu Leu Gln Gln Leu Tyr Leu Tyr Gly Gln Lys Ile Ile Gly Ala
465                 470                 475                 480

<210> SEQ ID NO 6
<211> LENGTH: 1416
<212> TYPE: DNA
<213> ORGANISM: Shewanella sp.

<400> SEQUENCE: 6

| atgaacaaca | ctaagaaaca | gccaacttta | ttttggcacg | attatgaaac | atttggtgct | 60 |
| --- | --- | --- | --- | --- | --- | --- |
| aatccagcca | agataggcc | atcgcagttt | gctggtgtgc | gtaccgacat | ggatctcaat | 120 |
| atcattgctg | agcctgtcac | attttactgt | aaagtcgcga | atgactacct | gccctcacct | 180 |
| gaagctattt | taattacagg | tataaccaca | cagcttgcta | accttaaagg | gatgcctgaa | 240 |
| gctgagttta | tggcacaaat | ccaccagttg | tttagccaag | aaaatacctg | tgttgtgggt | 300 |
| tacaactcaa | ttagatttga | tgatgaagtc | tcccgctatg | gcttttaccg | taactttttt | 360 |
| gacccgtatg | ctagagaatg | gaaaaacggt | aatagtcgct | gggatatcat | tgatttagta | 420 |
| cgtgcttgtt | atgcctttag | gcccgatgga | ataaactggc | cacaaaaaga | gatggctct | 480 |
| ccaagtttta | aactcgaaca | cttaaccgtt | gccaatggcc | ttagccatga | aaaagcccac | 540 |
| gatgctatgt | ctgatgtgta | tgccactatt | gcgatggcta | agcttatcaa | atcagtgcag | 600 |
| cctaaattgt | ttgaatatta | cttcaatctg | cgccgaaaac | aggaagtttc | gaagctaatc | 660 |
| gacgtactag | aaatgaaacc | gttagtgcat | gtaagttcaa | agattagcgc | gctaaatggc | 720 |
| tgtaccacat | taatcgcgcc | gctggccttt | cacacgacta | taaaaaatgc | ggttatctgt | 780 |
| gtcaatttag | ccatggatgt | cacgccgctc | attgagttga | ccgccgagca | attcgagag | 840 |
| cgcatgtaca | aaggcgtga | tgatttagcg | gaagatgagt | tacctattgg | catcaaacaa | 900 |
| atccatatca | acaaagtcc | atttattgcc | ggtgctaaat | cattaaccga | tgaaaatgcc | 960 |
| gctcgtcttg | atattgataa | agcatttgca | agagatcaat | ataagcggct | tagacagcac | 1020 |
| ccagagatac | gagaaaagct | cgttgcggtg | tttgacatcg | agtccgatcg | tatcattacc | 1080 |
| gatcccgatc | ttcagcttta | tagcggtggc | ttttttagcc | atgcggataa | agcaaaaatg | 1140 |
| gagatgatcc | gtaataccaa | acctattaat | ttagccgcac | tggagctgtc | atttgacgat | 1200 |
| gagcgcttac | cagaaatgtt | gtatcgatat | agagcacgta | attatcctga | acactggat | 1260 |

| | |
|---|---|
| gaatctgaga gcattcgttg gcgtgaattc tgtcaatcaa ggctcaatga tcctgattac | 1320 |
| atgataaaac ttgaaaacat tattgaacaa accgagcaag atgaagtaaa gcaaaaatta | 1380 |
| ttacaggctt tgtgtcatta tcttagaaat ctttag | 1416 |

<210> SEQ ID NO 7
<211> LENGTH: 1494
<212> TYPE: DNA
<213> ORGANISM: Halomonas sp.

<400> SEQUENCE: 7

| | |
|---|---|
| atggcatcac ccaatgctgc ccctgccagt tttctctggc atgattatga aaccttcggg | 60 |
| gctgacccgc gccgcgatcg gcccgctcag ttcgctgcac tgcgcacgga tgcagaactg | 120 |
| aacgagatcg gtgagcccat cgagctctac tgcaaacccg ccgatgacta cctgcctcat | 180 |
| cctgctgcct gtttgatcac cggtattacc cctcaaaaag cccagcgcca tggtctcccc | 240 |
| gaagcagagt tcgcgggtga gattcagcgc cacatgagcg agccgggtac ctgcgtagtg | 300 |
| ggctacaaca gcctgcgttt tgatgacgaa gtttcgcgcc acctgttta ccgcaatttg | 360 |
| cttgacccct tatcccgcga gtggcaaaac ggcaattccc gctgggattt aatcgatatt | 420 |
| gtgcgcgcct tttatgcgct cgcccggat ggcattgaat ggccgctgcg cgaagacggt | 480 |
| gcacccagct ttaagctcga gcacttaact gccgccaacg gcattgccca tgagggtgcc | 540 |
| cacgatgcgg tggcagatgt ccgcgctact atcgccttgg cgcggttgct caaagtgcgc | 600 |
| aatgccaagc tgtttgacta tctgctcggc ctgcgcggta agcgcgcggt ggccaagcag | 660 |
| ctcgacttgc ccaacgccaa accgctgctg catatctccc gccgttatcc tgctagccgg | 720 |
| ggctgtagtg cactagtcat gccgctggcc gagcacccga caaaccctaa tggggtgatt | 780 |
| gtttacgatt tgagcgttga tcccagcgat atgctgagca tgtcggcgga gcaaattcgt | 840 |
| gagcgggtgt ttgtcagtca gcaggatctc gccgaaggcg aggcgcgcat tccgctaaag | 900 |
| atcatccata tcaaccgctg cccagtggtg ttccccgcta gtgctttgaa agacgttgag | 960 |
| gggcctcatc agggcgagta tggcaccatc gtcgcgcgct taggcttaga tgtggctgcc | 1020 |
| tgtcggcagc actggaaaac cctgcgcgat gccagcggtg tcgccgctaa ggtcgccgag | 1080 |
| gtgtttagtg ccggttacga cgatgtaccc caagaccctg atctaatgct ctattcgggc | 1140 |
| agtttcttct ccgctgctga ccgtcagcag atggagcggg tgcagagagat ggaaccgtgg | 1200 |
| gacctggtcg gtcagcgctt tgcgtttcag gatccgcgtt tggaagagat gctgtttcgc | 1260 |
| tttcgtgcgc gcagttaccc cgacacgttg gaaggcgaag agcgcgagca gtgggaggcg | 1320 |
| tttcgctgga tgcggatcaa tgacccggcc ttggcgggct ttacgcttaa ggcgtttgcg | 1380 |
| cgggaaatcg agcagtacaa tcagcaaacc ctcactgatc gcgagcggca ggttctggaa | 1440 |
| gagctggtga tgttcgtgga agccatgatg ccggcccagg catttgatgc ctga | 1494 |

<210> SEQ ID NO 8
<211> LENGTH: 1425
<212> TYPE: DNA
<213> ORGANISM: Vibrio wodanis

<400> SEQUENCE: 8

| | |
|---|---|
| atgccgcagg ataacgcacc aagtttcttc tttttttgatt atgaaacatg gggaactagc | 60 |
| ccatctctcg atcgcccatg ccaatttgct ggagttcgta ccgatgaaga tttcaatatc | 120 |
| attggtgagc cattagttat ttactgtcgc cctccaattg attatttacc ttctcctgaa | 180 |
| gcctgtttaa ttactggcat cacgccacaa actgcggtaa ataaaggcct gtctgagcct | 240 |

```
gagttcatta ctcaaatcca taacgaatta tcaaaaccaa atacttgctc gctaggctat        300
aacaacattc gttttgatga tgaagtttct cgctacacct tatatcgtaa cttctttgaa        360
ccgtatggct ggagctggca aaacggcaac tcgcgttggg atctacttga tgtaatgcgt        420
gctgtgtatg ctctgcgtcc tgaaggcatt aaatggccaa agacgaaga aggcaaacca         480 agctttagat tagaaaaact ctcgcaagca aatggcattg aacatgaaaa tgcccacgat        540
gcgatggccg atgttattgc caccatcgag ttagctaaag tcgttaaaaa agcacaacct        600
aaaatgttta actacctgct ttctatgcgt cataaaaaga aagcggcaac gttaatcgat        660
attgttgaaa tgcaccgtt aatgcacgtg tctggtatgt ttggcgtaga tagaggcaat         720
attagttgga ttgtgcctgt tgcttggcat cctaccaata acaacgccgt cattacgatt        780
gatttagcgt tagacccaag tgtgttccta gaattagatg cagagcaatt acatcaacgc       840
atgtatacca aacgtgctga tctagcccct gacgaattgc ctgttcctgt aaaattagta       900
catttaaaca gtgccctat tcttgcgcct gctaaaacat gacggctga gaatgctgaa          960 aatctaaatg tggacagagc cgcctgttta aaaaatctta aagtgatccg tgataaccct      1020
gagatcagac aaaagctaat tgcgctttac agcattgagc ctaattatga gaaatcaacc      1080
aatgtagata ccccttctata tgatggtttc ttctctcatg ctgataaaac gacgattgat     1140
attatccgtc agtcaacgcc tgagcagctt atcgattttg aaccaaatgt cagtgaccca     1200
cgcattaaac ctctattatt ccgctatcgt gcgcgcaatt tcccgcatac gcttaatgag     1260
acagagcaac tgaaatggca atcacattta caagattact tccaaactca tttacctgaa    1320
tacgaatcaa gctttgagaa tttatatctt gaatctgaag gcaatgagaa aaagactgcg     1380
atccttcgcg ccgtttataa ttacgtacaa cagttagtat catga                     1425
```

<210> SEQ ID NO 9
<211> LENGTH: 1431
<212> TYPE: DNA
<213> ORGANISM: Psychromonas sp

<400> SEQUENCE: 9

```
atgaatcaag aatccccaag ccttctttgg cacgattatg aaaccttcgg gttaaaccca         60
ggaacggatc gcccttctca gtttgcaggc attcgtactg atcttgattt aaatatcatt        120
tctgagcctt atcaatggta ctgcagacca cccaacgatt atttacctgc tcctgaagcg        180
tgtttagtaa cgggaataac accacaatat gcgttgcaac atggtgaatt tgaaaaccaa        240
tttatattta atatattgca gcaattccaa cagcaaaaca cgtgcgttgt tgggtataac        300 atatattcgct ttgatgatga agtcacacgc tttactttgt atcgtaattt tcatgaccct      360
tatcaaagag aatggcaaaa tggctgctct cgctgggaca ttattgacat ggttcgcgct       420
tgctatgcac tcagaccaga aggtattgaa tgggtatttg atgaaaatga tgcgccaagt      480
tttaaacttg agttattaac taagctaat gacattgttc atcagcaagc acatgatgcg       540
atgtcggatg tttatgccac tatcgccatg gcaaaactaa ttaagacagc catccaaag      600 ctatatgact attgttatag tttgagacaa aaaaataaag tattaaacga actgaagctt     660
ggtacattta aacctttagt tcatatctct ggtatgtttt ctgcgatgca aggctgttgt      720
tcttatattt tacctatcgc acaacaccca gtaacaata atgcagtgat agtgcttgat       780
ttaaataaag atatttcaca acttttatcg ttgagtgttg aagatatcca atcttactta     840
tataccgcta cggataattt accagagggt attaatagac cccctattaa attaatccat    900
```

```
attaataaat gccctatcgt agcaagtgca aaaacattaa gtgcagagag agcaaaagaa      960
ttaggggttg atgcaaaaca atgccgtcaa tcaatggata cgttctcaga aaataaacat     1020
ttggttgaga aactgattgc agtgtttgac actgaatcca aaagcagcaa ggaacaacaa     1080
ccagaacaaa aattgtattc tggcggtttc cctactgcta acgacaaaaa tcaagcaaaa     1140
gcgatcacca gtttgtcgcc acaacaaatt gctaattacc aagttacttt tgatgatcct     1200
aattttgata tttatggtg gcgatacaaa gcaagaaatt atccgcaaat gttatcactt      1260
gaagagcaac aaaaatgggg tagacacaga gaagcttatc ttattgaaca tgtagataat     1320
tatgttgcac gcttagaaat gctagtgatt gagcatcaac atagcccaga aaagatcgaa     1380
gtattgcaaa aactgggaca ttacttagag tttttgacag ggaatacata a              1431

<210> SEQ ID NO 10
<211> LENGTH: 1443
<212> TYPE: DNA
<213> ORGANISM: Moritella viscosa

<400> SEQUENCE: 10
atggataaca attcgaacaa aacagcaaca gatctgccca cttttttactg gcatgattat   60
gagacttttg gcttaagtcc gtcactggat cgcccttctc aatttgctgg tattcgcacc  120
gacatggact ttaatgtgat cggcgaacca gatatgtttt actgccgcca atcagatgat  180
taccttcctt cgccagaagc tgccatgatt actgggataa cacctcaaaa gacccaagca  240
gaaggtgtaa gtgaagcaga gttcagtaaa cgtattgaag cgcaattcag tcaaaaaaac  300
acctgtatca ttggttataa caacattcgc tttgatgatg aagtaacacg taatatcttc  360
taccgtaatt tctacgaccc atacgcacac acctggaaag atggtaattc gcgctgggat  420
attattgact tgatgcgcgc ttgttatgct ctgcgccctg aaggtattgt atggccagaa  480
aatgatgatg gtctaccaag tatgcgtctt gaattattaa ccgccgcaaa tggcattgag  540
cacgctaatg cccatgatgc tacttctgat gtatatgcaa ctatcgcgat ggcgaagcta  600
gttaaagaaa acaacctaa gctgtttgat ttcttatta acctacgtag caaacgtaaa   660
gttgaatcct tggttgatat catcaacatg acaccattag tgcatgtaag cggcatgttt  720
ggtgcagatc gcggattcac aagctgggta gtgccactgg cttggcaccc aaccaacaac  780
aacgctgtga ttgtagctga cttagcccaa gacattacgc cattattaga attgagcgcg  840
gatgaactgc gcgaacgttt atatacgcca aagaaagatc tcggtgactt aacccctatc  900
ccgctgaaac ttattcatat caacaagtgt ccagtactcg cgccagcgaa aactctatta  960
cctgaaaacg cagaacgttt agggattgat cgcagcgcct gcctcgcaaa cctaaaacgt  1020
ttaaaagaaa gcgcaacact gcgtgaaaat gttgtgggtg tttatcaagt agaacgtgaa  1080
tatccaaaat caaccaatgt ggatgcaatg atctacgatg gtttctttag tgcaggtgat  1140
aaagcaaact ttgaaatact acgtgaaaca gcaccagagc aacttacagg actgcaactg  1200
aaagtcagtg attcgcgttt taatgaatta ttcttccgct atcgagcacg taacttcccg  1260
catttattat caatgcctga gcaacaaaaa tggcttgacc actgccgaac tgtgctagaa  1320
gacagtgccc cagcctattt tgcacgttta gatgcattag cgatcgaaaa cagccatgac  1380
gagcgaaaaa tgaaactact tcaacagtta tacctttatg gtcaaaaaat aattggcgca  1440
taa                                                                 1443

<210> SEQ ID NO 11
<211> LENGTH: 480
```

<212> TYPE: PRT
<213> ORGANISM: Artifical Sequence
<220> FEATURE:
<223> OTHER INFORMATION: His tagged Schwanella sp exonuclease

<400> SEQUENCE: 11

Met Asn Asn Thr Lys Lys Gln Pro Thr Leu Phe Trp His Asp Tyr Glu
1               5                   10                  15

Thr Phe Gly Ala Asn Pro Ala Lys Asp Arg Pro Ser Gln Phe Ala Gly
            20                  25                  30

Val Arg Thr Asp Met Asp Leu Asn Ile Ile Ala Glu Pro Val Thr Phe
        35                  40                  45

Tyr Cys Lys Val Ala Asn Asp Tyr Leu Pro Ser Pro Glu Ala Ile Leu
    50                  55                  60

Ile Thr Gly Ile Thr Pro Gln Leu Ala Asn Leu Lys Gly Met Pro Glu
65                  70                  75                  80

Ala Glu Phe Met Ala Gln Ile His Gln Leu Phe Ser Gln Glu Asn Thr
                85                  90                  95

Cys Val Val Gly Tyr Asn Ser Ile Arg Phe Asp Asp Glu Val Ser Arg
            100                 105                 110

Tyr Gly Phe Tyr Arg Asn Phe Phe Asp Pro Tyr Ala Arg Glu Trp Lys
        115                 120                 125

Asn Gly Asn Ser Arg Trp Asp Ile Ile Asp Leu Val Arg Ala Cys Tyr
    130                 135                 140

Ala Phe Arg Pro Asp Gly Ile Asn Trp Pro Gln Lys Glu Asp Gly Ser
145                 150                 155                 160

Pro Ser Phe Lys Leu Glu His Leu Thr Val Ala Asn Gly Leu Ser His
                165                 170                 175

Glu Lys Ala His Asp Ala Met Ser Asp Val Tyr Ala Thr Ile Ala Met
            180                 185                 190

Ala Lys Leu Ile Lys Ser Val Gln Pro Lys Leu Phe Glu Tyr Tyr Phe
        195                 200                 205

Asn Leu Arg Arg Lys Gln Glu Val Ser Lys Leu Ile Asp Val Leu Glu
    210                 215                 220

Met Lys Pro Leu Val His Val Ser Ser Lys Ile Ser Ala Leu Asn Gly
225                 230                 235                 240

Cys Thr Thr Leu Ile Ala Pro Leu Ala Phe His Thr Thr Asn Lys Asn
                245                 250                 255

Ala Val Ile Cys Val Asn Leu Ala Met Asp Val Thr Pro Leu Ile Glu
            260                 265                 270

Leu Thr Ala Glu Gln Ile Arg Glu Arg Met Tyr Thr Arg Arg Asp Asp
        275                 280                 285

Leu Ala Glu Asp Glu Leu Pro Ile Gly Ile Lys Gln Ile His Ile Asn
    290                 295                 300

Lys Ser Pro Phe Ile Ala Gly Ala Lys Ser Leu Thr Asp Glu Asn Ala
305                 310                 315                 320

Ala Arg Leu Asp Ile Asp Lys Ala Phe Ala Arg Asp Gln Tyr Lys Arg
                325                 330                 335

Leu Arg Gln His Pro Glu Ile Arg Glu Lys Leu Val Ala Val Phe Asp
            340                 345                 350

Ile Glu Ser Asp Arg Ile Ile Thr Asp Pro Asp Leu Gln Leu Tyr Ser
        355                 360                 365

Gly Gly Phe Phe Ser His Ala Asp Lys Ala Lys Met Glu Met Ile Arg
    370                 375                 380

```
Asn Thr Lys Pro Ile Asn Leu Ala Ala Leu Glu Leu Ser Phe Asp Asp
385                 390                 395                 400

Glu Arg Leu Pro Glu Met Leu Tyr Arg Tyr Arg Ala Arg Asn Tyr Pro
            405                 410                 415

Glu Thr Leu Asp Glu Ser Glu Ser Ile Arg Trp Arg Glu Phe Cys Gln
            420                 425                 430

Ser Arg Leu Asn Asp Pro Asp Tyr Met Ile Lys Leu Glu Asn Ile Ile
        435                 440                 445

Glu Gln Thr Glu Gln Asp Glu Val Lys Gln Lys Leu Leu Gln Ala Leu
        450                 455                 460

Cys His Tyr Leu Arg Asn Leu Ser Ala Gly His His His His His His
465                 470                 475                 480

<210> SEQ ID NO 12
<211> LENGTH: 506
<212> TYPE: PRT
<213> ORGANISM: Artificial sequence
<220> FEATURE:
<223> OTHER INFORMATION: His tagged Halomonas sp exonuclease

<400> SEQUENCE: 12

Met Ala Ser Pro Asn Ala Ala Pro Ala Ser Phe Leu Trp His Asp Tyr
1               5                   10                  15

Glu Thr Phe Gly Ala Asp Pro Arg Arg Asp Arg Pro Ala Gln Phe Ala
            20                  25                  30

Ala Leu Arg Thr Asp Ala Glu Leu Asn Glu Ile Gly Glu Pro Ile Glu
        35                  40                  45

Leu Tyr Cys Lys Pro Ala Asp Asp Tyr Leu Pro His Pro Ala Ala Cys
    50                  55                  60

Leu Ile Thr Gly Ile Thr Pro Gln Lys Ala Gln Arg His Gly Leu Pro
65                  70                  75                  80

Glu Ala Glu Phe Ala Gly Glu Ile Gln Arg His Met Ser Glu Pro Gly
            85                  90                  95

Thr Cys Val Val Gly Tyr Asn Ser Leu Arg Phe Asp Asp Glu Val Ser
        100                 105                 110

Arg His Leu Phe Tyr Arg Asn Leu Leu Asp Pro Tyr Ser Arg Glu Trp
    115                 120                 125

Gln Asn Gly Asn Ser Arg Trp Asp Leu Ile Asp Ile Val Arg Ala Phe
130                 135                 140

Tyr Ala Leu Arg Pro Asp Gly Ile Glu Trp Pro Leu Arg Glu Asp Gly
145                 150                 155                 160

Ala Pro Ser Phe Lys Leu Glu His Leu Thr Ala Ala Asn Gly Ile Ala
            165                 170                 175

His Glu Gly Ala His Asp Ala Val Ala Asp Val Arg Ala Thr Ile Ala
        180                 185                 190

Leu Ala Arg Leu Leu Lys Val Arg Asn Ala Lys Leu Phe Asp Tyr Leu
    195                 200                 205

Leu Gly Leu Arg Gly Lys Arg Ala Val Ala Lys Gln Leu Asp Leu Pro
    210                 215                 220

Asn Ala Lys Pro Leu Leu His Ile Ser Arg Arg Tyr Pro Ala Ser Arg
225                 230                 235                 240

Gly Cys Ser Ala Leu Val Met Pro Leu Ala Glu His Pro Thr Asn Pro
            245                 250                 255

Asn Gly Val Ile Val Tyr Asp Leu Ser Val Asp Pro Ser Asp Met Leu
        260                 265                 270
```

```
Ser Met Ser Ala Glu Gln Ile Arg Glu Arg Val Phe Val Ser Gln Gln
            275                 280                 285

Asp Leu Ala Glu Gly Ala Arg Ile Pro Leu Lys Ile Ile His Ile
    290                 295                 300

Asn Arg Cys Pro Val Val Phe Pro Ala Ser Ala Leu Lys Asp Val Glu
305                 310                 315                 320

Gly Pro His Gln Gly Glu Tyr Gly Thr Ile Val Ala Arg Leu Gly Leu
                325                 330                 335

Asp Val Ala Ala Cys Arg Gln His Trp Lys Thr Leu Arg Asp Ala Ser
                340                 345                 350

Gly Val Ala Ala Lys Val Ala Glu Val Phe Ser Ala Gly Tyr Asp Asp
                355                 360                 365

Val Pro Gln Asp Pro Asp Leu Met Leu Tyr Ser Gly Ser Phe Phe Ser
    370                 375                 380

Ala Ala Asp Arg Gln Gln Met Glu Arg Val Arg Glu Met Glu Pro Trp
385                 390                 395                 400

Asp Leu Val Gly Gln Arg Phe Ala Phe Gln Asp Pro Arg Leu Glu Glu
                405                 410                 415

Met Leu Phe Arg Phe Arg Ala Arg Ser Tyr Pro Asp Thr Leu Glu Gly
                420                 425                 430

Glu Glu Arg Glu Gln Trp Glu Ala Phe Arg Trp Met Arg Ile Asn Asp
            435                 440                 445

Pro Ala Leu Ala Gly Phe Thr Leu Lys Ala Phe Ala Arg Glu Ile Glu
                450                 455                 460

Gln Tyr Asn Gln Gln Thr Leu Thr Asp Arg Glu Arg Gln Val Leu Glu
465                 470                 475                 480

Glu Leu Val Met Phe Val Glu Ala Met Met Pro Ala Gln Ala Phe Asp
                485                 490                 495

Ala Ser Ala Gly His His His His His His
                500                 505

<210> SEQ ID NO 13
<211> LENGTH: 483
<212> TYPE: PRT
<213> ORGANISM: Artificial Sequence
<220> FEATURE:
<223> OTHER INFORMATION: His tagged Vibrio wodanis sp exonuclease

<400> SEQUENCE: 13

Met Pro Gln Asp Asn Ala Pro Ser Phe Phe Phe Asp Tyr Glu Thr
1               5                   10                  15

Trp Gly Thr Ser Pro Ser Leu Asp Arg Pro Cys Gln Phe Ala Gly Val
                20                  25                  30

Arg Thr Asp Glu Asp Phe Asn Ile Ile Gly Glu Pro Leu Val Ile Tyr
            35                  40                  45

Cys Arg Pro Pro Ile Asp Tyr Leu Pro Ser Pro Glu Ala Cys Leu Ile
    50                  55                  60

Thr Gly Ile Thr Pro Gln Thr Ala Val Asn Lys Gly Leu Ser Glu Pro
65                  70                  75                  80

Glu Phe Ile Thr Gln Ile His Asn Glu Leu Ser Lys Pro Asn Thr Cys
                85                  90                  95

Ser Leu Gly Tyr Asn Asn Ile Arg Phe Asp Asp Glu Val Ser Arg Tyr
                100                 105                 110

Thr Leu Tyr Arg Asn Phe Phe Glu Pro Tyr Gly Trp Ser Trp Gln Asn
            115                 120                 125
```

Gly Asn Ser Arg Trp Asp Leu Leu Asp Val Met Arg Ala Val Tyr Ala
        130                 135                 140

Leu Arg Pro Glu Gly Ile Lys Trp Pro Lys Asp Glu Glu Gly Lys Pro
145                 150                 155                 160

Ser Phe Arg Leu Glu Lys Leu Ser Gln Ala Asn Gly Ile Glu His Glu
                165                 170                 175

Asn Ala His Asp Ala Met Ala Asp Val Ile Ala Thr Ile Glu Leu Ala
            180                 185                 190

Lys Val Val Lys Lys Ala Gln Pro Lys Met Phe Asn Tyr Leu Leu Ser
        195                 200                 205

Met Arg His Lys Lys Lys Ala Ala Thr Leu Ile Asp Ile Val Glu Met
210                 215                 220

Thr Pro Leu Met His Val Ser Gly Met Phe Gly Val Asp Arg Gly Asn
225                 230                 235                 240

Ile Ser Trp Ile Val Pro Val Ala Trp His Pro Thr Asn Asn Asn Ala
                245                 250                 255

Val Ile Thr Ile Asp Leu Ala Leu Asp Pro Ser Val Phe Leu Glu Leu
            260                 265                 270

Asp Ala Glu Gln Leu His Gln Arg Met Tyr Thr Lys Arg Ala Asp Leu
        275                 280                 285

Ala Pro Asp Glu Leu Pro Val Pro Val Lys Leu Val His Leu Asn Lys
290                 295                 300

Cys Pro Ile Leu Ala Pro Ala Lys Thr Leu Thr Ala Glu Asn Ala Glu
305                 310                 315                 320

Asn Leu Asn Val Asp Arg Ala Ala Cys Leu Lys Asn Leu Lys Val Ile
                325                 330                 335

Arg Asp Asn Pro Glu Ile Arg Gln Lys Leu Ile Ala Leu Tyr Ser Ile
            340                 345                 350

Glu Pro Asn Tyr Glu Lys Ser Thr Asn Val Asp Thr Leu Leu Tyr Asp
        355                 360                 365

Gly Phe Phe Ser His Ala Asp Lys Thr Thr Ile Asp Ile Ile Arg Gln
370                 375                 380

Ser Thr Pro Glu Gln Leu Ile Asp Phe Glu Pro Asn Val Ser Asp Pro
385                 390                 395                 400

Arg Ile Lys Pro Leu Leu Phe Arg Tyr Arg Ala Arg Asn Phe Pro His
                405                 410                 415

Thr Leu Asn Glu Thr Glu Gln Leu Lys Trp Gln Ser His Leu Gln Asp
            420                 425                 430

Tyr Phe Gln Thr His Leu Pro Glu Tyr Glu Ser Ser Phe Glu Asn Leu
        435                 440                 445

Tyr Leu Glu Ser Glu Gly Asn Glu Lys Lys Thr Ala Ile Leu Arg Ala
450                 455                 460

Val Tyr Asn Tyr Val Gln Gln Leu Val Ser Ser Ala Gly His His His
465                 470                 475                 480

His His His

<210> SEQ ID NO 14
<211> LENGTH: 485
<212> TYPE: PRT
<213> ORGANISM: Artificial sequence
<220> FEATURE:
<223> OTHER INFORMATION: His tagged Psychromonas sp. exonuclease

<400> SEQUENCE: 14

Met Asn Gln Glu Ser Pro Ser Leu Leu Trp His Asp Tyr Glu Thr Phe

-continued

```
1               5                   10                  15
Gly Leu Asn Pro Gly Thr Asp Arg Pro Ser Gln Phe Ala Gly Ile Arg
            20                  25                  30
Thr Asp Leu Asp Leu Asn Ile Ile Ser Glu Pro Tyr Gln Trp Tyr Cys
                35                  40                  45
Arg Pro Pro Asn Asp Tyr Leu Pro Ala Pro Glu Ala Cys Leu Val Thr
 50                  55                  60
Gly Ile Thr Pro Gln Tyr Ala Leu Gln His Gly Glu Phe Glu Asn Gln
 65                  70                  75                  80
Phe Ile Phe Asn Ile Leu Gln Gln Phe Gln Gln Asn Thr Cys Val
                85                  90                  95
Val Gly Tyr Asn Asn Ile Arg Phe Asp Asp Glu Val Thr Arg Phe Thr
                100                 105                 110
Leu Tyr Arg Asn Phe His Asp Pro Tyr Gln Arg Glu Trp Gln Asn Gly
                115                 120                 125
Cys Ser Arg Trp Asp Ile Ile Asp Met Val Arg Ala Cys Tyr Ala Leu
            130                 135                 140
Arg Pro Glu Gly Ile Glu Trp Val Phe Asp Glu Asn Asp Ala Pro Ser
145                 150                 155                 160
Phe Lys Leu Glu Leu Leu Thr Lys Ala Asn Asp Ile Val His Gln Gln
                165                 170                 175
Ala His Asp Ala Met Ser Asp Val Tyr Ala Thr Ile Ala Met Ala Lys
            180                 185                 190
Leu Ile Lys Thr Ala His Pro Lys Leu Tyr Asp Tyr Cys Tyr Ser Leu
            195                 200                 205
Arg Gln Lys Asn Lys Val Leu Asn Glu Leu Lys Leu Gly Thr Phe Lys
210                 215                 220
Pro Leu Val His Ile Ser Gly Met Phe Ser Ala Met Gln Gly Cys Cys
225                 230                 235                 240
Ser Tyr Ile Leu Pro Ile Ala Gln His Pro Ser Asn Asn Asn Ala Val
                245                 250                 255
Ile Val Leu Asp Leu Asn Lys Asp Ile Ser Gln Leu Leu Ser Leu Ser
            260                 265                 270
Val Glu Asp Ile Gln Ser Tyr Leu Tyr Thr Ala Thr Asp Asn Leu Pro
            275                 280                 285
Glu Gly Ile Asn Arg Pro Pro Ile Lys Leu Ile His Ile Asn Lys Cys
            290                 295                 300
Pro Ile Val Ala Ser Ala Lys Thr Leu Ser Ala Glu Arg Ala Lys Glu
305                 310                 315                 320
Leu Gly Val Asp Ala Lys Gln Cys Arg Gln Ser Met Asp Thr Phe Ser
            325                 330                 335
Glu Asn Lys His Leu Val Glu Lys Leu Ile Ala Val Phe Asp Thr Glu
            340                 345                 350
Ser Lys Ser Ser Lys Glu Gln Gln Pro Glu Gln Lys Leu Tyr Ser Gly
            355                 360                 365
Gly Phe Pro Thr Ala Asn Asp Lys Asn Gln Lys Ala Ile Thr Ser
 370                 375                 380
Leu Ser Pro Gln Gln Ile Ala Asn Tyr Gln Val Thr Phe Asp Asp Pro
385                 390                 395                 400
Asn Phe Asp Asn Leu Trp Trp Arg Tyr Lys Ala Arg Asn Tyr Pro Gln
                405                 410                 415
Met Leu Ser Leu Glu Glu Gln Gln Lys Trp Gly Arg His Arg Glu Ala
            420                 425                 430
```

```
Tyr Leu Ile Glu His Val Asp Asn Tyr Val Ala Arg Leu Glu Met Leu
            435                 440                 445

Val Ile Glu His Gln His Ser Pro Glu Lys Ile Glu Val Leu Gln Lys
            450                 455                 460

Leu Gly His Tyr Leu Glu Phe Leu Thr Gly Asn Thr Ser Ala Gly His
465                 470                 475                 480

His His His His His
            485

<210> SEQ ID NO 15
<211> LENGTH: 489
<212> TYPE: PRT
<213> ORGANISM: Artificial Sequence
<220> FEATURE:
<223> OTHER INFORMATION: His tagged Moritella viscosa exonuclease

<400> SEQUENCE: 15

Met Asp Asn Asn Ser Asn Lys Thr Ala Thr Asp Leu Pro Thr Phe Tyr
1               5                   10                  15

Trp His Asp Tyr Glu Thr Phe Gly Leu Ser Pro Ser Leu Asp Arg Pro
            20                  25                  30

Ser Gln Phe Ala Gly Ile Arg Thr Asp Met Asp Phe Asn Val Ile Gly
        35                  40                  45

Glu Pro Asp Met Phe Tyr Cys Arg Gln Ser Asp Asp Tyr Leu Pro Ser
50                  55                  60

Pro Glu Ala Ala Met Ile Thr Gly Ile Thr Pro Gln Lys Thr Gln Ala
65                  70                  75                  80

Glu Gly Val Ser Glu Ala Glu Phe Ser Lys Arg Ile Glu Ala Gln Phe
            85                  90                  95

Ser Gln Lys Asn Thr Cys Ile Ile Gly Tyr Asn Asn Ile Arg Phe Asp
        100                 105                 110

Asp Glu Val Thr Arg Asn Ile Phe Tyr Arg Asn Phe Tyr Asp Pro Tyr
        115                 120                 125

Ala His Thr Trp Lys Asp Gly Asn Ser Arg Trp Asp Ile Ile Asp Leu
    130                 135                 140

Met Arg Ala Cys Tyr Ala Leu Arg Pro Glu Gly Ile Val Trp Pro Glu
145                 150                 155                 160

Asn Asp Asp Gly Leu Pro Ser Met Arg Leu Glu Leu Leu Thr Ala Ala
            165                 170                 175

Asn Gly Ile Glu His Ala Asn Ala His Asp Ala Thr Ser Asp Val Tyr
        180                 185                 190

Ala Thr Ile Ala Met Ala Lys Leu Val Lys Glu Lys Gln Pro Lys Leu
    195                 200                 205

Phe Asp Phe Leu Phe Asn Leu Arg Ser Lys Arg Lys Val Glu Ser Leu
210                 215                 220

Val Asp Ile Ile Asn Met Thr Pro Leu Val His Val Ser Gly Met Phe
225                 230                 235                 240

Gly Ala Asp Arg Gly Phe Thr Ser Trp Val Val Pro Leu Ala Trp His
            245                 250                 255

Pro Thr Asn Asn Asn Ala Val Ile Val Ala Asp Leu Ala Gln Asp Ile
        260                 265                 270

Thr Pro Leu Leu Glu Leu Ser Ala Asp Glu Leu Arg Glu Arg Leu Tyr
    275                 280                 285

Thr Pro Lys Lys Asp Leu Gly Asp Leu Thr Pro Ile Pro Leu Lys Leu
    290                 295                 300
```

```
Ile His Ile Asn Lys Cys Pro Val Leu Ala Pro Ala Lys Thr Leu Leu
305                 310                 315                 320

Pro Glu Asn Ala Glu Arg Leu Gly Ile Asp Arg Ser Ala Cys Leu Ala
                325                 330                 335

Asn Leu Lys Arg Leu Lys Glu Ser Ala Thr Leu Arg Glu Asn Val Val
            340                 345                 350

Gly Val Tyr Gln Val Glu Arg Glu Tyr Pro Lys Ser Thr Asn Val Asp
        355                 360                 365

Ala Met Ile Tyr Asp Gly Phe Phe Ser Ala Gly Asp Lys Ala Asn Phe
    370                 375                 380

Glu Ile Leu Arg Glu Thr Ala Pro Glu Gln Leu Thr Gly Leu Gln Leu
385                 390                 395                 400

Lys Val Ser Asp Ser Arg Phe Asn Glu Leu Phe Phe Arg Tyr Arg Ala
                405                 410                 415

Arg Asn Phe Pro His Leu Leu Ser Met Pro Glu Gln Gln Lys Trp Leu
            420                 425                 430

Asp His Cys Arg Thr Val Leu Glu Asp Ser Ala Pro Ala Tyr Phe Ala
        435                 440                 445

Arg Leu Asp Ala Leu Ala Ile Glu Asn Ser His Asp Glu Arg Lys Met
    450                 455                 460

Lys Leu Leu Gln Gln Leu Tyr Leu Tyr Gly Gln Lys Ile Ile Gly Ala
465                 470                 475                 480

Ser Ala Gly His His His His His His
                485

<210> SEQ ID NO 16
<211> LENGTH: 1443
<212> TYPE: DNA
<213> ORGANISM: Artificial Sequence
<220> FEATURE:
<223> OTHER INFORMATION: His tagged Shewanella sp. exonuclease

<400> SEQUENCE: 16
atgaacaaca ctaagaaaca gccaacttta ttttggcacg attatgaaac atttggtgct    60
aatccagcca agataggcc atcgcagttt gctggtgtgc gtaccgacat ggatctcaat    120
atcattgctg agcctgtcac attttactgt aaagtcgcga atgactacct gccctcacct    180
gaagctattt taattacagg tataacacca cagcttgcta accttaaagg gatgcctgaa    240
gctgagttta tggcacaaat ccaccagttg tttagccaag aaaatacctg tgttgtgggt    300
tacaactcaa ttagatttga tgatgaagtc tcccgctatg cttttaccg taacttttt    360 gacccgtatg ctagagaatg gaaaaacggt aatagtcgct gggatatcat tgatttagta    420
cgtgcttgtt atgcctttag gcccgatgga ataaactggc acaaaaaga agatggctct    480 ccaagtttta aactcgaaca cttaaccgtt gccaatggcc ttagccatga aaaagcccac    540
gatgctatgt ctgatgtgta tgccactatt gcgatggcta agcttatcaa atcagtgcag    600
cctaaattgt ttgaatatta cttcaatctg cgccgaaaac aggaagtttc gaagctaatc    660
gacgtactag aaatgaaacc gttagtgcat gtaagttcaa agattagcgc gctaaatggc    720
tgtaccacat taatcgcgcc gctggccttt cacacgacta taaaaatgc ggttatctgt    780 gtcaatttag ccatggatgt cacgccgctc attgagttga ccgccgagca aattcgagag    840
cgcatgtaca caaggcgtga tgatttagcg gaagatgagt tacctattgg catcaaacaa    900
atccatatca acaaaagtcc atttattgcc ggtgctaaat cattaaccga tgaaaatgcc    960
```

```
gctcgtcttg atattgataa agcatttgca agagatcaat ataagcggct tagacagcac    1020
ccagagatac gagaaaagct cgttgcggtg tttgacatcg agtccgatcg tatcattacc    1080
gatcccgatc ttcagcttta tagcggtggc ttttttagcc atgcggataa agcaaaaatg    1140
gagatgatcc gtaataccaa acctattaat ttagccgcac tggagctgtc atttgacgat    1200
gagcgcttac cagaaatgtt gtatcgatat agagcacgta attatcctga aacactggat    1260
gaatctgaga gcattcgttg gcgtgaattc tgtcaatcaa ggctcaatga tcctgattac    1320
atgataaaac ttgaaaacat tattgaacaa accgagcaag atgaagtaaa gcaaaaatta    1380
ttacaggctt tgtgtcatta tcttagaaat ctttctgcag gccatcacca tcaccatcac    1440
tag                                                                  1443
```

<210> SEQ ID NO 17
<211> LENGTH: 1521
<212> TYPE: DNA
<213> ORGANISM: Artificial sequence
<220> FEATURE:
<223> OTHER INFORMATION: His tagged Halmonas sp. exonuclease

<400> SEQUENCE: 17

```
atggcatcac ccaatgctgc ccctgccagt tttctctggc atgattatga aaccttcggg     60
gctgacccgc ccgcgatcg gcccgctcag ttcgctgcac tgcgcacgga tgcagaactg    120
aacgagatcg gtgagcccat cgagctctac tgcaaacccg ccgatgacta cctgcctcat    180
cctgctgcct gtttgatcac cggtattacc cctcaaaaag cccagcgcca tggtctcccc    240
gaagcagagt tcgcgggtga gattcagcgc acatgagcg agccgggtac ctgcgtagtg    300
ggctacaaca gcctgcgttt tgatgacgaa gtttcgcgcc acctgttttta ccgcaatttg    360 cttgacccctt attcccgcga gtggcaaaac ggcaattccc gctgggattt aatcgatatt    420
gtgcgcgcct tttatgcgct cgcccggat ggcattgaat ggccgctgcg cgaagacggt    480
gcacccagct ttaagctcga gcacttaact gccgccaacg gcattgccca tgagggtgcc    540
cacgatgcgg tggcagatgt ccgcgctact atcgccttgg cgcggttgct caaagtgcgc    600
aatgccaagc tgtttgacta tctgctcggc ctgcgcggta gcgcgcggt ggccaagcag    660 ctcgacttgc ccaacgccaa accgctgctg catatctccc gccgttatcc tgctagccgg    720
ggctgtagtg cactagtcat gccgctggcc gagcacccga caaaccctaa tggggtgatt    780
gtttacgatt tgagcgttga tcccagcgat atgctgagca tgtcggcgga gcaaattcgt    840
gagcgggtgt ttgtcagtca gcaggatctc gccgaaggcg aggcgcgcat tccgctaaag    900
atcatccata tcaaccgctg cccagtggtg ttccccgcta gtgctttgaa agacgttgag    960
gggcctcatc agggcgagta tggcaccatc gtcgcgcgct taggcttaga gtgtggctgcc    1020 tgtcggcagc actggaaaac cctgcgcgat gccagcggtg tcgccgctaa ggtcgccgag    1080
gtgtttagtg ccggttacga cgatgtaccc caagaccctg atctaatgct ctattcgggc    1140
agtttcttct ccgctgctga ccgtcagcag atggagcggg tgcgagagat ggaaccgtgg    1200
gacctggtcg gtcagcgctt tgcgtttcag gatccgcgtt tggaagagat gctgttttcgc    1260 tttcgtgcgc gcagttaccc cgacacgttg gaaggcgaag agcgcgagca gtgggaggcg    1320
tttcgctgga tgcggatcaa tgacccggcc ttggcgggct ttacgcttaa ggcgtttgcg    1380
cgggaaatcg agcagtacaa tcagcaaacc ctcactgatc gcgagcggca ggttctggaa    1440
gagctggtga tgttcgtgga agccatgatg ccggcccagg catttgatgc ctctgcaggc    1500
catcaccatc accatcactg a                                             1521
```

<210> SEQ ID NO 18
<211> LENGTH: 1452
<212> TYPE: DNA
<213> ORGANISM: Artificial sequence
<220> FEATURE:
<223> OTHER INFORMATION: His tagged Vibrio wodanis exonuclease

<400> SEQUENCE: 18

| | |
|---|---:|
| atgccgcagg ataacgcacc aagtttcttc tttttgatt atgaaacatg gggaactagc | 60 |
| ccatctctcg atcgcccatg ccaatttgct ggagttcgta ccgatgaaga tttcaatatc | 120 |
| attggtgagc cattagttat ttactgtcgc cctccaattg attatttacc ttctcctgaa | 180 |
| gcctgtttaa ttactggcat cacgccacaa actgcggtaa ataaaggcct gtctgagcct | 240 |
| gagttcatta ctcaaatcca taacgaatta tcaaaaccaa atacttgctc gctaggctat | 300 |
| aacaacattc gttttgatga tgaagtttct cgctacacct tatatcgtaa cttctttgaa | 360 |
| ccgtatggct ggagctggca aaacggcaac tcgcgttggg atctacttga tgtaatgcgt | 420 |
| gctgtgtatg ctctgcgtcc tgaaggcatt aaatggccaa agacgaaga aggcaaacca | 480 |
| agctttagat tagaaaaact ctcgcaagca atggcattg aacatgaaaa tgcccacgat | 540 |
| gcgatggccg atgttattgc caccatcgag ttagctaaag tcgttaaaaa agcacaacct | 600 |
| aaaatgttta actacctgct ttctatgcgt cataaaaaga aagcggcaac gttaatcgat | 660 |
| attgttgaaa tgacaccgtt aatgcacgtg tctggtatgt ttggcgtaga tagaggcaat | 720 |
| attagttgga ttgtgcctgt tgcttggcat cctaccaata caacgccgt cattacgatt | 780 |
| gatttagcgt tagacccaag tgtgttccta gaattagatg cagagcaatt acatcaacgc | 840 |
| atgtatacca aacgtgctga tctagccct gacgaattgc ctgttcctgt aaaattagta | 900 |
| catttaaaca agtgccctat tcttgcgcct gctaaaacat tgacggctga aatgctgaa | 960 |
| aatctaaatg tggacagagc cgcctgttta aaaaatctta agtgatccg tgataaccct | 1020 |
| gagatcagac aaaagctaat tgcgctttac agcattgagc ctaattatga gaaatcaacc | 1080 |
| aatgtagata cccttctata tgatggttc ttctctcatg ctgataaaac gacgattgat | 1140 |
| attatccgtc agtcaacgcc tgagcagctt atcgattttg aaccaaatgt cagtgaccca | 1200 |
| cgcattaaac tctctattatt ccgctatcgt gcgcgcaatt tcccgcatac gcttaatgag | 1260 |
| acagagcaac tgaaatggca atcacattta caagattact tccaaactca tttacctgaa | 1320 |
| tacgaatcaa gctttgagaa tttatatctt gaatctgaag gcaatgagaa aaagactgcg | 1380 |
| atccttcgcg ccgtttataa ttacgtacaa cagttagtat catctgcagg ccatcaccat | 1440 |
| caccatcact ga | 1452 |

<210> SEQ ID NO 19
<211> LENGTH: 1458
<212> TYPE: DNA
<213> ORGANISM: Artificial sequence
<220> FEATURE:
<223> OTHER INFORMATION: His tagged Psychromonas sp. exonuclease

<400> SEQUENCE: 19

| | |
|---|---:|
| atgaatcaag aatccccaag ccttctttgg cacgattatg aaaccttcgg gttaaaccca | 60 |
| ggaacggatc gcccttctca gtttgcaggc attcgtactg atcttgattt aaatatcatt | 120 |
| tctgagcctt atcaatggta ctgcagacca cccaacgatt atttacctgc tcctgaagcg | 180 |
| tgtttagtaa cgggaataac accacaatat gcgttgcaac atggtgaatt tgaaaaccaa | 240 |

| | |
|---|---|
| tttatatttta atatattgca gcaattccaa cagcaaaaca cgtgcgttgt tgggtataac | 300 |
| aatattcgct ttgatgatga agtcacacgc tttactttgt atcgtaattt tcatgaccct | 360 |
| tatcaaagag aatggcaaaa tggctgctct cgctgggaca ttattgacat ggttcgcgct | 420 |
| tgctatgcac tcagaccaga aggtattgaa tgggtatttg atgaaaatga tgcgccaagt | 480 |
| tttaaacttg agttattaac taaagctaat gacattgttc atcagcaagc acatgatgcg | 540 |
| atgtcggatg tttatgccac tatcgccatg gcaaaactaa ttaagacagc acatccaaag | 600 |
| ctatatgact attgttatag tttgagacaa aaaaataaag tattaaacga actgaagctt | 660 |
| ggtacattta aacctttagt tcatatctct ggtatgtttt ctgcgatgca aggctgttgt | 720 |
| tcttatattt tacctatcgc acaacaccca agtaacaata atgcagtgat agtgcttgat | 780 |
| ttaaataaag atatttcaca acttttatcg ttgagtgttg aagatatcca atcttactta | 840 |
| tataccgcta cggataattt accagagggt attaatagac cccctattaa attaatccat | 900 |
| attaataaat gccctatcgt agcaagtgca aaaacattaa gtgcagagag agcaaaagaa | 960 |
| ttaggggttg atgcaaaaca atgccgtcaa tcaatggata cgttctcaga aaataaacat | 1020 |
| ttggttgaga aactgattgc agtgtttgac actgaatcca aaagcagcaa ggaacaacaa | 1080 |
| ccagaacaaa aattgtattc tggcggtttc cctactgcta cgacaaaaa tcaagcaaaa | 1140 |
| gcgatcacca gtttgtcgcc acaacaaatt gctaattacc aagttacttt tgatgatcct | 1200 |
| aattttgata atttatggtg gcgatacaaa gcaagaaatt atccgcaaat gttatcactt | 1260 |
| gaagagcaac aaaaatgggg tagacacaga gaagcttatc ttattgaaca tgtagataat | 1320 |
| tatgttgcac gcttagaaat gctagtgatt gagcatcaac atagcccaga aaagatcgaa | 1380 |
| gtattgcaaa aactgggaca ttacttagag ttttgacag ggaatacatc tgcaggccat | 1440 |
| caccatcacc atcactga | 1458 |

<210> SEQ ID NO 20
<211> LENGTH: 1470
<212> TYPE: DNA
<213> ORGANISM: Artificial Sequence
<220> FEATURE:
<223> OTHER INFORMATION: His tagged Moritella viscosa exonuclease

<400> SEQUENCE: 20

```
atggataaca attcgaacaa aacagcaaca gatctgccca ctttttactg gcatgattat     60
gagacttttg gcttaagtcc gtcactggat cgcccttctc aatttgctgg tattcgcacc    120
gacatggact ttaatgtgat cggcgaacca gatatgtttt actgccgcca atcagatgat    180
taccttcctt cgccagaagc tgccatgatt actgggataa cacctcaaaa gacccaagca    240
gaaggtgtaa gtgaagcaga gttcagtaaa cgtattgaag cgcaattcag tcaaaaaaac    300
acctgtatca ttggttataa caacattcgc tttgatgatg aagtaacacg taatatcttc    360
taccgtaatt tctacgaccc atacgcacac acctggaaag atggtaattc gcgctgggat    420
attattgact tgatgcgcgc ttgttatgct ctgcgccctg aaggtattgt atggccagaa    480
aatgatgatg gtctaccaag tatgcgtctt gaattattaa ccgccgcaaa tggcattgag    540
cacgctaatg cccatgatgc tacttctgat gtatatgcaa ctatcgcgat ggcgaagcta    600
gttaaagaaa aacaacctaa gctgtttgat ttcttattta acctacgtag caaacgtaaa    660
gttgaatcct tggttgatat catcaacatg acaccattag tgcatgtaag cggcatgttt    720
ggtgcagatc gcggattcac aagctgggta gtgccactgg cttggcaccc aaccaacaac    780
aacgctgtga ttgtagctga cttagcccaa gacattacgc cattattaga attgagcgcg    840
```

```
gatgaactgc gcgaacgttt atatacgcca agaaagatc tcggtgactt aaccccctatc    900
ccgctgaaac ttattcatat caacaagtgt ccagtactcg cgccagcgaa aactctatta    960
cctgaaaacg cagaacgttt agggattgat cgcagcgcct gcctcgcaaa cctaaaacgt   1020
ttaaaagaaa gcgcaacact gcgtgaaaat gttgtgggtg tttatcaagt agaacgtgaa   1080
tatccaaaat caaccaatgt ggatgcaatg atctacgatg gtttctttag tgcaggtgat   1140
aaagcaaact ttgaaatact acgtgaaaca gcaccagagc aacttacagg actgcaactg   1200
aaagtcagtg attcgcgttt taatgaatta ttcttccgct atcgagcacg taacttcccg   1260
catttattat caatgcctga gcaacaaaaa tggcttgacc actgccgaac tgtgctagaa   1320
gacagtgccc cagcctattt tgcacgttta gatgcattag cgatcgaaaa cagccatgac   1380
gagcgaaaaa tgaaactact tcaacagtta tacctttatg gtcaaaaaat aattggcgca   1440
tctgcaggcc atcaccatca ccatcactga                                    1470
```

<210> SEQ ID NO 21
<211> LENGTH: 20
<212> TYPE: DNA
<213> ORGANISM: Artificial sequence
<220> FEATURE:
<223> OTHER INFORMATION: Probe

<400> SEQUENCE: 21

```
gctaactacc acctgattac                                                 20
```

<210> SEQ ID NO 22
<211> LENGTH: 475
<212> TYPE: PRT
<213> ORGANISM: Escherichia coli

<400> SEQUENCE: 22

```
Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Cys Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Cys Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Cys
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190
```

```
Met Ala Lys Leu Val Lys Thr Arg Gln Pro Arg Leu Phe Asp Tyr Leu
            195                 200                 205

Phe Thr His Arg Asn Lys His Lys Leu Met Ala Leu Ile Asp Val Pro
        210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
        275                 280                 285

Asp Leu Gly Asp Asn Ala Ala Val Pro Val Lys Leu Val His Ile Asn
        290                 295                 300

Lys Cys Pro Val Leu Ala Gln Ala Asn Thr Leu Arg Pro Glu Asp Ala
305                 310                 315                 320

Asp Arg Leu Gly Ile Asn Arg Gln His Cys Leu Asp Asn Leu Lys Ile
                325                 330                 335

Leu Arg Glu Asn Pro Gln Val Arg Glu Lys Val Val Ala Ile Phe Ala
            340                 345                 350

Glu Ala Glu Pro Phe Thr Pro Ser Asp Asn Val Asp Ala Gln Leu Tyr
        355                 360                 365

Asn Gly Phe Phe Ser Asp Ala Asp Arg Ala Ala Met Lys Ile Val Leu
    370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
                405                 410                 415

Gly Thr Leu Asp Tyr Ala Glu Gln Gln Arg Trp Leu Glu His Arg Arg
            420                 425                 430

Gln Val Phe Thr Pro Glu Phe Leu Gln Gly Tyr Ala Asp Glu Leu Gln
        435                 440                 445

Met Leu Val Gln Gln Tyr Ala Asp Asp Lys Glu Lys Val Ala Leu Leu
    450                 455                 460

Lys Ala Leu Trp Gln Tyr Ala Glu Glu Ile Val
465                 470                 475

<210> SEQ ID NO 23
<211> LENGTH: 66
<212> TYPE: DNA
<213> ORGANISM: Artificial Sequence
<220> FEATURE:
<223> OTHER INFORMATION: Primer

<400> SEQUENCE: 23
gtgagcggat aacaatttca cacaggaaac agaccatgga taacaattcg aacaaaacag    60
caacag                                                              66

<210> SEQ ID NO 24
<211> LENGTH: 91
<212> TYPE: DNA
<213> ORGANISM: Artificial Sequence
<220> FEATURE:
<223> OTHER INFORMATION: Primer

<400> SEQUENCE: 24
gctgaaaatc ttctctcatc cgccaaaaca gcctcagtga tggtgatggt gatggcctgc    60
```

```
agatgcgcca attattttt gaccataaag g                                    91

<210> SEQ ID NO 25
<211> LENGTH: 58
<212> TYPE: DNA
<213> ORGANISM: Artificial Sequence
<220> FEATURE:
<223> OTHER INFORMATION: Primer

<400> SEQUENCE: 25
gtgagcggat aacaatttca cacaggaaac agaccatgcc gcaggataac gcaccaag      58

<210> SEQ ID NO 26
<211> LENGTH: 98
<212> TYPE: DNA
<213> ORGANISM: Artificial Sequence
<220> FEATURE:
<223> OTHER INFORMATION: Primer

<400> SEQUENCE: 26
gctgaaaatc ttctctcatc cgccaaaaca gcctcagtga tggtgatggt gatggcctgc    60
agatgatact aactgttgta cgtaattata aacggcgc                            98

<210> SEQ ID NO 27
<211> LENGTH: 56
<212> TYPE: DNA
<213> ORGANISM: Artificial Sequence
<220> FEATURE:
<223> OTHER INFORMATION: Primer

<400> SEQUENCE: 27
gtgagcggat aacaatttca cacaggaaac agaccatggc atcacccaat gctgcc        56

<210> SEQ ID NO 28
<211> LENGTH: 83
<212> TYPE: DNA
<213> ORGANISM: Artificial Sequence
<220> FEATURE:
<223> OTHER INFORMATION: Primer

<400> SEQUENCE: 28
gctgaaaatc ttctctcatc cgccaaaaca gcctcagtga tggtgatggt gatggcctgc    60
agaggcatca aatgcctggg ccg                                            83

<210> SEQ ID NO 29
<211> LENGTH: 65
<212> TYPE: DNA
<213> ORGANISM: Artificial sequence
<220> FEATURE:
<223> OTHER INFORMATION: Primer

<400> SEQUENCE: 29
gtgagcggat aacaatttca cacaggaaac agaccatgaa tcaagaatcc ccaagccttc    60
tttgg                                                                65

<210> SEQ ID NO 30
<211> LENGTH: 96
<212> TYPE: DNA
<213> ORGANISM: Artificial Sequence
<220> FEATURE:
<223> OTHER INFORMATION: Primer

<400> SEQUENCE: 30
```

```
gctgaaaatc ttctctcatc cgccaaaaca gcctcagtga tggtgatggt gatggcctgc        60
agatgtattc cctgtcaaaa actctaagta atgtcc                                 96

<210> SEQ ID NO 31
<211> LENGTH: 71
<212> TYPE: DNA
<213> ORGANISM: Artificial Sequence
<220> FEATURE:
<223> OTHER INFORMATION: Primer

<400> SEQUENCE: 31
gtgagcggat aacaatttca cacaggaaac agaccatgaa caacactaag aaacagccaa        60
ctttattttg g                                                            71

<210> SEQ ID NO 32
<211> LENGTH: 96
<212> TYPE: DNA
<213> ORGANISM: Artificial Sequence
<220> FEATURE:
<223> OTHER INFORMATION: Primer

<400> SEQUENCE: 32
gctgaaaatc ttctctcatc cgccaaaaca gcctcagtga tggtgatggt gatggcctgc        60
agaaagattt ctaagataat gacacaaagc ctgtaa                                 96
```

THERMOLABILE EXONUCLEASES

CROSS-REFERENCE TO RELATED APPLICATIONS

The present application is a national stage filing under 35 U.S.C. § 371 of PCT/EP2015/001703, filed on 19 Aug. 2015, which in turn claims the benefit of priority to and the benefit of GB Application No. 1414745.8, filed 19 Aug. 2014. Each application is incorporated herein by reference in its entirety.

The present invention relates to thermolabile exonucleases and the use of the same to remove single stranded DNA from samples containing biological molecules, in particular the products of nucleic acid amplification or reverse transcription reactions (e.g. double stranded DNA, RNA and DNA:RNA duplexes). The invention may therefore be viewed particularly as relating to the refinement of samples containing double stranded DNA, RNA and/or DNA:RNA duplexes by removing single stranded DNA. More specifically the invention relates to the removal of excess oligodeoxyribonucleotide primers from the products of nucleic acid amplification or reverse transcription reactions. Removal of excess oligodeoxyribonucleotide primers from the products of nucleic acid amplification reactions may enhance the downstream sequence analysis of such products as interference from excess oligodeoxyribonucleotide primers is reduced. The present invention therefore further relates to methods for optimising the sequence analysis of the products of a nucleic acid amplification or reverse transcription reactions, e.g. by nucleic acid sequencing or oligonucleotide probe arrays. Methods for optimising the sequence analysis of nucleic acids that have not been obtained from a nucleic acid amplification reaction are also provided.

Nucleases are enzymes that break the phosphodiester bonds in the sugar-phosphate backbone of DNA or RNA polymers. Nucleases are a very diverse group of enzymes. The mode of action can be either highly specific or very general depending upon their target function. Nucleases may prefer single stranded (ss) polymers or double stranded (ds) polymers. Some nucleases cleave at specific nucleotide sequences (e.g. restriction endonucleases), whereas others cleave at positions in the polymers independent of nucleotide sequence. In the cell, nucleases have a variety of functions and are involved in DNA replication, recombination, mutation, transcription and repair in addition to breaking down redundant pieces of RNA and DNA. Nucleases may also serve a role in host defence mechanisms.

All nucleases may be divided into three major classes based on whether their catalytic mechanism involves two, one or no metal ions (the two-metal-ion dependent, one-metal-ion-dependent and metal independent nuclease superfamilies). Each of these classes includes many different families and superfamilies. For more details about nuclease classification see Yang, W., 2011, "Nucleases: diversity of structure, function and mechanism." Q Rev Biophys 44(1): 1-93.

Based on substrate preference nucleases may be classified as deoxyribonucleases (DNases) or ribonucleases (RNases), i.e. enzymes that cleave the phosphodiester bonds of either DNA or RNA, respectively. Based on the positions of the cleaved bonds within the DNA or RNA polymers, nucleases may be further classified as endonucleases or exonucleases. The endonucleases cleave phosphodiester bonds of DNA or RNA at positions within the polymer, whereas exonucleases are involved in trimming the ends of RNA and DNA polymers, cleaving the outermost phosphodiester bond in a chain. Exonucleases can be further divided into two groups by the 5' to 3' versus 3' to 5' polarity. Nucleases may also display specificity between single- and double-stranded nucleic acids. A particular nuclease may be strictly single-strand-specific, single-strand-preferential, strictly double-strand-specific, double-strand-preferential or a nuclease that cleaves both.

A number of exonuclease enzymes are known, and among them, the *Escherichia coli* enzymes are the most well-characterised ones. A common feature for exonucleases is their high processivity degrading up to a 1000 nucleotides in a single binding event releasing mononucleotides. Exonuclease I (ExoI), Exonuclease VII (ExoVII) and RecJ exonuclease are all reported to be ssDNA-specific exonucleases involved in DNA repair. However, their polarity of action is different. ExoI possesses 3' to 5' exonuclease activity while RecJ possesses only 5' to 3' activity. In contrast to the other exonucleases, ExoVII possesses both 5' to 3' and 3' to 5' exonuclease activities.

The determination of the sequence of nucleotides in nucleic acids, e.g. DNA and RNA, has become an important goal in modern molecular biology. By analysing such sequences information on the source of the nucleic acid can be obtained. For instance, the nucleotide sequence of certain evolutionarily variable genetic elements can provide an indication as to the identity of the organism from which it is derived. Accordingly, detecting nucleic acid carrying a nucleotide sequence characteristic of a particular microorganism in a sample can indicate the presence of the microorganism in the sample or even quantify the amounts of such organisms in the sample. Sequence analysis can also assist in the taxonomic classification of higher organisms, which may be important in technical fields such as agriculture and veterinary science. In humans, nucleotide sequence analysis can identify individuals and their lineage, thus having forensic applications, and can identify medically or physiologically relevant genotypes, e.g. mutations. The sequencing of the RNA transcripts of a target cell or group of cells (e.g. a tissue, a tumour or a culture) can yield information on the transcriptome of the target, which in turn can have numerous applications in the medical and scientific fields. Nucleic acid based identity tags carrying unique nucleotide sequences are also available, the detection of which requires the analysis of the nucleotide sequence of the tag. In other representative applications the skilled person may wish to ascertain the nucleotide sequence of a nucleic acid with which he/she is working, perhaps either to confirm a manipulation has succeeded or to understand the make-up of a novel molecule.

Nucleic acid sequence analysis may take the form of a sequencing technique. The Sanger dideoxynucleotide sequencing method is a well-known and widely used technique for sequencing nucleic acids. However more recently the so-called "next generation" or "second generation" sequencing approaches (in reference to the Sanger dideoxynucleotide method as the "first generation" approach) have become widespread. These newer techniques are characterised by high throughputs, e.g. as a consequence of the use of parallel, e.g. massively parallel sequencing reactions, or through less time-consuming steps. Various high throughput sequencing methods provide single molecule sequencing and employ techniques such as pyrosequencing, reversible terminator sequencing, cleavable probe sequencing by ligation, non-cleavable probe sequencing by ligation, DNA nanoballs, and real-time single molecule sequencing.

Nucleic acid sequence analysis may also take the form of an oligonucleotide hybridisation probe based approach in which the presence of a target nucleotide sequence is confirmed by detecting a specific hybridisation event between a probe and its target. In these approaches the oligonucleotide probe is often provided as part of a wider array, e.g. an immobilised nucleic acid microarray.

Further approaches are available and may be developed in the future, but as a common theme it is typical, albeit not essential, that each are performed on nucleic acid that has been amplified in a nucleic acid amplification reaction or synthesised by a reverse transcription (RT) reaction. Amplification is typically required to ensure that there is sufficient nucleic acid sample for the sequence analysis. Such techniques include the polymerase chain reactions (PCRs), ligase amplification reaction (LAR; also known as ligase chain reaction (LCR)), strand displacement amplification (SDA), nucleic acid sequence based amplification (NASBA; also known as 3SR (Self-Sustaining Sequence Replication)) and may be preceded by a reverse transcription reaction. These amplification techniques and reverse transcription techniques often result in the presence of non-target single stranded DNA in the final product, mainly because an excess of single stranded oligodeoxyribonucleotide primer is often supplied initially, but single stranded DNA amplicons may also arise when polymerisation is incomplete. Such single stranded DNA interfere with the sequence analysis of the amplification product by competing with the other reagents, e.g. oligonucleotide probes, and undergoing sequencing themselves, thereby contaminating the sequencing information outputted by the reaction. This potentially lowers the sensitivity and accuracy of the analysis.

To mitigate such interference the product of a nucleic acid amplification reaction or a reverse transcription reaction may be treated with an exonuclease to degrade single stranded DNA (e.g. unincorporated primers). It is also possible to include a treatment to effect the dephosphorylation of any unincorporated NTPs (e.g. dNTPs), e.g. a treatment with an alkaline phosphatase, for instance the heat-labile shrimp alkaline phosphatase (SAP). Today exonuclease I from *E. coli* (ExoI) is the most commonly used exonuclease in such reactions. The exonuclease I reaction is typically performed by adding the enzyme to the product of the nucleic acid amplification or the reverse transcription reaction and incubating for 15 min at 37° C. However, to prevent the exonuclease from interfering with downstream processes, e.g. sequence analysis, it is usually necessary to inactivate the enzyme. With the commonly used exonuclease I from *E. coli*, inactivation requires incubation of the enzyme at 80° C. for 15-20 minutes. The long inactivation time and relatively high inactivation temperature makes the process time consuming and relatively harsh on the sample of interest.

RecJ and ExoVII have also been proposed for such a use, but are not commonly used because RecJ has a low specific activity and ExoVII consists of two different polypeptide chains. The recommended inactivation conditions for RecJ involve a 20 min incubation at 65° C. and for ExoVII a 10 minutes incubation at 95° C.

There is a need therefore to provide an enzyme capable of specifically degrading single stranded DNA in under 15 minutes and/or which may be essentially irreversibly inactivated at a temperature below 65° C. and/or in less than 15-20 minutes. Such a thermolabile (also interchangeably referred to herein as a heat-labile (HL)) enzyme would improve molecular biology techniques by making them significantly more time efficient and gentler on the sample molecule of interest.

It may be desirable to remove single stranded DNA from a sample in other contexts. For instance, to digest the single stranded DNA to which a nucleic acid binding protein is bound. In these contexts an enzyme capable of specifically degrading single stranded DNA in less than 15 minutes and/or which may be essentially irreversibly inactivated at a temperature below 65° C. and/or in less than 15-20 minutes would be advantageous over exonuclease I, RecJ and ExoVII from *E. coli* for the same reasons of time efficiency and gentle processing discussed above.

It has now been found that homologs of the *E. coli* sbcB gene (which encodes for *E. coli* exonuclease I) obtained from species of the genera *Shewanella*, *Halomonas*, *Vibrio*, *Psychromonas* and *Moritella* found in cold water niches, e.g. *Moritella viscose* and *Vibrio wodanis* surprisingly have these advantageous properties.

Therefore, in a first aspect there is provided an exonuclease or an enzymatically active fragment thereof, said exonuclease having the amino acid sequence of SEQ ID No. 1 or an amino acid sequence which is at least about 50% identical thereto, wherein said exonuclease or enzymatically active fragment thereof
(i) is substantially irreversibly inactivated by heating at a temperature of about 55° C. for 10 minutes in a buffer consisting of 10 mM Tris-HCl, pH 8.5 at 25° C., 50 mM KCl and 5 mM $MgCl_2$;
(ii) is substantially specific for single stranded DNA; and
(iii) has a 3'-5' exonuclease activity.

By "at least about 50%" it is meant that the sequence identity may be at least 49%, 49.5% or 49.9%. In preferred embodiments the exonuclease of the invention has an amino acid sequence which is at least 60%, preferably at least 70%, 80%, 85%, 90% or 95%, e.g. at least 98% or 99% or 99.5%, identical to SEQ ID No.1. In other embodiments the exonuclease consists of the amino acid sequence of SEQ ID No 1. Enzymatically active fragments thereof are also provided.

An exonuclease having an amino acid sequence which is at least 50% identical to SEQ ID No.1 may be obtained from a prokaryotic organism found in cold water niches. By "prokaryote" it is meant any organism that lacks a cell nucleus, i.e. any organism from the domains Bacteria and Archaea. Preferably the organism is a bacterium. Preferably the organism is not a eukaryote, e.g. an organism classified in the taxonomic kingdoms Animalia, Plantae, Fungi or Protista. More preferably the organism is selected from the genera *Shewanella*, *Halomonas*, *Vibrio*, *Psychromonas* and *Moritella*.

In certain embodiments an exonuclease having an amino acid sequence which is at least about 50% identical to SEQ ID No.1 may be selected from SEQ ID No. 2 (the SbcB homolog from *Halomonas* sp.), SEQ ID No. 3 (the SbcB homolog from *Vibrio wodanis*), SEQ ID No. 4 (the SbcB homolog from *Psychromonas* sp.) or SEQ ID No. 5 (the SbcB homolog from *Moritella viscosa*).

Thus, in another aspect of the invention there is provided an exonuclease or an enzymatically active fragment thereof, said exonuclease having an amino acid sequence selected from:
(a) SEQ ID No. 1 or an amino acid sequence which is at least 65% identical thereto,
(b) SEQ ID No. 2 or an amino acid sequence which is at least 65% identical thereto,
(c) SEQ ID No. 3 or an amino acid sequence which is at least 65% identical thereto, (d) SEQ ID No. 4 or an amino acid sequence which is at least 65% identical thereto, or (e) SEQ ID No. 5 or an amino acid sequence which is at least 65% identical thereto, wherein said exonuclease or enzymatically active fragment thereof (i) is substantially irreversibly inactivated by heating at a temperature of about 55° C. for 10 minutes in a buffer consisting of 10 mM Tris-HCl, pH 8.5 at 25° C., 50 mM KCl and 5 mM $MgCl_2$;

(ii) is substantially specific for single stranded DNA, and (iii) has a 3'-5' exonuclease activity.

In preferred embodiments of this aspect of the invention, the exonuclease has an amino acid sequence which is at least 70%, preferably at least 80%, 85%, 90% or 95%, e.g. at least 98% or 99% or 99.5%, identical to SEQ ID Nos.1, 2, 3, 4 or 5. In other embodiments the exonuclease consists of an amino acid sequence selected from the group consisting of SEQ ID Nos.1, 2, 3, 4 and 5. Enzymatically active fragments thereof are also provided.

Percentage sequence identity according to the invention can be calculated using any of the widely available algorithms, e.g. using the Clustal W2 multiple sequence alignment program (http://www.ebi.ac.uk/Tools/clustalW2) using default parameters (DNA Gap Open Penalty=15.0; DNA Gap Extension Penalty=6.66; DNA Matrix=Identity; Protein Gap Open Penalty=10.0; Protein Gap Extension Penalty=0.2; Protein matrix=Gonnet; Protein/DNA END-GAP=−1; Protein/DNA GAPDIST=4)

Variants of the abovementioned SEQ ID Nos include amino acid sequences in which one or more amino acids of said SEQ ID Nos have undergone conservative substitution or have been replaced with a modified version of said one or more amino acids or an amino acid which is not naturally occurring, e.g. D isomers of said one or more amino acids. Preferably such substitutions and modifications are silent substitutions and modifications in that the modified forms of the exonucleases of the invention have the same enzymatic and inactivation characteristics as the unmodified forms.

An exonuclease is an enzyme capable of cleaving a nucleotide from one or more termini of a polynucleotide chain, without nucleotide sequence specificity, by hydrolysing an internucleotide phosphodiester bond. Typically exonucleases cleave nucleotides from either the 5' terminus (and so are characterised as 5'-3' exonucleases or as having 5'-3' exonuclease activity) or the 3' terminus (and so are characterised as 3'-5' exonucleases or as having 3'-5' exonuclease activity). In accordance with the invention the exonucleases are 3'-5' exonucleases. In some embodiments the exonucleases of the invention have substantially no 5'-3' exonuclease activity against single stranded DNA, by which it is meant that, at concentrations of 0.1 to 1.0 U/μl in a buffer consisting of 10 mM Tris-HCl, pH 8.5 at 25° C., 50 mM KCl and 5 mM $MgCl_2$, the exonucleases of the invention display little, negligible or essentially no 5'-3' exonuclease activity against single stranded DNA over the course of a 1 hour incubation. Expressed numerically, less than 10%, e.g. less than 5%, 4%, 3%, 2% or 1%, of a single stranded DNA substrate (e.g. about 5 pmol of said substrate, which may for example be an oligodeoxyribonucleotide) under such conditions will be degraded in a 5'-3' direction. Preferably, there will be no detectable 5'-3' exonuclease activity at such concentrations.

The skilled person would be able to devise a suitable assay to measure relative 5'-3' and 3'-5' exonuclease activities. For instance the gel-based exonuclease assay described in the Examples uses a 5' (FAM) labelled single stranded oligodeoxyribonucleotide to monitor degradation from the 3' terminus as such an activity will yield detectable fragments of varying length shortened from the 3' terminus. Degradation from the 5' terminus will yield only single labelled nucleotides. To confirm these results the same assay may alternatively be performed with a 3' labelled single stranded DNA substrate and the opposite gel pattern should be observed.

By "substantially specific for single stranded DNA" it is meant that the activity of the exonuclease of the invention against double stranded DNA is equal to or less than 15% of the activity against an equivalent amount of single stranded DNA under the same conditions, e.g. an enzyme concentration of about 0.1 U/μl and about 5 pmol of nucleic acid substrate in a buffer consisting of 10 mM Tris-HCl, pH 8.5 at 25° C., 50 mM KCl and 5 mM $MgCl_2$ with an incubation time of 10 minutes or less and an incubation temperature of about 30° C. In other embodiments the activity of the exonuclease of the invention against double stranded DNA is equal to or less than 10%, e.g. equal to or less than 8%, 5%, 4%, 3%, 2%, 1%, 0.5%, 0.2%, 0.1% or 0.05%, of the activity against an equivalent amount of single stranded DNA under the same conditions.

In further more specific embodiments "substantially specific for single stranded DNA" also means that the activity of the exonuclease of the invention against single stranded RNA is equal to or less than 15% of the activity against an equivalent amount of single stranded DNA under the same conditions, e.g. an enzyme concentration of about 0.1 U/μl and about 5 pmol of nucleic acid substrate in a buffer consisting of 10 mM Tris-HCl, pH 8.5 at 25° C., 50 mM KCl and 5 mM $MgCl_2$ with an incubation time of 10 minutes or less and an incubation temperature of about 30° C. In other embodiments, the activity of the exonuclease of the invention against single stranded RNA is equal to or less than 10%, e.g. equal to less than 8%, 5%, 4%, 3%, 2%, 1%, 0.5%, 0.2%, 0.1% or 0.05%, of the activity against an equivalent amount of single stranded DNA under the same conditions.

In certain embodiments by "substantially specific for single stranded DNA" it is meant that the exonuclease of the invention degrades single stranded DNA but at concentrations of about 0.1 U/μl in a buffer consisting of 10 mM Tris-HCl, pH 8.5 at 25° C., 50 mM KCl and 5 mM $MgCl_2$, there is little, negligible or essentially no detectable degradation of about 5 pmol of a suitable double stranded DNA substrate (e.g. a double stranded oligodeoxyribonucleotide) over the course of an about 10 minute incubation. Expressed numerically, equal to or less than 15%, e.g. equal to or less than 10%, 8%, 5%, 4%, 2% or 1%, of the suitable double stranded DNA substrate will be degraded under such conditions. Preferably, there will be no detectable degradation of double stranded DNA substrates under such concentrations.

In further more specific embodiments "substantially specific for single stranded DNA" also means that the exonuclease of the invention degrades single stranded DNA but at concentrations of about 0.1 U/μl in a buffer consisting of 10 mM Tris-HCl, pH 8.5 at 25° C., 50 mM KCl and 5 mM $MgCl_2$, there is little, negligible or essentially no detectable degradation of about 5 pmol of a suitable single stranded RNA substrate (e.g. a single stranded oligoribonucleotide) over the course of an about 10 minute incubation. Expressed numerically, equal to or less than 15%, e.g. equal to or less than 10%, 8%, 5%, 4%, 3%, 2% or 1%, of the suitable single stranded RNA substrate will be degraded under such conditions. Preferably, there will be no detectable degradation of single stranded RNA substrates under such concentrations.

In certain embodiments "substantially specific for single stranded DNA" also means that the exonucleases of the invention degrade single stranded DNA but at concentrations of 0.1 to 1.0 U/µl (preferably 0.1 U/µl) in a buffer consisting of 10 mM Tris-HCl, pH 8.5 at 25° C., 50 mM KCl and 5 mM $MgCl_2$, there is little, negligible or essentially no detectable degradation of non-single stranded DNA nucleic acid substrates over the course of a 1 hour incubation. As used herein, the term "non-single stranded DNA nucleic acid substrates", in some embodiments, refers both to double stranded nucleic acids, e.g. double stranded DNA, and single stranded non-DNA nucleic acid, although in preferred embodiments the term refers only to double stranded nucleic acids, e.g. double stranded DNA. Expressed numerically, less than 10%, e.g. less than 5%, 4%, 3%, 2% or 1%, of (e.g. about 5 pmol of) a suitable non-single stranded DNA substrate (i.e. double stranded nucleic acid and/or single stranded non-DNA nucleic acid) under such conditions will be degraded. Preferably, there will be no detectable degradation of non-single stranded DNA nucleic acid substrates (i.e. double stranded nucleic acid and/or single stranded non-DNA nucleic acid) at such concentrations.

The skilled person would easily be able to devise an experiment to make a comparison of relative nuclease activity towards single and double stranded nucleic acid. For instance, an exonuclease under test may be incubated with two samples of a radioactively labelled PCR product (e.g. about 5 pmol of said PCT product), one in which the product has been denatured (i.e. single stranded) and the other in which the product is not denatured (i.e. double stranded) in a buffer consisting of 10 mM Tris-HCl, pH 8.5 at 25° C., 50 mM KCl and 5 mM $MgCl_2$ at a concentration of 0.1 to 1.0 U/µl (preferably 0.1 U/µl) for 10 minutes. The release of acid soluble nucleotides can then be analysed as described in Examples 8 and 9.

Alternatively, an exonuclease under test may be incubated with the abovementioned samples of PCR product (e.g. about 5 pmol of said PCT product) in a buffer consisting of 10 mM Tris-HCl, pH 8.5 at 25° C., 50 mM KCl and 5 mM $MgCl_2$ at a concentration of 0.1 to 1.0 U/µl (preferably 0.1 U/µl) for one hour and then products separated on a suitable, electrophoresis gel e.g. agarose. Activity against single stranded and/or double stranded nucleic acid will be observable by the position of the bands relative to untreated controls.

Another approach measures the increase in fluorescence from oligonucleotides labelled with the fluorophore FAM (fluorescein) at the 5' terminus and with TAMRA at the 3' terminus. The emitted light from FAM is absorbed (quenched) by TAMRA when the two labels are in proximity. The cleavage of the oligonucleotide by the exonuclease under test results in the separation of FAM from TAMRA and an increase in fluorescence from FAM that can be measured in a fluorimeter with excitation wavelength 485 nm and emission wavelength 520 nm. A double stranded substrate can be prepared by mixing the labelled oligonucleotide with a second oligonucleotide that is complementary to the labelled oligonucleotide. Of course other suitable fluorophore pairs may similarly be used. Example 7 describes a suitable assay in greater detail.

Included within the term DNA are modifications thereof which retain a phosphodiester linked deoxyribo-phosphate backbone. Commonly encountered examples of single stranded DNA include oligodeoxyribonucleotide primers and oligodeoxyribonucleotide probes and DNA aptamers. Nucleic identification tags and labels may also be single stranded DNA. Single stranded DNA also arises during reverse transcription, and upon duplex unwinding during DNA replication and DNA transcription. In nucleic acid amplification reactions and reverse transcription reactions single stranded DNA may arise from partially extended primers and any excess of primers that have not been extended and integrated into completely synthesised duplexes.

In further embodiments the exonucleases of the invention have substantially no endonuclease activity. By "substantially no endonuclease activity" it is meant that, at concentrations of 0.1 to 1.0 U/µl in a buffer consisting of 10 mM Tris-HCl, pH 8.5 at 25° C., 50 mM KCl and 5 mM $MgCl_2$, the exonuclease of the invention displays little, negligible or essentially no nuclease activity against a circular single stranded nucleic acid or circular double stranded nucleic acid over the course of a 1 hour incubation. Expressed numerically, less than 10%, e.g. less than 5%, 4%, 3%, 2% or 1%, of (e.g. about 5 pmol of) a single or double stranded nucleic acid substrate will be fragmented (e.g. into oligonucleotides) under such conditions. Preferably, there will be no detectable endonuclease activity at such concentrations.

Enzymatically active fragments and variants of SEQ ID Nos. 1-5 display at least 70%, preferably at least 85%, more preferably at least 95% and most preferably at least 99% of the enzymatic function of the enzymes of SEQ ID Nos. 1-5, respectively. As discussed elsewhere, the activity of an exonuclease can be assessed easily using routine techniques.

In the following discussion, a reference to an exonuclease of the invention is also a reference to an enzymatically active fragment thereof, unless context dictates otherwise.

By "substantially irreversibly inactivated" is meant that on heating to the specified temperature for the specified time and under the specified buffer conditions, the enzyme is at least 90% inactivated, preferably 95%, 98%, 99%, 99.5% or 99.9% inactivated. Percentage inactivation can be conveniently estimated by incubating a suitably labelled (e.g. a 5' FAM labelled) single stranded DNA sample (e.g. a standard PCR primer, for instance a deoxyribonucleic acid primer having the nucleotide sequence of SEQ ID No 21-GCTAACTACCACCTGATTAC) for 30 minutes either with an inactivated exonuclease or with a non-inactivated exonuclease in a suitable buffer (e.g. Tris, HEPES, PBS) at a suitable pH (e.g. pH 7.5) at a suitable temperature (e.g. 30° C.) and in the presence of $Mg^{2+}$ (e.g. 5 mM); separating the reaction products on a suitable gel (e.g. acrylamide/urea gel) by electrophoresis and measuring the relative intensities of fluorescence of the DNA bands under UV light e.g. as shown in Examples 5 and 6. Alternative methods could be devised by the skilled person to measure relative activities of inactivated and non-inactivated exonuclease, in particular a buffer consisting of 10 mM Tris-HCl, pH 8.5 at 25° C., 50 mM KCl and 5 mM $MgCl_2$ may be used.

Even when the temperature of the reaction mixture returns to room temperature, the exonucleases of the invention do not regain activity, i.e. there is substantially no residual activity; specifically, less than 10%, preferably less than 5%, 2%, 1%, 0.5% or 0.1%, most preferably no detectable exonuclease activity remains.

Substantially irreversible inactivation occurs within 10 minutes of incubation in the specified buffer conditions at a temperature of at or about 55° C., e.g. 53 to 57° C. For example in 7, 8 or 9 minutes incubation at about 55° C. As shown in Example 5, in other embodiments the exonuclease of the invention is substantially irreversibly inactivated in the specified buffer conditions at a temperature of at or about 55° C., e.g. 53 to 57° C., within 5 minutes, for example in 2, 3 or 4 minutes. In further embodiments the exonuclease of the invention is substantially irreversibly inactivated in the specified buffer conditions at a temperature of at or about 50° C., e.g. 48 to 53° C., within 10 minutes, for example in 7, 8 or 9 minutes. In still further embodiments the exonuclease of the invention is substantially irreversibly inactivated in the specified buffer conditions at a temperature of at or about 50° C., e.g. 48 to 53° C., within 5 minutes, for example in 2, 3 or 4 minutes. The exonucleases represented by SEQ ID Nos.1 and 4 and variants thereof are examples of these latter embodiments.

In other embodiments substantially irreversible inactivation of the exonuclease of the invention occurs within 1 minute of incubation in the specified buffer conditions at a temperature of at or about 80° C., e.g. 70 to 90° C., 75 to 85° C., 78 to 82° C. or 79 to 81° C. For example in an incubation of at least about 30, 40, 50 or 55 seconds at about 80° C.

When in use, the exonuclease of the invention may be substantially irreversibly inactivated at lower temperatures or over shorter time periods depending on the conditions in which the enzyme is being used, e.g. at 55° C. for 5 minutes or at 50° C. for 5 to 15 minutes, e.g. 10 to 15 minutes but, in accordance with the invention, heating for 10 minutes at about 55° C. in the specified buffer conditions must be sufficient to substantially irreversibly inactivate the enzyme. It will be readily apparent to the skilled person that adjustments to one of these two parameters can be compensated for by adjusting the other. For instance increasing the inactivation temperature might permit the duration of incubation to be reduced. Conversely, increasing the duration of incubation might permit a lower inactivation temperature to be used. Of course, as is also readily apparent to the skilled person and shown in the Examples, when the exonucleases of the invention are used in the methods of the invention, durations of incubation longer than ten minutes may be used and inactivation temperatures greater than about 55° C. may be used, if practical (e.g. inactivation could take place at 80° C. for 1 minute, 60° C. for 5 to 10 minutes, 55° C. for 15 minutes or 50° C. for 15 minutes). However, to be in accordance with the invention, an exonuclease must show substantial inactivation if incubated at a temperature of at or about 55° C. for 10 minutes in the specified buffer conditions.

Inactivation temperatures and times for an exonuclease of the invention should be assessed by incubating the exonuclease in buffer consisting of 10 mM Tris-HCl, pH 8.5 at 25° C., 50 mM KCl and 5 mM $MgCl_2$. The exonuclease should be present at about 0.1 to 1.0 U/µl, preferably 0.1 to 1.5 U/µl, 0.1 to 5 U/µl or 0.1 U/µl to 10 U/µl.

In most preferred embodiments an exonuclease of the invention may have (or consist of) an amino acid sequence of SEQ ID No. 1, SEQ ID No. 2, SEQ ID No. 3, SEQ ID No. 4, or SEQ ID No. 5.

In another aspect of the invention there is provided an exonuclease having (or consisting of) an amino acid sequence of SEQ ID No. 1, SEQ ID No. 2, SEQ ID No. 3, SEQ ID No. 4, or SEQ ID No. 5. Being defined entirely by amino acid sequence means the particular functional features described above do not necessarily apply to this aspect. Nevertheless, as shown in the Examples, each of these specific exonucleases finds utility in the methods of the invention described herein.

The exonucleases of the invention may be provided in a modified form, e.g. as a fusion protein with an amino acid motif useful in a process for the isolation, solubilisation and/or purification or identification of the exonucleases. Such amino acid motifs (also known as protein tags) include, but are not limited to polyhistidine (His) tags. Examples of polyhistidine tagged exonucleases of the invention are recited in SEQ ID Nos 11 to 15. Such enzymes form a further aspect of the invention.

Further modifications include the introduction of small chemical groups to available atoms of the polypeptide, e.g. protecting groups for the N and C termini or the R-groups of non-essential amino acid residues within the polypeptide. In other embodiments the exonucleases of the invention may be provided immobilised on a solid support, e.g. a solid support selected from particles, pellets, beads, sheets, gels, filters, membranes, fibres, capillaries, chips, micro titre strips, slides, tubes, plates or wells etc. Preferably the support is magnetic (preferably paramagnetic or superparamagnetic) e.g. magnetic particles, for instance magnetic beads and pellets. Still further modified forms include dimers or trimers of the exonucleases of the invention. Such entities may be homogeneous or heterogeneous in their monomer composition.

The invention also provides nucleic acid molecules encoding the exonucleases of the invention and enzymatically active fragments thereof. Nucleotide sequences corresponding to the amino acid sequences of SEQ ID Nos. 1 to 5 are disclosed in SEQ ID Nos. 6 to 10, respectively, and the nucleic acids of the invention may comprise these nucleotide sequences. Nucleotide sequences corresponding to the amino acid sequences of SEQ ID Nos. 11 to 15 are disclosed in SEQ ID Nos. 16 to 20, respectively, and the nucleic acids of the invention may comprise these nucleotide sequences. Degeneracy of the genetic code means that each of SEQ ID Nos. 6 to 10 and 16 to 20 are each only one of many possible nucleotide sequences encoding the amino acid sequences of SEQ ID Nos. 1 to 5 and 11 to 15, respectively. Accordingly, the invention extends to nucleic acid molecules comprising nucleotide sequences which are degenerate versions of SEQ ID Nos. 6 to 10 and 16 to 20. The nucleic acid molecules of the invention may be nucleic acid vectors, e.g. cloning vectors or expression vectors. Preferred vectors are plasmids compatible with bacterial and/or yeast cells.

The enzymatic activities and inactivation characteristics of the exonucleases of the invention make such enzymes especially suited for the removal of single stranded DNA from samples containing biological macromolecules, in particular, the products of a nucleic acid amplification or reverse transcription reactions, e.g. double stranded DNA, RNA and DNA:RNA duplexes.

Thus, in a further aspect there is provided a method of removing single stranded DNA from a sample, preferably a sample of biological macromolecules, said method comprising contacting the sample with an exonuclease as defined above.

The exonucleases of the invention are thus used to degrade single stranded DNA present in the sample. In particular, the method involves contacting the sample with an exonuclease of the invention under conditions which permit the digestion of at least a portion of the single stranded DNA present in the sample and then optionally heating the sample to inactivate said exonuclease. These steps of digestion and inactivation will typically be incubations and are described herein, in particular in the Examples. Suitable incubation conditions to achieve digestion of single stranded DNA in a sample are known in the art and may conveniently comprise incubation at 10 to 45° C., e.g. at or around 20 to 40° C. or 30° C. for 1 to 30 minutes, e.g. 1 to 20 minutes, 1 to 15 minutes or 1 to 10 minutes, preferably around 5 minutes or less. If a temperature at the higher end of these ranges is used, the duration of incubation may be at the lower end of these ranges, and vice versa. Inactivation conditions may be based on the discussion of such parameters given above.

By "removing single stranded DNA" it is meant that the amount of single stranded DNA in the sample is reduced to some extent. Encompassed are embodiments in which the amount of single stranded DNA is reduced below detectable levels, as well as embodiments in which the amount of single stranded DNA is reduced to a smaller but still detectable amount. Preferably the amount of single stranded DNA is reduced sufficiently to improve the quality of the sample as defined by the relevant context, e.g. its use in a nucleic acid sequence analysis reaction. Expressed numerically the amount of single stranded DNA in a sample may be reduced by at least 10% e.g. by at least, 20%, 30%, 40%, 50%, 60%, 70%, 80%, 85%, 90%, 95% or 99% or by 100%. In practical terms, to remove single stranded DNA from a sample, or to reduce the amount of single stranded DNA in a sample, in accordance with the invention, is to degrade at least a portion of the single stranded DNA present in a sample. The term "at least a portion" should be construed in line with the foregoing.

In a preferred embodiment, the sample is a preparation containing a nucleic acid of interest (e.g. DNA, RNA, PNA), e.g. a double stranded nucleic acid or a DNA:RNA duplex; a protein of interest, for example a recombinantly produced protein of interest, e.g. an enzyme; a carbohydrate polymer; or a lipid. Alternatively the protein of interest may be an analyte or other protein which it is desired to purify from a starting material. The protein of interest may be an antibody or antibody fragment. The protein (e.g. antibody) could be useful in diagnostic or therapeutic methods. Thus, the method above described may be used in order to ensure that the diagnostic or therapeutic protein is free from contaminating single stranded DNA so that it may be safe to administer. The protein of interest may be a DNA binding protein or other protein which associates with nucleic acid, particularly single stranded DNA in solution. Accordingly, the preparation may be derived from a cell lysate or tissue sample or body fluid and/or may be the product of a nucleic acid amplification or a reverse transcription reaction. The method of the invention can therefore be considered as encompassing a method for refining or enriching a sample comprising double stranded DNA, RNA and/or DNA:RNA duplexes by removing single stranded DNA. Such a method would comprise contacting the sample with an exonuclease as defined above.

In preferred embodiments the sample is the product of a nucleic acid amplification reaction or the product of a reverse transcription reaction and thus the invention provides a method of removing single stranded DNA from the product of a nucleic acid amplification reaction or the product of a reverse transcription reaction, said method comprising the use of an exonuclease as defined above. The method will typically comprise contacting the product of a nucleic acid amplification reaction or the product of a reverse transcription reaction with an exonuclease as defined above.

The exonucleases of the invention are thus used to degrade single stranded DNA present in the product of a nucleic acid amplification reaction or the product of a reverse transcription reaction. In particular, the method involves contacting the product of a nucleic acid amplification reaction or the product of a reverse transcription reaction with an exonuclease of the invention under conditions which permit the digestion of at least a portion of the single stranded DNA present therein and optionally heating the mixture to inactivate said exonuclease. The features of the steps of digestion and inactivation are described above.

The term "nucleic acid amplification reaction" refers to any in vitro means for increasing the number of copies of a target sequence of nucleic acid or its complementary sequence. Preferably, the amplification methods will involve "thermal cycling", i.e. involving high temperature cycling. Amplification methods include, but are not limited to, PCR and modifications thereto, 3SR, SDA, LAR or LCR and LAMP and modifications thereto. PCR and LCR and their modifications are thermal cycling methods. Methods may result in a linear or exponential increase in the number of copies of the target sequence. "Modifications" encompass, but are not limited to, real-time amplification, quantitative and semi-quantitative amplification, competitive amplification, hot start PCR, and so on. Reverse transcription maybe combined with other nucleic acid amplification reactions as appropriate.

Preferably the nucleic acid amplification method is a method based on the use of oligonucleotide primers as initiators of nucleic acid synthesis, e.g. the PCRs, LAR, SDA, LAMP and NASBA.

The target nucleic acid for the amplification reaction may be DNA or RNA depending on the selected amplification method. For example, for PCR the target is DNA, although when combined with a reverse transcription step the target can be considered to be an RNA sequence. 3SR amplifies RNA target sequences directly.

"Reverse transcription" is a process in which a single strand RNA template is transcribed into a complementary single stranded DNA (cDNA). These nucleic acid strands exist as a duplex until denaturing conditions are applied. The single stranded DNA may also then be used as a template to form double stranded cDNA in a so-called second strand cDNA synthesis step. Some nucleic acid polymerase enzymes are capable of producing the first cDNA strand and synthesising the second strand to form double stranded cDNA and others are specific for just one of the two steps.

A "product of a nucleic acid amplification reaction" is therefore considered to comprise essentially all of the components obtained directly from the final amplification step of the reaction in question. Other components may be added or certain of the components may undergo some modification or processing, but essentially none of the components, or at least none of the nucleic acid components, will have been removed. Preferably the product of a nucleic acid amplification reaction is the direct product of the final amplification step; however, it might also be preferable for the product of a nucleic acid amplification reaction to undergo a treatment to effect the dephosphorylation of any unincorporated NTPs, e.g. a treatment with an alkaline phosphatase, preferably a thermolabile alkaline phosphatase, for instance the heat-labile shrimp alkaline phosphatase (SAP), prior to treatment with the exonucleases of the invention. References to NTPs herein specifically include references to dNTPs unless context dictates otherwise. In other embodiments the dephosphorylation of NTPs may take place after treatment with the exonucleases of the invention, or at the same time. An advantageous recombinant SAP is available from Arctic-Zymes™ AS.

Accordingly, the above defined methods of removing single stranded DNA from the product of a nucleic acid amplification reaction or the product of a reverse transcription reaction may further comprise using an alkaline phosphatase, preferably a thermolabile alkaline phosphatase, to dephosphorylate any unincorporated NTPs prior to, at the same time as, or after using the exonuclease to remove single stranded DNA, i.e. prior to, at the same time as, or after the step of contacting the product of the amplification or reverse transcription reaction with the exonuclease. In particular, using an alkaline phosphatase in these methods involves contacting the alkaline phosphatase with the product of the amplification/reverse transcription reaction prior to, at the same time as, or after contacting said product with the exonuclease of the invention.

Preferably, any alkaline phosphatase treatment may precede any heat inactivation step. In embodiments where it does not, a further heat inactivation step may be used.

In structural terms, a product of a nucleic acid amplification reaction in accordance with the invention will comprise the template nucleic acid and NTPs, and typically in addition a polymerase and at least one oligonucleotide primer, which may be partially extended. Also typically the bulk of the product will be made up of a suitable nucleic acid amplification buffer, e.g. a buffer as exemplified herein. Preferred products of nucleic acid amplification reactions comprise all of these elements.

In these embodiments the treatments of the invention remove (i.e. degrade), as appropriate, excess non-extended DNA primers, partially extended DNA primers, single stranded DNA template, single stranded DNA amplicons, denatured DNA amplicons and so on.

A "product of a reverse transcription reaction" should be construed in accordance with the definition of a product of a nucleic acid amplification reaction, keeping in mind that a reverse transcription reaction might have only one RNA-dependent nucleic acid polymerisation step and, optionally, may have one or more second strand cDNA synthesis step(s). Preferably the product of a reverse transcription reaction to which the exonuclease of the invention is applied is a product comprising cDNA:RNA duplexes and/or double stranded cDNA.

In a further aspect of the invention there is provided a method of nucleic acid amplification, said method comprising a step subsequent to the final amplification step of using an exonuclease as defined herein to remove single stranded DNA from the product of the nucleic acid amplification reaction. Typically, the step of removing single stranded DNA comprises contacting the product of the nucleic acid amplification reaction, preferably the direct product of the final amplification step, with an exonuclease as defined herein. Said method may further comprise a step, subsequent to the final amplification step, of using an alkaline phosphatase, preferably a thermolabile alkaline phosphatase, to dephosphorylate any unincorporated NTPs in the product of the nucleic acid amplification reaction prior to, at the same time as, or after using the exonuclease to remove single stranded DNA, i.e. prior to, at the same time as, or after the step of contacting the product of the amplification reaction with the exonuclease. In particular, using an alkaline phosphatase in these methods involves contacting the alkaline phosphatase with the product of the amplification reaction prior to, at the same time as, or after contacting said product with the exonuclease of the invention.

In a further aspect of the invention there is provided a method of reverse transcription, said method comprising a step subsequent to the final reverse transcription step, and/or, if present, the final second strand cDNA synthesis step, of using an exonuclease as defined herein to remove single stranded DNA from the product of the reverse transcription reaction. Typically, the step of removing single stranded DNA comprises contacting the product of the reverse transcription reaction, preferably the direct product of the final reverse transcription step, and/or, if present, the direct product of the final second strand cDNA synthesis step, with an exonuclease as defined herein. Preferably such products will be products comprising cDNA:RNA duplexes and/or double stranded cDNA. Said method may further comprise a step, subsequent to the final reverse transcription step, and/or, if present, the final second strand cDNA synthesis step, of using an alkaline phosphatase, preferably a thermolabile alkaline phosphatase, to dephosphorylate any unincorporated NTPs in the product of the reverse transcription reaction prior to, at the same time as, or after using the exonuclease to remove single stranded DNA, i.e. prior to, at the same time as, or after the step of contacting the product of the reverse transcription reaction with the exonuclease. In particular, using an alkaline phosphatase in these methods involves contacting the alkaline phosphatase with the product of the reverse transcription reaction prior to, at the same time as, or after contacting said product with the exonuclease of the invention.

The exonucleases of the invention are thus used to degrade single stranded DNA present in the product of a nucleic acid amplification reaction or the product of a reverse transcription reaction. In particular, the methods involve contacting the product of a nucleic acid amplification reaction or the product of a reverse transcription reaction with an exonuclease of the invention under conditions which permit the digestion of at least a portion of the single stranded DNA present therein and optionally heating the mixture to inactivate said exonuclease. The features of the steps of digestion and inactivation are described above. Preferably, any alkaline phosphatase treatment may precede the heat inactivation step. In embodiments where it does not, a further heat inactivation step may be used.

It is commonplace to combine reverse transcription with one or more nucleic acid amplification reactions. It is also commonplace to combine a plurality of nucleic acid amplification reactions into a single multistage protocol. It will be immediately apparent that each part of these multistage protocols may be considered a method of nucleic acid amplification or method of reverse transcription of the invention in their own right and thus the exonuclease of the invention may be used in accordance with the invention in any or all parts of such multistage protocols.

In a further aspect of the invention there is provided a method of optimising nucleic acid sequence analysis, said method comprising using an exonuclease as defined herein to remove single stranded DNA from the sample to be analysed. The method will typically comprise contacting the sample with an exonuclease as defined herein.

Preferably in this aspect the sample is the product of an amplification reaction or the product of a reverse transcription reaction, e.g. as defined above, but other samples may be used, e.g. those prepared directly from biological materials or which contain biological materials, e.g. microorganisms, body fluids, eukaryotic cells, cultures, tumours and tissues. Preferably the sample will be at least partially purified nucleic acid preparations of the aforementioned samples, e.g. DNA and RNA preparations.

The term "optimisation" encompasses an improvement in the accuracy and/or sensitivity of the sequence analysis of nucleic acids (e.g. the products of nucleic acid amplification or reverse transcription reactions). In accordance with the invention this improvement is, at least in part, a result of the removal of single stranded DNA which may interfere and/or compete with the sequence analysis reactions, reducing their effectiveness against the target template, and/or which are themselves sequenced and so contribute to the background noise in the system, thus making analysis of the outputted signals less sensitive.

In a further aspect of the invention there is provided a method of nucleic acid sequence analysis, said method comprising a step of sample preparation prior to the analysis step(s) of using an exonuclease as defined herein to remove single stranded DNA from the sample to be analysed. The method will typically comprise contacting the sample with an exonuclease as defined herein.

In these latter aspects where the sample is a product of an amplification reaction or the product of a reverse transcription reaction, the sample may also undergo treatment with an alkaline phosphatase, preferably a thermolabile alkaline phosphatase, to dephosphorylate any unincorporated NTPs. Accordingly, the above defined method of nucleic acid sequence analysis may comprise a further sample preparation step of using an alkaline phosphatase to dephosphorylate any incorporated NTPs prior to, at the same time as, or after using the exonuclease to remove single stranded DNA, i.e. prior to, at the same time as, or after the step of contacting the sample to be analysed with the exonuclease. In particular, using an alkaline phosphatase in these methods involves contacting the alkaline phosphatase with the sample to be analysed prior to, at the same time as, or after contacting said product with the exonuclease of the invention.

In these latter aspects the exonucleases of the invention are thus used to degrade single stranded DNA present in the sample to be analysed, e.g. those samples discussed above. In particular, the method involves contacting the sample with an exonuclease of the invention under conditions which permit the digestion of at least a portion of the single stranded DNA present therein and optionally heating the mixture to inactivate said exonuclease. The features of the steps of digestion and inactivation are described above. Preferably, any alkaline phosphatase treatment may precede the heat inactivation step. In embodiments where it does not, a further heat inactivation step may be used.

Preferably in these latter aspects the nucleic acid sequence analysis is a sequencing technique, e.g. the Sanger dideoxynucleotide sequencing method or a "next generation" or "second generation" sequencing approach (for instance, those involving pyrosequencing, reversible terminator sequencing, cleavable probe sequencing by ligation, non-cleavable probe sequencing by ligation, DNA nanoballs, and real-time single molecule sequencing) or an oligonucleotide hybridisation probe based approach in which the presence of a target nucleotide sequence is confirmed by detecting a specific hybridisation event between a probe and its target.

The nucleic acid sequence analysis may provide information useful in the genotyping of an organism, e.g. for classification, identification, quantification, prognostic, diagnostic and/or forensic applications, or useful in the profiling of the transcriptome of a cell or group of cells, e.g. for prognostic, diagnostic and/or research applications. The invention encompasses the use of the exonucleases defined herein in the methods described here for such purposes.

The invention also provides the use of an exonuclease as defined herein to remove single stranded DNA from a sample, and more specifically in the methods described herein.

Where appropriate, the exonucleases of the invention may be isolated from a natural source, e.g. isolated from extracts of the organisms described above, or produced recombinantly in a host cell and isolated and purified therefrom. The exonucleases of the invention may therefore be recombinant enzymes, in particular isolated recombinant enzymes. In certain embodiments the exonuclease is produced by recombinant techniques in a host cell that is not, or not from, an organism which is the same as that in which the exonuclease is found naturally, i.e. a heterologous host cell. Alternatively, a cell-free expression system can be used for production of the exonuclease. These approaches may result in an altered glycosylation pattern.

A method for the isolation and purification of an exonuclease or an enzymatically active fragment thereof as described herein represents a further aspect of the present invention. Thus, in this aspect the invention provides such a method, said method comprising culturing cells in which the exonuclease is expressed and subsequently separating the exonuclease from said cells and/or the media in which said cells have been cultured. Preferably the method comprises expressing said exonuclease in a suitable heterologous host cell (e.g. *E. coli*, *Bacillus* and *Pichia pastoris*), and subsequently separating the exonuclease from said host cells and/or the media in which said cells have been cultured. Expression of said exonuclease can be achieved by incorporating into a suitable host cell an expression vector encoding said nuclease, e.g. an expression vector comprising a nucleic acid molecule encoding any of the amino acid sequences of SEQ ID NOs. 1 to 5 or 11 to 15, for instance a nucleic acid molecule comprising the nucleotide sequence of any of SEQ ID NOs. 6 to 10 or 16 to 20. Host cells comprising these expression vectors and nucleic acid molecules are encompassed by the invention.

The exonuclease enzyme may be separated, or isolated, from the host cells/culture media using any of the purification techniques for protein known in the art and widely described in the literature or any combination thereof. Such techniques may include for example, precipitation, ultrafiltration, dialysis, various chromatographic techniques, e.g. gel filtration, ion-exchange chromatography, affinity chromatography, electrophoresis, centrifugation etc. As discussed above, the exonuclease of the invention may be modified to carry amino acid motifs or other protein or non-protein tags, e.g. polyhistidine tags, to assist in isolation, solubilisation and/or purification or identification. Examples of polyhistidine tagged exonucleases of the invention are recited in SEQ ID Nos 11 to 15.

Likewise an extract of host cells may also be prepared using techniques well known in the art, e.g. homogenisation, freeze-thawing etc. and from this extract the exonuclease of the invention can be purified.

Freezer storage of the exonuclease of the invention may be conveniently achieved with a storage buffer of 5 mM Tris/HCl, pH 7.5 (at 25° C.), 250 mM NaCl, 5 mM MgCl$_2$, 0.25 mM EDTA, 50% glycerol, although other buffers may be used.

The present invention also provides kits which comprise at least an exonuclease according to the invention or a nucleic acid encoding an exonuclease according to the invention. The kits may also contain some or all of the necessary reagents, buffers, enzymes etc. to carry out nucleic acid amplification and/or reverse transcription and/or sequence analysis reactions. More particularly, the kits may contain nucleotide triphosphates (including dNTPaS for SDA), oligonucleotide primers, oligonucleotide probes, reverse transcriptases, DNA polymerases, preferably a thermostable polymerase such as Taq polymerase or Bst polymerase (and hot-start versions thereof) or, in the case of LAR, a DNA ligase (preferably a thermostable DNA ligase such as Ampligase® or that disclosed in U.S. Pat. No. 6,280,998 which is isolated from *Pyrococcus furiosus*) an alkaline phosphatase, preferably a thermolabile alkaline phosphatase (e.g. SAP), or a restriction enzyme (preferably a thermostable restriction enzyme such as BsoB1). Kits comprising an exonuclease of the invention and an alkaline phosphatase, preferably a thermolabile alkaline phosphatase (e.g. SAP), e.g. any of those disclosed herein are of note.

The present invention also provides compositions comprising an exonuclease of the invention and one or more of the necessary reagents to carry out nucleic acid amplification and/or reverse transcription and/or sequence analysis reactions and methods, e.g. those components described above. Typically such compositions will be aqueous and buffered with a standard buffer such as Tris, HEPES, etc. The present invention also provides compositions comprising an exonuclease of the invention in a buffer.

The invention will now be described by way of non-limiting Examples with reference to the following figures in which:

FIG. 1 shows the amino acid and nucleotide sequences of *Shewanella* sp. exonuclease (SEQ ID No 1 and SEQ ID No. 6, respectively).

FIG. 2 shows the amino acid and nucleotide sequences of *Halomonas* sp. exonuclease (SEQ ID No 2 and SEQ ID No. 7, respectively).

FIG. 3 shows the amino acid and nucleotide sequences of *Vibrio wodanis* exonuclease (SEQ ID No 3 and SEQ ID No. 8, respectively).

FIG. 4 shows the amino acid and nucleotide sequences of *Psychromonas* sp. exonuclease (SEQ ID No 4 and SEQ ID No. 9, respectively).

FIG. 5 shows the amino acid and nucleotide sequences of *Moritella viscosa* (SEQ ID No 5 and SEQ ID No. 10, respectively).

FIG. 6 shows an alignment of SEQ ID Nos 1-5 with the amino acid sequence of *E. coli* exonuclease I (SEQ ID No 22) generated with ClustalW Multiple alignment tool. The consensus sequence is shown at the bottom. *, identical residues in all sequences; highly conserved residues among the sequences; weakly conserved residues among the sequences.

FIG. 7 shows the amino acid and nucleotide sequences of a His-tagged version of *Shewanella* exonuclease (SEQ ID No 11 and SEQ ID No. 16, respectively).

FIG. 8 shows the amino acid and nucleotide sequences of a His-tagged version of *Halomonas* exonuclease (SEQ ID No 12 and SEQ ID No. 17, respectively).

FIG. 9 shows the amino acid and nucleotide sequences of a His-tagged version of *Vibrio wodanis* exonuclease (SEQ ID No 13 and SEQ ID No. 18, respectively).

FIG. 10 shows the amino acid and nucleotide sequences of a His-tagged version of *Psychromonas* exonuclease (SEQ ID No 14 and SEQ ID No. 19, respectively).

FIG. 11 shows the amino acid and nucleotide sequences of a His-tagged version of *Moritella viscosa* exonuclease (SEQ ID No 15 and SEQ ID No. 20, respectively).

FIG. 12 shows images of a number of polyacrylamide gels on which the products of a variety of reactions between a single stranded DNA oligonucleotide and a variety of heat-labile (HL) exonucleases have been separated, thus indicating activity of the enzyme against single stranded DNA. Buffer conditions as described in Example 2. (−) Cont—negative control. FIG. 12a: HL-ExoI (Ha) activity at different temperatures (20 to 37° C.) at different time intervals (1 to 10 minutes). Different dilution factors depending on incubation time (4× for 1 to 5 minutes and 10× for 10 minutes). FIG. 12b: HL-ExoI (Ps) activity at different temperatures (20 to 37° C.) at different time intervals (1 to 10 minutes). Different dilution factors depending on incubation time (3× for 1 minute, 8× for 5 minutes and 12× for 10 minutes). FIG. 12c: HL-ExoI (Sh) activity at different temperatures (20 to 37° C.) at different time intervals (1 to 10 minutes). Different dilution (4× for 1 minute and 5 minutes and 10× for 10 minutes). FIG. 12d: HL-ExoI (Mv) activity at different temperatures (20 to 37° C.) at different time intervals (1 to 10 minutes). Different dilution factors depending on incubation time (1× for 1 minute and 5 minutes and 2× for 10 minutes).

Figure 13:
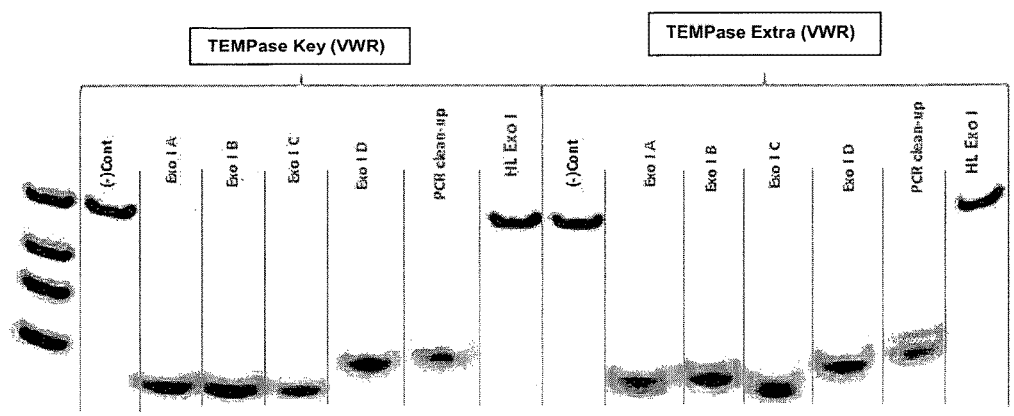

FIG. 13 shows an image of a polyacrylamide gel on which the products of a variety of reactions between a single stranded DNA oligonucleotide and a variety of heat treated exonucleases have been separated, thus indicating activity of the enzymes against single stranded DNA. Buffer conditions as described in Example 3. (−) Cont—negative control. Four commercially available *E. coli* ExoI enzymes (ExoI A-D), one commercially available enzymatic PCR clean-up kit and HL-ExoI (Sh) were compared in terms of ease of thermal inactivation. Samples were incubated for 1 min at 80° C. before substrate addition and residual activity incubation.

Figure 14B:
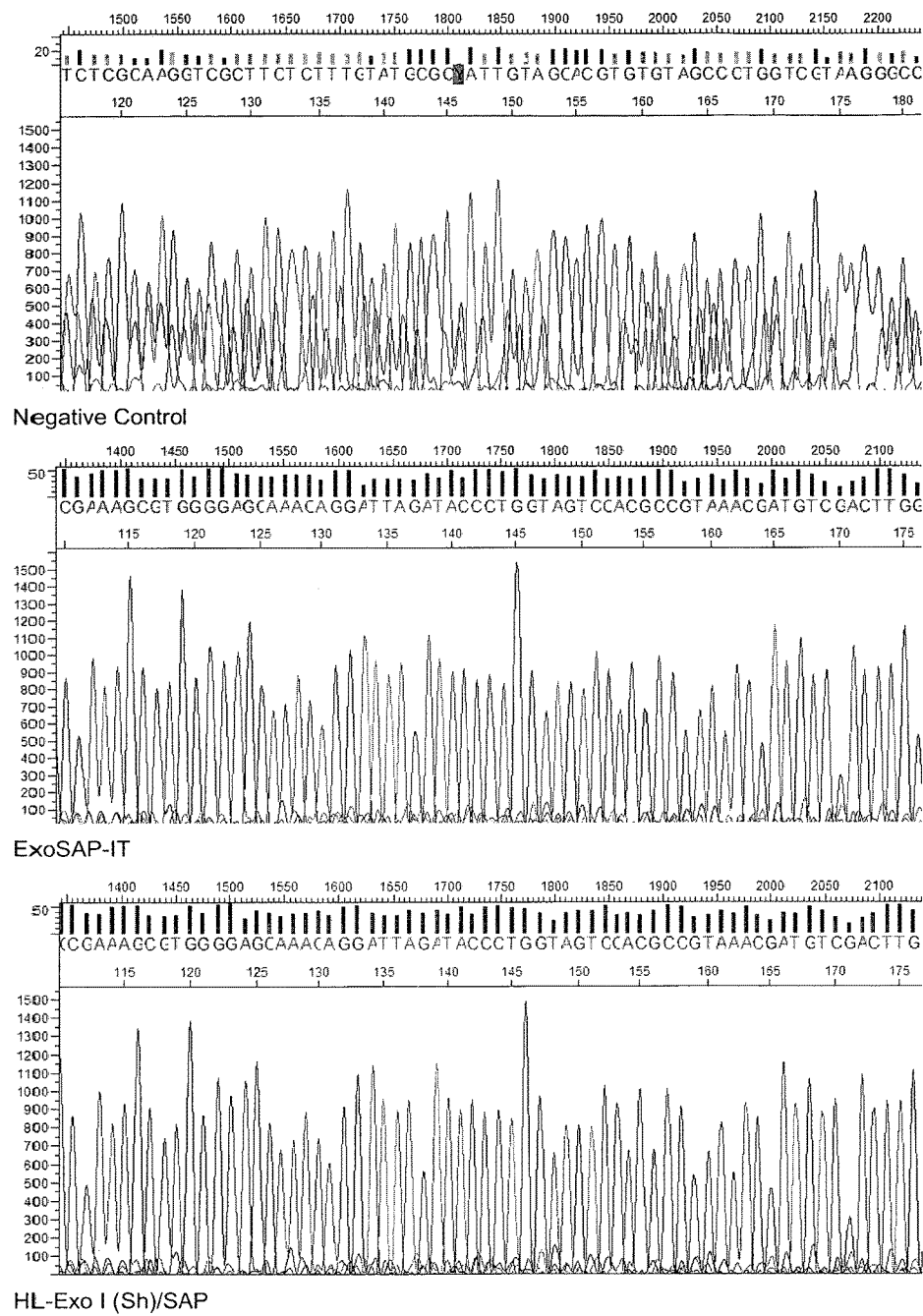
Figure 14C:
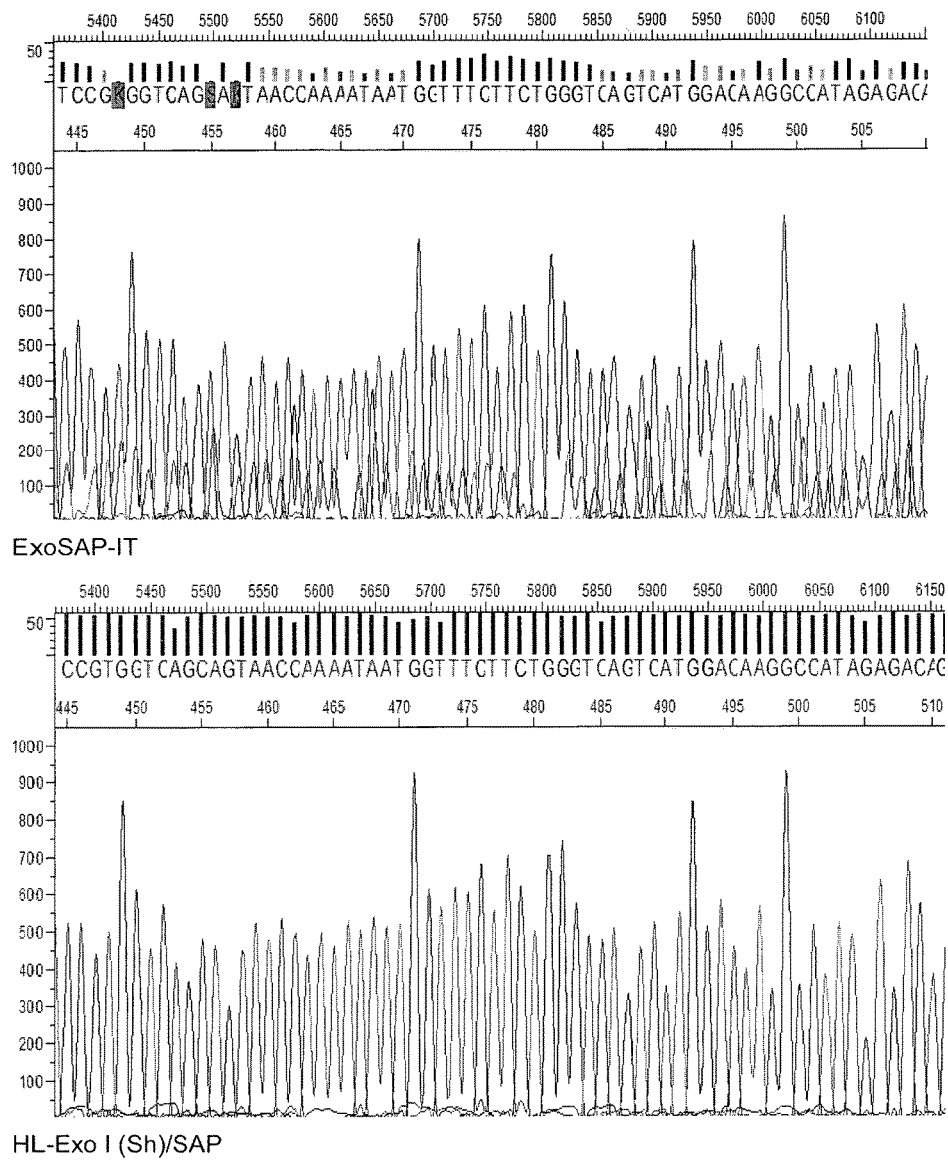
Figure 15A:
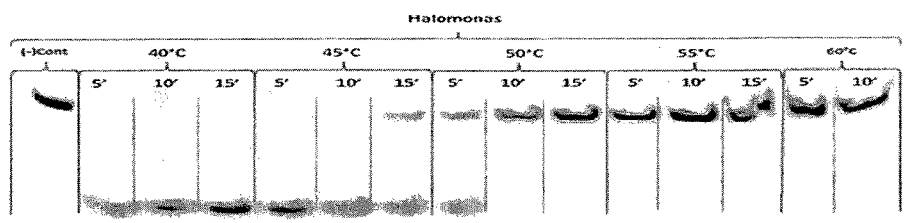
Figure 15B:
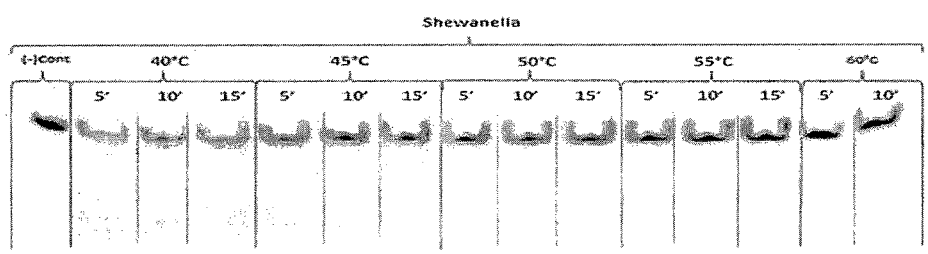
Figure 15C:
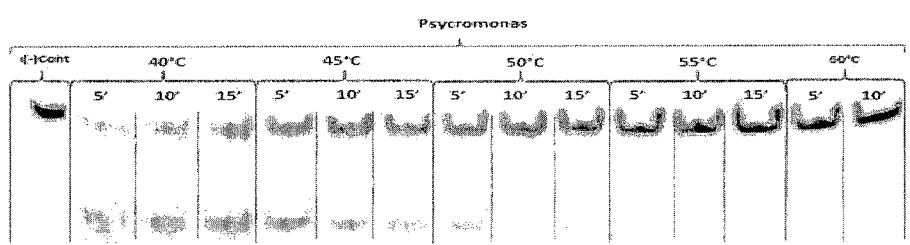
Figure 15D:
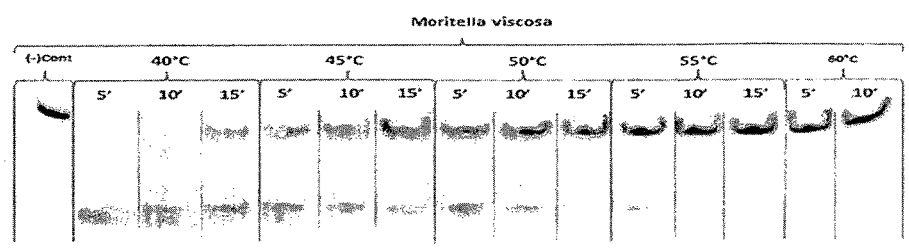
Figure 15E:
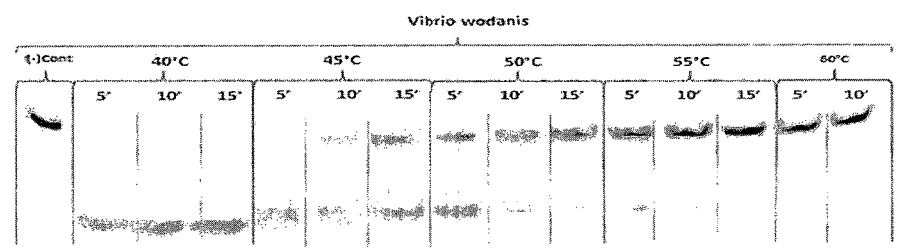
Figure 16A:
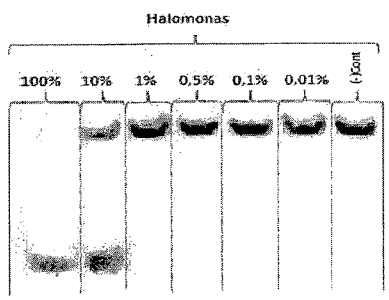
Figure 16B:
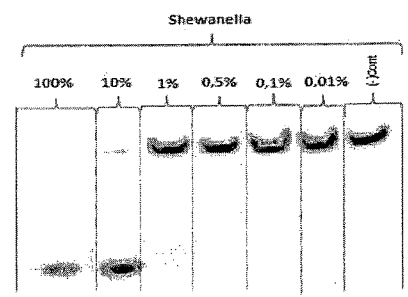
Figure 16C:
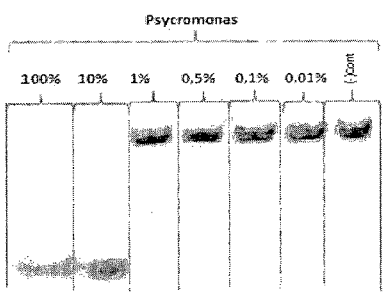
Figure 16D:
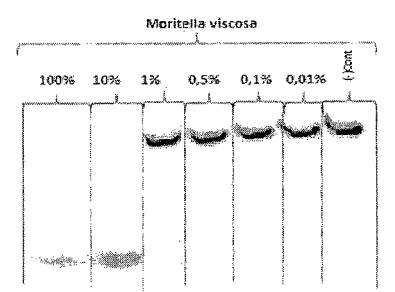
Figure 16E:
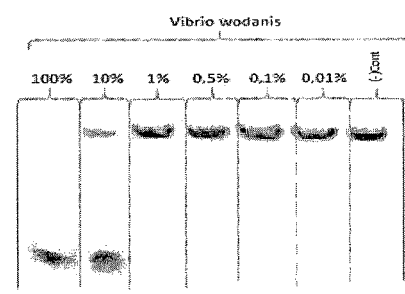

FIG. 14 shows representative sequencing results from the sequencing reactions of Example 4. FIG. 14a: reaction based on GoTaq PCR buffer—ExoSAP-IT corresponds the 30 minutes protocol described in Example 4 and HL-ExoI (Sh)/SAP corresponds to the 5 minutes protocol described in Example 4. FIG. 14b: as FIG. 14a, respectively, although TEMPase Extra PCR buffer used in place of GoTaq. FIG. 14c: as FIG. 14a although ExoSAP-IT and HL-ExoI (Sh)/SAP corresponds to the 5 min protocol described in Example 4.

FIG. 15 shows images of a number of polyacrylamide gels on which the products of a variety of reactions between single stranded DNA oligonucleotides and HL-ExoI of the invention have been separated, thus indicating the residual activity of the enzyme following heat treatment against single stranded DNA. Buffer conditions as descried in Example 5. 15a: HL-ExoI (Ha); 15b: HL-ExoI (Sh); 15c: HL-ExoI (Ps); 15d: HL-ExoI (Mv); 15e: HL-ExoI (Vw). (−) Cont—negative control. Samples were incubated for 5 minutes, 10 minutes or 15 minutes at different temperatures (40° C.-60° C.) prior to substrate addition and residual activity incubation, which was performed at 30° C. for 30 minutes, and then for 2 minutes at 95° C.

FIG. 16 shows images of a number of polyacrylamide gels on which the products of a variety of reactions between single stranded DNA oligonucleotides and HL-ExoI of the invention have been separated, thus indicating the activities of the test ExoI against single stranded DNA at increasing dilution. Buffer conditions as descried in Example 6. 16a: HL-ExoI (Ha); 16b: HL-ExoI (Sh); 16c: HL-ExoI (Ps); 16d: HL-ExoI (Mv); 16e: HL-ExoI (Vw). (−) Cont—negative control. 100%—undiluted enzyme, 10%—enzyme diluted 10 times, 1%—enzyme diluted 100 times, 0.1%—enzyme diluted 1000 times, 0.01%—enzyme diluted 10,000 times. Samples were incubated for 30 minutes at 30° C., and then for 2 minutes at 95° C.

Figure 17:
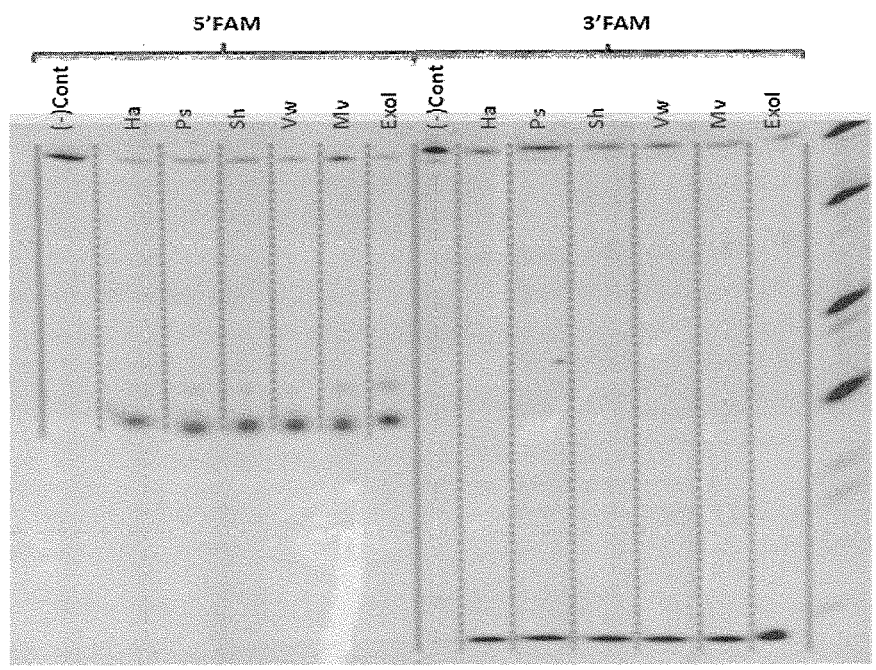

FIG. 17 shows the 3' to 5' directionality of HL-ExoI (Ha, Ps, Sh, Vw, Mv) as well as for *E. coli* ExoI. Assay conditions are described in Example 11. When FAM was labeled at the 5' end, a ladder of partial faint and intense intermediate product bands were seen indicating the ExoI degrading the substrate from the 3' end. When the oligo was FAM-labeled at the 3' end, the fluorophore was immediately cut off, generating only the 3'FAM monomer. (−) Cont—negative control. ExoI—*E. coli* ExoI.

Figure 18:
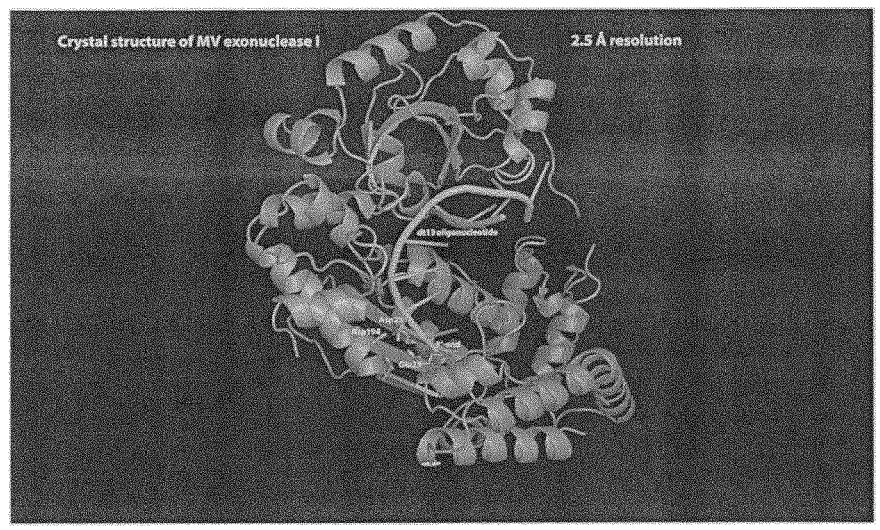

FIG. 18 shows the crystal structure of HL-ExoI (Mv) in complex with ssDNA (dT13) at a resolution of 2.5 Å. Experimental set-up is described in Example 12. Active site residues Asp23, Glu25 and Asp194 are indicated as sticks. In the three-dimensional structure of the HL-ExoI (Mv) the 3'-end of the dT13 is clearly located in the active site of the enzyme.

Figure 19:
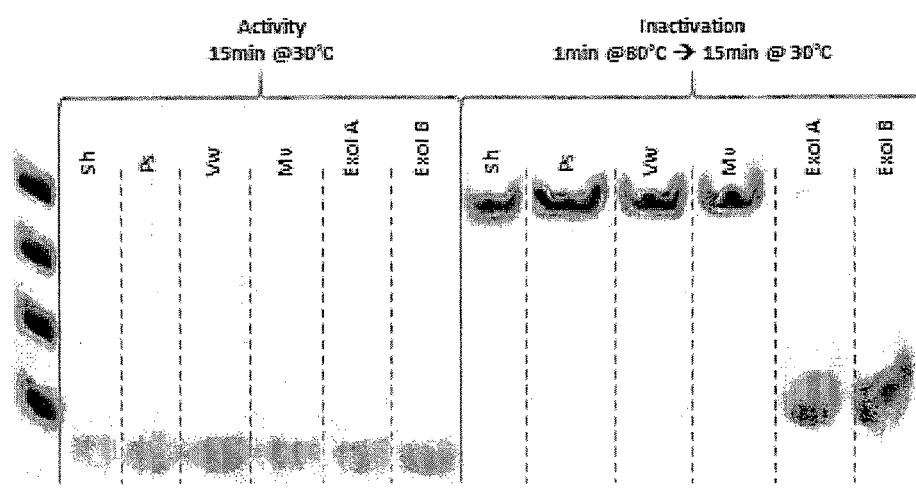

FIG. 19 shows a polyacrylamide gel on which the activity and inactivation of HL-ExoI (Ps, Sh, Vw, Mv) and E. coli ExoI were compared. Buffer conditions and reaction set up are as described in Example 12. All enzymes were tested for activity at 30° C. for 15 minutes as well as residual activity under the same time and temperature conditions following incubation at 80° C. for 1 minute. To mimic a post-PCR clean-up assay, reaction was performed in a post-PCR buffer.

Figure 20:
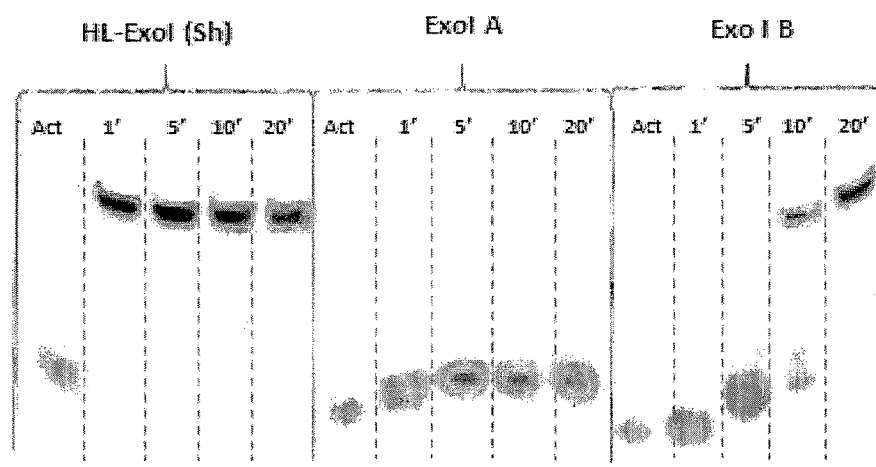
Figure 21A:
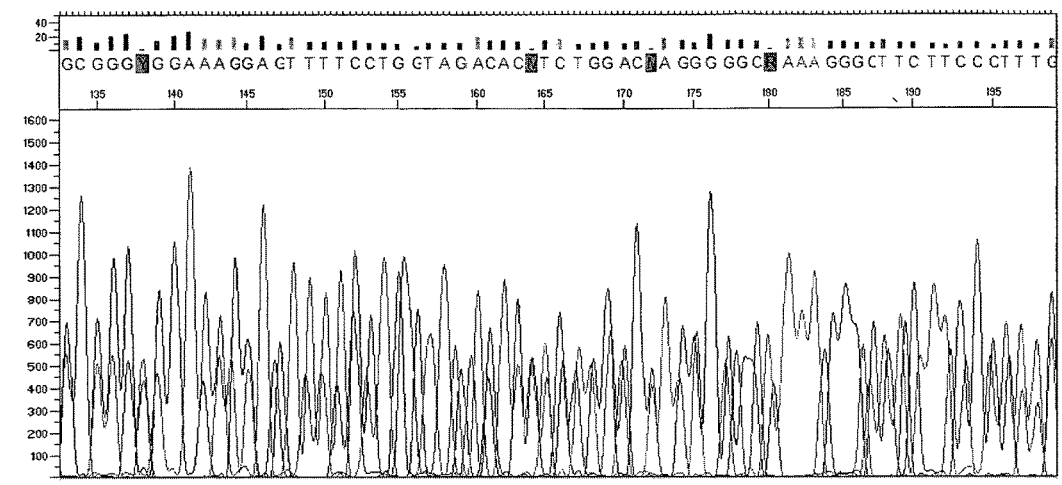
Figure 21B:
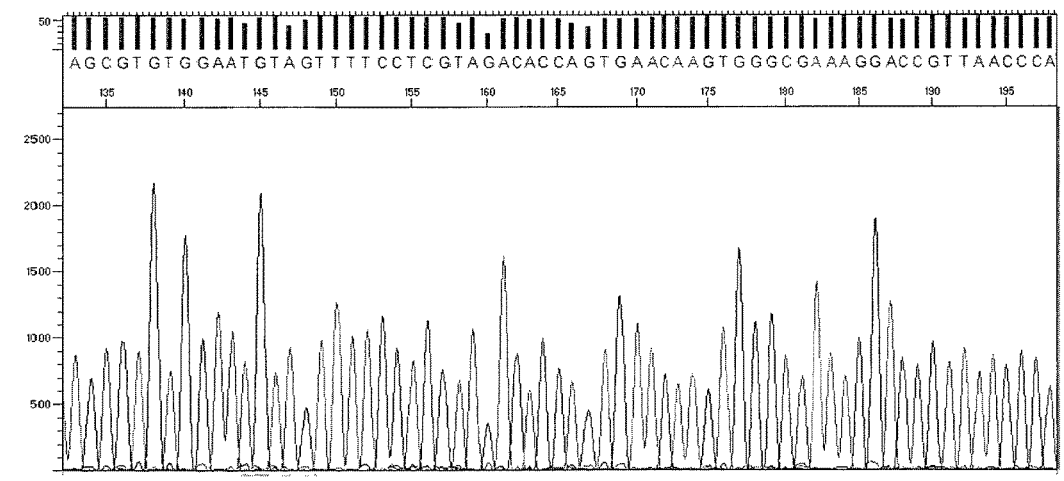
Figure 21C:
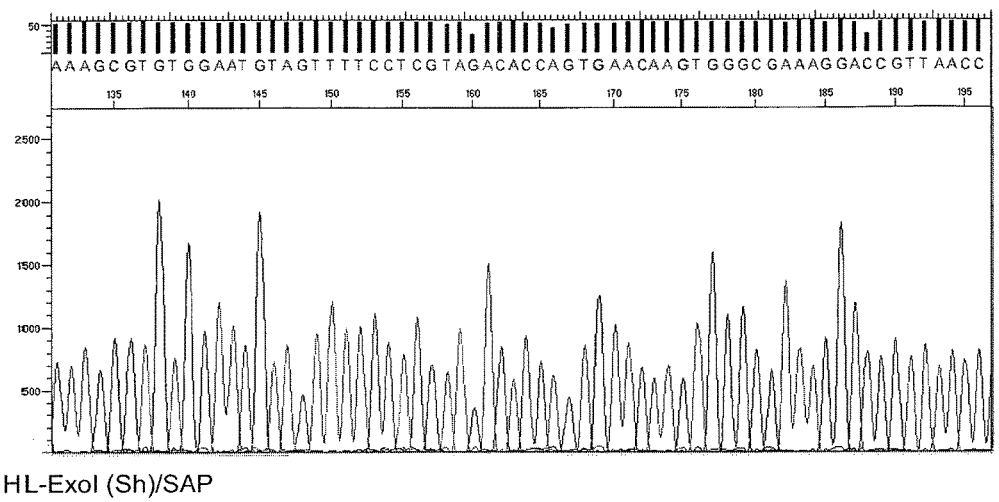
Figure 21D:
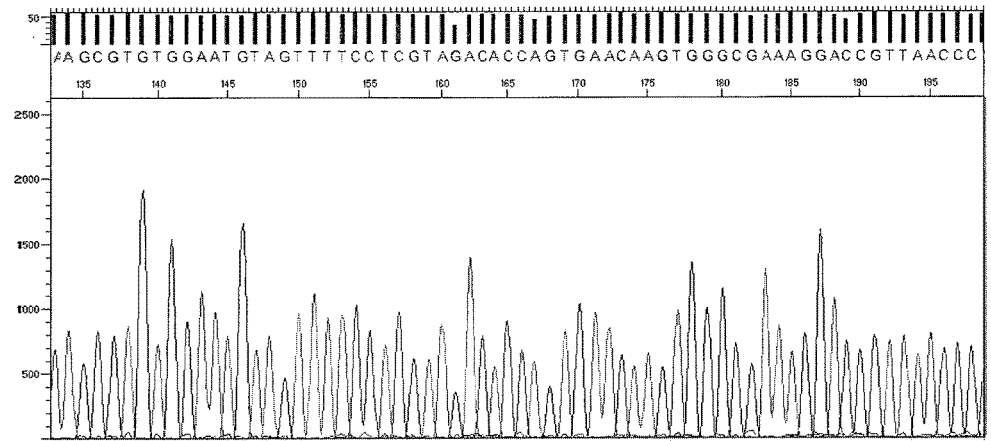
Figure 21E:
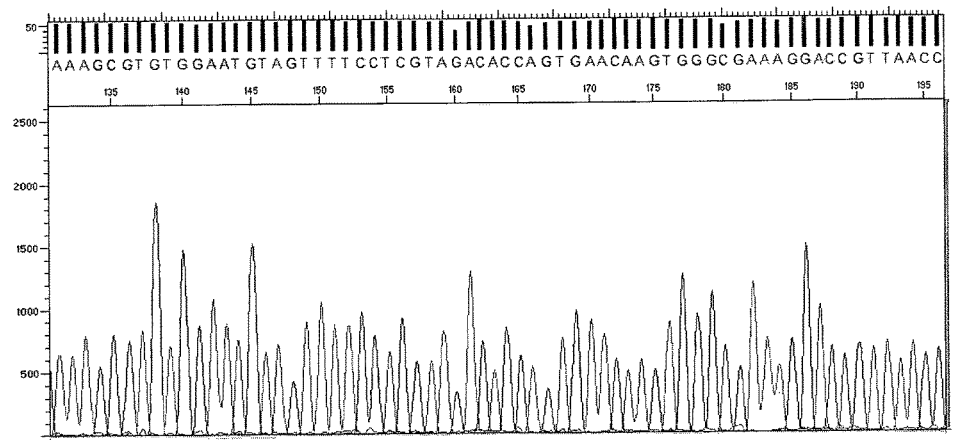
Figure 21F:
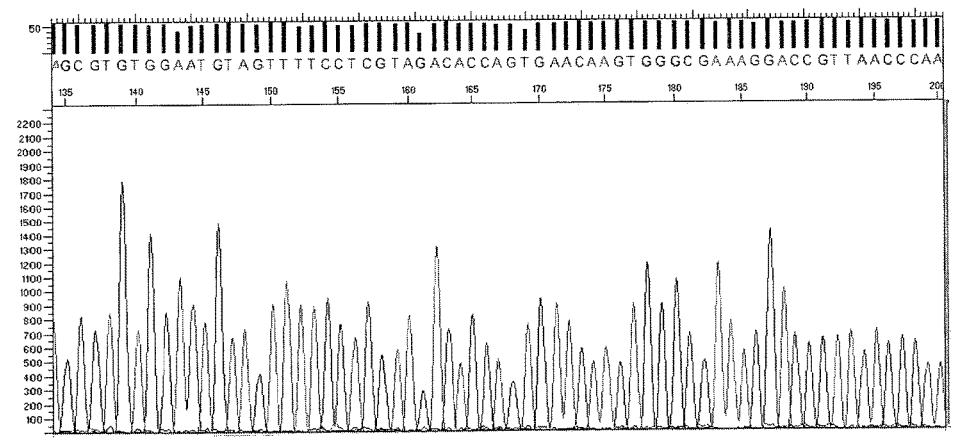

FIG. 20 shows a polyacrylamide gel on which the activity and inactivation of HL-ExoI (Sh) and E. coli ExoI were compared. Buffer conditions and reaction set up are as described in Example 12. All enzymes were incubated at 80° C. for 1, 5, 10 or 20 minutes before substrate addition and incubation at 30° C. for 15 minutes. To mimic a post-PCR clean-up assay, reaction was performed in a post-PCR buffer. No residual activity in HL-ExoI (Sh) was detected after 1 min incubation at 80° C., while substantial residual activity was observed with two commercial E. coli ExoI after 5 minutes, and even after 20 minutes incubation at 80° C. in the case of ExoI A.

FIG. 21 shows representative sequencing results from the sequencing reactions of Example 14 (A: Negative control; B: ExoSAP-IT; C: HL-ExoI (Sh)/SAP; D: HL-ExoI (Ps)/SAP; E: HL-ExoI (Mw)/SAP; F: HL-ExoI (Vw)/SAP. All images show the resulting chromatograms following addition of excess reverse primer prior to PCR clean-up. All sequencing results were based upon the GoTaq PCR buffer. ExoSAP-IT corresponds to the 30 minutes protocol, while HL-ExoI/SAP corresponds to the 5 minutes protocol, both described in Example 14.

EXAMPLES

Example 1

Cloning, Recombinant Expression and Partial Purification of Exonucleases

The sbcB exodeoxyribonuclease I (exoI) gene from *Moritella viscosa* (HL-ExoI (Mv)), *Vibrio wodanis* (HL-ExoI (Vw)), *Halomonas* (HL-ExoI (Ha)), *Psychromonas* (HL-ExoI (Ps)) and *Shewanella* (HL-ExoI (Sh)) gDNA was cloned by overlap extension PCR cloning (Bryksin and Matsumura, 2010, Biotechniques, 48 (6), 463-465) with a C-terminal His-tag by inserting the cloned gene into the pTrc99A expression vector for expression in *E. coli* TOP10. The primers used are listed in Table 1. Genetic source material was obtained from bacteria isolated from Norwegian offshore waters.

TABLE 1

Primers used for cloning of ExoI genes.

| Primer name | Sequence | SEQ ID No |
|---|---|---|
| Mv forward | GTGAGCGGATAACAATTTCACACAGGAAACAGACCATGGATAACAATTCGAACAAAACAGCAACAG | 23 |

TABLE 1-continued

Primers used for cloning of ExoI genes.

| Primer name | Sequence | SEQ ID No |
|---|---|---|
| Mv reverse | GCTGAAAATCTTCTCTCATCCGCCAAAACAGCCtcagtgatggtgatggtgatg-gcctgcagaTGCGCCAATTATTTTTTGACCATAAAGG | 24 |
| Vw forward | GTGAGCGGATAACAATTTCACACAGGAAACAGACCATGCCGCAGGATAACGCACCAAG | 25 |
| Vw reverse | GCTGAAAATCTTCTCTCATCCGCCAAAACAGCCtcagtgatggtgatggtgatggcctgcagaTGATACTAACTGTTGTACGTAATTATAAACGGCGC | 26 |
| Ha forward | GTGAGCGGATAACAATTTCACACAGGAAACAGACCATGGCATCACCCAATGCTGCC | 27 |
| Ha reverse | GCTGAAAATCTTCTCTCATCCGCCAAAACAGCCtcagtgatggtgatggtgatggcctgcagaGGCATCAAATGCCTGGGCCG | 28 |
| Ps forward | GTGAGCGGATAACAATTTCACACAGGAAACAGACCATGAATCAAGAATCCCCAAGCCTTCTTTGG | 29 |
| Ps reverse | GCTGAAAATCTTCTCTCATCCGCCAAAACAGCCtcagtgatggtgatggtgatggcctgcagaTGTATTCCCTGTCAAAAACTCTAAGTAATGTCC | 30 |
| Sh forward | GTGAGCGGATAACAATTTCACACAGGAAACAGACCATGAACAACACTAAGAAACAGCCAACTTTATTTTGG | 31 |
| Sh reverse | GCTGAAAATCTTCTCTCATCCGCCAAAACAGCCtcagtgatggtgatggtgatggcctgcagaAAGATTTCTAAGATAATGACACAAAGCCTGTAA | 32 |

Bold letters, pTrc99A specific sequence; upper case letters, gene specific sequence; lower case letters, spacer and tag sequence.

The pTrc99A-exo/vectors were transformed into *E. coli* TOP10 following the protocol for Z-competent cells (Zymo Research, U.S.A.). The cells were grown in baffled shake flasks in Terrific Broth (TB) medium; approximately 1.5% overnight precultures were transferred to 250 ml TB medium containing 100 μg/ml Ampicillin in 1000 ml growth flasks and incubated at 37° C., 200 rpm, until the $OD_{600}$ reached 0.4-0.6. The temperature was decreased to 15° C. and the cells were incubated for 30 minutes before they were induced for 4 hours with 0.5 mM IPTG. The cells were harvested by centrifugation and the cell pellets frozen at −20° C.

Cell pellets from the 250 ml cultures were thawed on ice, 40 ml lysis buffer (50 mM Tris-HCl (pH 7.5 at 25° C.), 5 mM imidazole, 1 M NaCl, 0.1% Triton X-100, 10% glycerol, 10 mM $MgCl_2$) was added and the mixture was sonicated in an ice water bath for 10 min (25% amplitude, 0.1 sec on, 0.2 sec off) using a Branson Sonifier. The lysate was centrifuged in a 50 ml tube at 25,000 g for 20 minutes and the supernatant filtered through a 0.45 μM filter. The filtered lysate was diluted with 50 ml of lysis buffer to a total volume of 90 ml. All purification steps were performed with ice cold buffers and a column cooled on ice. The 90 ml lysate was applied to a HisTrap HP 1 ml column equilibrated in lysis buffer using a flow of 1 ml/min. The column was washed with 5 column volumes (CV) of lysis buffer and 10 CV of buffer A2 (50 mM Tris-HCl, (pH 7.5 at 25° C.), 5 mM imidazole, 500 mM NaCl). The protein was then eluted with 20 CV of a 0-30% gradient of buffer B (50 mM Tris-HCl, (pH 7.5 at 25° C.), 500 mM Imidazole, 500 mM NaCl) to buffer A2 in 1 ml fractions. Fractions containing ExoI activity were pooled and either dialysed against 10 mM Tris-HCl (pH 7.5 at 25° C.), 500 mM NaCl and 0.5 mM EDTA, or 10 mM Tris-HCl (pH 7.5 at 25° C.), 500 mM NaCl, 10 mM $MgCl_2$ and 0.5 mM EDTA, and then diluted 1:1 with 100% glycerol and stored at −20° C.

Two more exonuclease I sequences (not disclosed) have been examined, but failed to express and isolate actively.

Example 2

Activity Profiling of Exonucleases: Optimum Temperature for Catalytic Activity

A temperature profile was created to better characterise the different recombinant HL-ExoI from Example 1. The different HL-ExoI were diluted to concentrations enabling differentiation between substrate degradations on the gel. Due to the different dilution factors, samples could not directly be compared to each other, but relative temperature-dependent differences in activity could be estimated. Samples were incubated for various time intervals to determine if the enzyme could sustain a set temperature for longer periods of time.
Detailed Method
HL-ExoI was diluted (10 mM Tris-HCl pH 7.5 at 25° C., 5 mM $MgCl_2$) to what was thought to give the best differentiation between samples. To mimic the PCR clean-up protocol, post-PCR solutions were used as reaction buffers. Robustness was achieved by running the experiment in parallel using post-PCR solutions based on two different PCR buffers; GoTaq (Promega) or TEMPase Key (VWR). As substrate, 5 pmol of a 5' FAM labeled oligonucleotide (GCTAACTACCACCTGATTAC; SEQ ID No 21) was added to each reaction. Following addition of the ExoI, the total volume for each sample was 7 μl. Samples were incubated in a thermocycler for 1 minute, 5 minutes or 10 minutes at 20° C., 25° C., 30° C. or 37° C. followed by 5 minutes at 80° C. A TBE-Urea Sample Buffer (Bio-Rad) was added and samples were applied to a casted 20% Acrylamide/7M Urea gel and run at 180 V for approximately 45 minutes. All reagents were kept on ice during the full protocol unless specified otherwise and workflow was performed on cooling blocks.
Results
Results are shown in FIG. 12. In general, all HL-ExoI performed similarly in the two buffers used to prepare the post-PCR samples, showing that the observed effects were not specific to the PCR-buffer composition.

Figure 12A:
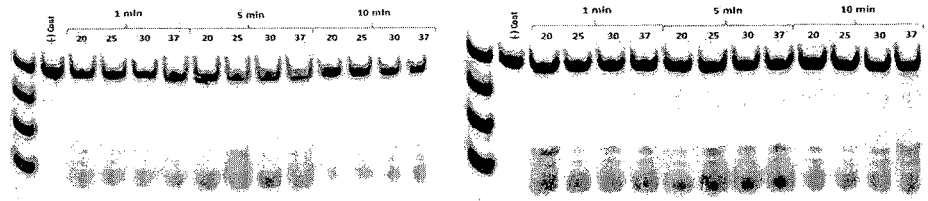

HL-ExoI (Ha) showed an overall increasing activity up to 37° C. and could withstand this temperature for at least 10 minutes (FIG. 12a). Good overall activity at lower temperatures was also seen.

Figure 12B:
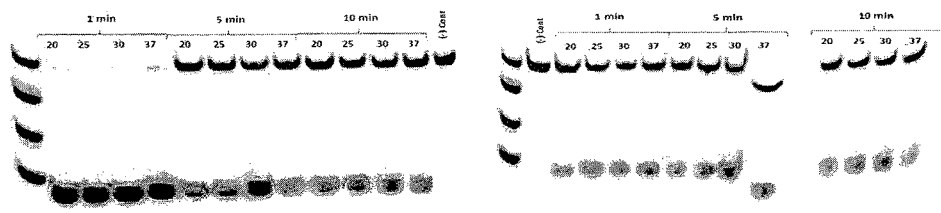

HL-ExoI (Ps) showed an overall best activity at 30° C., with loss of activity when using 37° C. as incubation temperature (FIG. 12b). Good overall activity at lower temperatures was also seen.

Figure 12C:
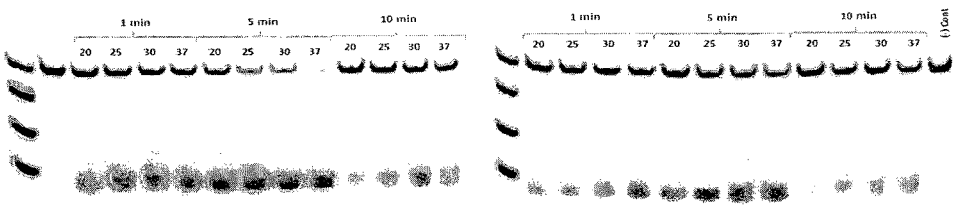

HL-ExoI (Sh) showed an overall best activity at 37° C., and could withstand this temperature for at least 10 minutes (FIG. 12c). Good overall activity at all temperatures was also seen.

Figure 12D:
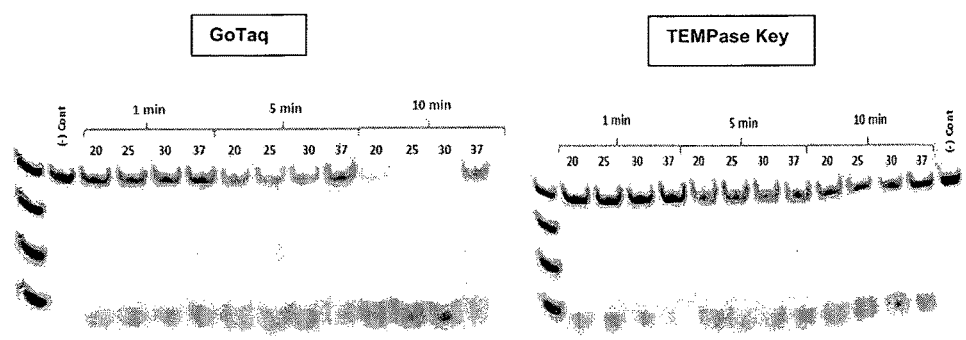

HL-ExoI (Mv) showed an overall best activity at 30° C., while incubation at 37° C. resulted in loss of activity (FIG. 12d). Good activity at lower temperatures was also seen.

Using PAGE for activity profiling appeared to give good estimates as to how the HL ExoI behaved depending on temperature over time.

Example 3

Activity Profiling of Exonucleases: Inactivation Temperatures for Catalytic Activity In this Example, the thermal inactivation characteristics of HL-ExoI (Sh) were compared to various commercially available E. coli ExoI.

The thermal inactivation characteristics of four different commercially available E. coli ExoI and one commercially available enzymatic PCR clean-up kit were compared to HL-ExoI (Sh). To ensure that any observed effects were irrespective of the choice of reaction buffer, two different post-PCR solutions were used as a reaction buffer (TEMPase Key, TEMPase Extra, VWR). All reactions received about 10 U of ExoI to enable comparison between the ExoI activities and ease of thermal inactivation. The exonuclease activity of HL-ExoI (Sh) was calculated as described in Example 8. For the commercial ExoIs, exonuclease activity was taken as that stated by the manufacturers. Final volume for each reaction was 7 μl. Samples were incubated at 80° C. for 1 minute before cooling and addition of 5 pmol of a 5' FAM labeled oligonucleotide (GCTAACTACCACCTGATTAC; SEQ ID No 21). Samples were further incubated at 37° C. for 15 minutes. Following incubation, a TBE-Urea Sample Buffer (Bio-Rad) was added and samples were applied to a casted 20% acrylamide/7 M urea gel and run at 180 V for approx. 45 minutes. All reagents were kept on ice during the full protocol and workflow was performed on cooling blocks unless specified otherwise.

Results are shown in FIG. 13. All of the E. coli ExoI had adequate activity following 1 minute incubation at 80° C. to completely degrade all of the substrate. HL-ExoI (Sh) was the only ExoI that was completely inactivated, showing no signs of residual activity.

Example 4

Demonstration of Utility of HL-ExoI (Sh) in a Rapid PCR Clean-up Prior to Nucleic Acid Sequencing Experiments were set up to verify that HL-ExoI (Sh) could perform satisfactorily in a rapid PCR clean-up scenario. For comparison and positive control, parallel samples were treated with a leading brand of enzymatic PCR clean-up reagent ExoSAP-IT (Affymetrix).

To verify that HL-ExoI (Sh) enabled a 5 minute enzymatic PCR clean-up protocol, an experiment was designed to stress-test the protocol limitations. Thus, to all post-PCR solutions under test there were added excess primers or dNTPs following the PCR. If left unremoved prior to the sequencing reaction, residual primers would result in sequence reactions in the opposite direction and thereby strongly compromise the length and quality of the reaction, and dNTPs would result in ddNTP:dNTP ratios which would fail to yield high quality sequences. Robustness was achieved by using different PCR reagents and amplicons.

Following PCR, 10 pmol primers or 40 nmol dNTPs were added to the post-PCR solutions.

Samples to be treated with ExoSAP-IT were handled according to manufacturer protocol. Following addition of either reverse primer or dNTP to the PCR solution, samples received 2 μl of the clean-up reagent, giving a final volume of 7 μl. Samples were incubated 15 minutes at 37° C. followed by 15 minutes at 80° C. Samples were set up using two different PCR buffers and all samples were set up as triplicates.

Samples to be treated with HL-ExoI (Sh) received the same amount of added primers and dNTPs as above, before addition of 1 μl of HL-ExoI (Sh) (10 U/μl, as calculated in Example 8) and 1 μl of SAP (2 U/μl). As with the positive controls, the final volume of the samples were 7 μl. Samples were incubated 4 minutes at 37° C. followed by 1 minute at 80° C. Samples were set up using two different PCR buffers and all samples were set up as triplicates.

To evaluate how ExoSAP-IT would perform given a protocol identical to HL-ExoI, samples were spiked with reverse primers before the addition of 2 μl of the ExoSAP-IT PCR clean-up reagent. Samples were set up as duplicates.

As negative controls, samples received reverse primers or dNTPs, but instead of enzymatic clean-up solutions, samples received 2 μl water. Samples were set up as duplicates.

Table 2 provides an overview of the above described experimental set up.

| Reagent | Volume |
|---|---|
| Post-PCR solution (TEMPase Extra, VWR or GoTaq, Promega) Spike | 4 μl |
| dNTP (10 mM ACGT each) or Reverse primer (10 μM) PCR clean-up | 1 μl |
| ExoSAP-IT (commercially available PCR clean-up solution) or HL-ExoI & SAP or dH$_2$O | 2 μl |
| Total | 7 μl |

Table 3 provides an overview of the PCR clean-up incubation

| Protocol | Incubation | Total time |
|---|---|---|
| ExoSAP-IT | 15 minutes at 37° C. → 15 minutes at 80° C. | 15 minutes |
|  | 4 minutes at 37° C. → 1 minute at 80° C. | 5 minutes |
| HL-ExoI + SAP | 4 minutes at 37° C. → 1 minute at 80° C. | 5 minutes |
| Negative control | 15 minutes at 37° C. → 15 minutes at 80° C. | 15 minutes |

Following PCR clean-up treatment, samples were immediately cooled on ice. A prepared sequencing reaction mastermix was aliquoted into separate tubes. A total of 2.5 μl of each treated/untreated solution was added to each tube to be used as a template in the subsequent sequencing reaction. Samples were immediately transferred to a thermocycler and the sequencing program was initiated.

| Reagent | Volume |
|---|---|
| BigDye v3.1 (LifeTech) | 1 μl |
| 5X Sequencing Buffer (LifeTech) | 4 μl |
| Sequencing primer (10 μM) | 0.32 μl |
| Template (treated/untreated PCR product with spike) | 2.5 μl |
| dH$_2$O | 12.18 μl |
| Total | 20 μl |

| Cycling temperature | Time | |
|---|---|---|
| 96° C. | 5 min | |
| 96° C. | 10 sec | ⎫ |
| 50° C. | 5 sec | ⎬ 25 cycles |
| 60° C. | 4 min | ⎭ |
| 4° C. | Hold | |

Sequences were delivered to the DNA Sequencing core Facility at University of Tromsøfor purification and sequencing using an Applied Biosystems 3130xl Genetic Analyzer. Results were analyzed using the Sequence Scanner Software v1.0 (LifeTech).

Selected results are shown in FIG. 14. Sequences spiked with dNTP yielded an overall good sequence length and quality, and no difference between samples treated with ExoSAP-IT or HL-ExoI/SAP could be detected (results not shown). The sequence plots of FIG. 14*a* are examples of the results from sequences spiked with reverse primers in the GoTaq PCR buffer. It was evident from the negative controls that lack of functional PCR clean-up strongly compromised the length and quality of the sequence. Samples treated with either ExoSAP-IT (30 minutes protocol) or HL-ExoI/SAP (5 minutes protocol) showed very good sequence quality. These images were representative for all replicates.

The sequence plots of FIG. 14*b* are examples of the results from sequences spiked with reverse primers in the TEMPase Extra PCR buffer. Samples with added reverse primers showed very good sequence length and quality upon treatment with either of the PCR clean-up solutions. There were no significant differences between the ExoSAP-IT-treated samples (30 minutes protocol) or the HL-ExoI/SAP-treated samples (5 minutes protocol). Lack of PCR clean-up treatment resulted in shorter sequences of lower quality. These images were representative for all replicates.

On the other hand FIG. 14*c* illustrates how the ExoSAP-IT clean-up solution performed when having to perform the same 5 minutes protocol as HL-ExoI/SAP-protocol. Evident from the Figure is that treatment with ExoSAP-IT did not result in sequences of high quality. This is likely due to a combination of insufficient degradation of added primers as well as residual ExoI activity degrading sequencing primers. It is likely that using a reaction set-up at room temperature would further compromise these results due to the residual ExoI activity degrading sequencing primers. Samples treated with HL-ExoI/SAP showed overall excellent sequence length and quality.

Example 5

Inactivation Experiments to Determine Minimum Inactivation Time and Temperature for Certain Heat-labile Exonucleases of the Invention Minimum inactivation temperature and time was determined for each HL-ExoI under test under the given assay conditions. This was achieved by incubating HL-ExoI at different temperatures for different time intervals. Following heat-treatment, 5' labeled single stranded DNA was added and degree of substrate degradation was visualized (FIG. 15). The amount of substrate degradation was compared to the results from FIG. 16, and residual activity following heat treatment was estimated.

Undiluted HL-ExoI was added to Reaction Buffer (10 mM Tris-HCl, pH 8.5 at 25° C., 50 mM KCl, 5 mM MgCl$_2$), giving a final volume of 9 µl. Samples were incubated for 5 minutes, 10 minutes or 15 minutes at 40° C., 45° C., 50° C. or 55° C. or for 5 minutes or 10 minutes at 60° C. Following cooling of samples, 5 pmol of a 5'FAM labeled oligonucleotide (GCTAACTACCACCTGATTAC; SEQ ID No 21) was added. Samples were further incubated at 30° C. for 30 minutes and then for 2 minutes at 95° C. A TBE-Urea Sample Buffer (Bio-Rad) was added and samples were applied to a precast 20% acrylamide/7 M urea gel and run at 180 V for approximately 45 minutes. All reagents were kept on ice during the full protocol and workflow was performed on cooling blocks unless specified otherwise. PAGE results were imaged using the Molecular Imager PharosFX system (Bio-Rad).

Results are shown in FIG. 15 and indicate that various degrees of substrate degradation are observed depending on temperature and time-interval for heat-incubation. Overall, none of the HL-ExoI showed any signs of substrate degradation following incubation at 55° C. for 10 minutes or more. Incubations of all of the HL-ExoI at 55° C. for 5 minutes or 50° C. for 10 minutes showed essentially no, or at most between 1 and 10%, substrate degradation.

Example 6

Determination of Sensitivity Threshold for Inactivation Experiments by Measuring Degree of Substrate Degradation for a Dilution Series of Exonucleases In order to determine the minimum inactivation temperature for the various HL-ExoI of the previous Example, the sensitivity threshold for the inactivation assay of Example 5 was determined. A semi-quantitative assay was prepared using serial dilutions of the exonucleases and estimating the degree of substrate degradation for each dilution. For comparative measurements, the same assay conditions and reaction set-up as used in the inactivation assays were also applied here.

Each HL-ExoI under test was diluted 1, 10, 100, 200, 1000 and 10,000 times, corresponding to 100%, 10%, 1%, 0.5%, 0.1% and 0.01% activities. The same buffer as used as Reaction Buffer was also used as Dilution Buffer (10 mM Tris-HCl, pH 8.5 at 25° C., 50 mM KCl, 5 mM MgCl$_2$). Reaction Buffer and 5 pmol of FAM-labeled substrate (GCTAACTACCACCTGATTAC; SEQ ID No 21) were premixed prior to HL-ExoI addition. Total volume of reaction was 10 µl. Samples were incubated for 30 minutes at 30° C., followed by 2 minutes at 95° C. A TBE-Urea Sample Buffer (Bio-Rad) was added and samples were applied to a precast 20% acrylamide/7M urea gel and run at 180 V for approx. 45 minutes. All reagents were kept on ice during the full protocol and workflow was performed on cooling blocks unless specified otherwise. PAGE results were imaged using the Molecular Imager PharosFX system (Bio-Rad).

Results are shown in FIG. 16 and indicate that activity of the exonucleases could be detected to approximately 1% activity in the given assay conditions.

Example 7

Assay for Determining Double-stranded and Single-stranded Exonuclease Activity

Exonuclease activity is measured by incubating the test exonuclease enzyme with a short 5'-FAM-DNA-TAMRA-3' labelled single or double stranded substrate of approximately 20 nucleotides. If the exonuclease is able to degrade the substrate this will start immediately and the fluorophore will be released. The activity can be followed over time since the released fluorophore can re-emit light upon light excitation.

Specifically, the assay mix consists of 1 µl 10 µM ssDNA/dsDNA, 10 µl 5× TDB (250 mM Tris-HCl, pH 8.5 at 25° C., 5 mM DTT, 1 mg/ml BSA, 10% Glycerol) and 29 µl MiliQ H$_2$O. 40 µl assay mix is transferred to the wells of a black flat bottom 96-well plate and 5 µl MiliQ H$_2$O or dilution buffer (as negative control) and enzyme samples are added to the wells. The reactions are initiated by adding 5 µl 50 mM MgCl$_2$ using a multichannel pipette, making the final volume of the reaction 50 µl. Fluorescence is measured immediately (excitation 485 nm and emission at 520 nm) and then at appropriate time intervals, include a shaking step, and the reactions are allowed to proceed for 15 minutes. An increase in fluorescence indicates degradation of the substrate is taking place.

Example 8

Assay for Quantifying Single-stranded Exonuclease Activity

Single strand DNA exonuclease activity was measured by incubating the enzyme with a denatured $^3$H-dATP incorporated PCR product. If the exonuclease is able to degrade the substrate the exonuclease will release acid soluble nucleotides that can be detected in a scintillation counter. Excess high molecular weight substrate DNA is precipitated with trichloroacetic acid (TCA). In this assay, one Unit (1 U) is defined as the amount of enzyme that will catalyse the release of 10 nmol acid-soluble nucleotides in a final volume of 20 µl in 30 minutes at 30° C.

Specifically, the assay mix consisted of 4 µl 5× Exonuclease buffer (250 mM Tris-HCl, pH 7.5 at 25° C., 50 mM MgCl$_2$, 5 mM DTT), 5 µl denatured substrate (denatured by incubation for 3 minutes at 100° C. and immediate transfer to an ice water bath for 3 minutes) and 6 µl MiliQ H$_2$O. 15 µl was transferred to 1.5 ml microcentrifuge tubes on ice. The enzyme under test was diluted when necessary and 5 µl each of enzyme sample, control and blank was added to the assay mix and mixed by pipetting up and down. The samples were incubated in a water bath at 30° C. for 10 minutes. After incubation the reactions were placed on ice and 20 µl ice cold calf thymus DNA (1 mg/ml) and 250 µl ice cold 10% (w/v) TCA were added immediately. The samples were then incubated on ice for 15 minutes and centrifuged at 4° C. for 10 minutes at 13,000 rpm. The supernatants, 200 µl, were transferred to a 24-well plate and 0.8 ml Ultima Gold XR Scintillation fluid was then added. The wells were sealed with sealing tape and the samples were mixed thoroughly by shaking. The samples were counted in a MicroBeta$^2$ Plate Counter for 5 minutes.

Example 9

Assay for Quantifying Double-stranded Exonuclease Activity

Double strand DNA exonuclease activity is measured in the same way as Example 8 with the exception that the PCR substrate is not denatured prior to incubation with the enzyme.

Example 10

Comparison of the Double Stranded and Single Stranded Exonuclease Activities of the Heat Labile Exonucleases of the Invention Single strand DNA exonuclease activity was measured by incubating the test enzyme with a denatured $^3$H-dATP incorporated PCR product. Double strand DNA exonuclease activity was similarly measured with the exception that the enzyme was incubated with a non-denatured $^3$H-dATP incorporated PCR product. If an exonuclease is able to degrade the substrate the exonuclease will release acid soluble nucleotides that can be detected in a scintillation counter. Excess high molecular weight substrate DNA is precipitated with trichloroacetic acid (TCA). In this assay, one Unit (1U) is defined as the amount of enzyme that will catalyse the release of 10 nmol acid-soluble nucleotides in a final volume of 20 µl in 30 minutes at 30° C. Specifically, the assay mix consisted of 4 µl 5× buffer (50 mM Tris-HCl, pH 8.5 at 25° C., 250 mM KCl and 25 mM MgCl$_2$), 5 µl substrate (to obtain ssDNA the dsDNA substrate was denatured by incubation for 3 minutes at 100° C. and immediate transferred to an ice water bath for 3 minutes) and 3 µl MiliQ H$_2$O. The assay mix, 12 µl, was transferred to 1.5 ml microcentrifuge tubes on ice. The enzyme under test was diluted and 8 µl of enzyme sample was added to the assay mix and mixed by pipetting up and down. Control and blank were also included in the set-up. The samples were incubated in a water bath at 30° C. for 10 minutes. After incubation the reactions were placed on ice and 20 µl ice cold calf thymus DNA (1 mg/ml) and 250 µl ice cold 10% (w/v) TCA were added immediately. The samples were then incubated on ice for 15 minutes and centrifuged at 4° C. for 10 minutes at 13,000 rpm. The supernatants, 200 µl, were transferred to a 24-well plate and added 0.8 ml Ultima Gold XR Scintillation fluid. The wells were sealed with sealing tape and the samples mixed thoroughly by shaking. The samples were counted in a Micro-Beta$^2$ Plate Counter for 5 minutes.

The results are summarized in Table 4 and shows that the HL-ExoI of the invention display very little activity against double stranded DNA compared to the activity against single stranded DNA. It is however difficult to conclude if the low amounts of activity against double stranded DNA are related to intrinsic properties of the enzymes or is caused merely by contaminations of the enzymes. The two commercial ExoI (ExoI A and ExoI B) tested also displayed very low activity against double stranded DNA.

TABLE 4

Activity of HL-ExoI and commercial Exoi against ssDNA and dsDNA.

|  | Activity against ssDNA (U/µl) | Activity against dsDNA (U/µl) | Relative activity against dsDNA and ssDNA (%) |
| --- | --- | --- | --- |
| HL-ExoI Ha | 50.9 | 0.05 | 0.10 |
| HL-ExoI Ps | 11.2 | 0.02 | 0.18 |
| HL-ExoI Sh | 65.1 | 0.01 | 0.02 |
| HL-ExoI Vw | 21.0 | 0.01 | 0.05 |
| HL-ExoI Mv | 16.7 | 0.01 | 0.06 |
| ExoI A | 16.7 | 0.01 | 0.06 |
| ExoI B | 41.2 | 0.01 | 0.02 |

Example 11

Activity Profiling of Exonucleases: Directionality Determination Using Urea Polyacrylamide Gel This experiment was performed in order to verify that the HL-ExoI of the invention exhibited 3' to 5' exonuclease activity and no substantial 5' to 3' exonuclease activity. The substrate specificity was analysed using either a 5' FAM or a 3' FAM-labeled oligonucleotide (GCTAACTACCACCT-GATTAC; SEQ ID No 21) on a polyacrylamide gel.

Each HL-ExoI under test was diluted to a final concentration of about 0.1 U/µl. Two master mixes were prepared, one for the 5' FAM-labeled oligo and one for the 3' FAM-labeled oligo. The master mix contained Reaction Buffer (10 mM Tris pH 8.5, 50 mM KCl, 5 mM MgCl$_2$) and the respective FAM-labeled substrate, giving a final amount of 0.25 pmol substrate per reaction. Both a negative control, containing dilution buffer instead of enzyme solution, and a positive control, using Exo I from *E. coli*, were included. The enzymes were pipetted into the pre-cooled reaction tubes and then the master mix with the reaction buffer and substrate was added. All reactions consisted of a final volume of 10 µl and were incubated at 30° C. for 1 h. Reactions were stopped by adding 2.5 µl of sample loading buffer (95% formamide, 10 mM EDTA, Xylene) and incubated at 95° C. for 5 min. For analysis, 6 µl of the samples were loaded onto a 12% acrylamide/7 M urea gel. The gel was run at 50 W for 1 h 45 minutes. During the set-up of the reactions all reagents and samples were kept on ice.

Results are shown in FIG. 17. Clear differences between the 5' FAM-labeled and 3' FAM-labeled substrate are observed, indicating 3' to 5' directionality of the different HL-ExoI as well as for the *E. coli* ExoI control. When FAM was labeled at the 5' end, a ladder of partial faint and intense intermediate product bands were seen indicating the ExoI degrading the substrate from the 3' end. When the oligo was FAM-labeled at the 3' end, the fluorophore was immediately cut off, generating only the 3'FAM monomer.

Example 12

Activity Profiling of Exonucleases: Directionality on Crystallisation Structure To further support the directionality of the HL-ExoI I enzymes of the invention having 3'-5' directionality, the HL-ExoI (Mv) was crystalised with ssDNA and the structure of the complex was determined.

Protein crystallisation was performed with a protein concentration of 5.4 mg/ml. The desalted 13mer oligonucleotide (dT13) was purchased from Sigma Aldrich and added to the protein in a 1.2 molar excess. To inhibit the degradation of the ssDNA by the exonucleaseI, 10 mM EDTA was added.

The drops were set up automatically in a 96-well format in MRC 2 Well Crystallization Plates (Swissci, Hampton Research) with the Phenix (Art Robbin Instruments) using the sitting drop vapor diffusion technique. The drop size was 0.4 µl (0.2 µl+0.2 µl) and the volume of the reservoir solution was 60 µl. The crystallisation plates were incubated at 4° C.

A crystal co-crystallised with dT13/EDTA grew with 20.02% PEG MME 5000, 0.1 M Na-acetate pH 4.5 and 0.09 M Ca-acetate. The X-ray diffraction experiment was performed at the ESRF in Grenoble (France). The crystal diffracted to 2.5 Å resolution. Structure determination has been performed by molecular replacement with the E. coli ExoI (PDB: 1FXX) as the search model.

In the early rounds of refinement, electron density for the ssDNA became visible and all nucleotides could be fit in. The ssDNA binds with the 3"-end in the active site in a similar manner as seen for E. coli Exo I (Korada et al., Nucleic Acids Research, 2013, 41(11):5887-97) providing structural evidence for the HL-ExoI (Mv) 3"-5"directionality.

Example 13

Activity Profiling of Exonucleases: Rapid Inactivation of Certain HL-ExoI of the Invention at 80° C.

This experiment was performed to confirm that certain of the HL-ExoI of the invention could perform satisfactorily in a rapid PCR clean-up scenario. In this experiment, the thermal inactivation characteristics of the HL-ExoI under test at 80° C. were compared to two commercially available E. coli ExoI (ExoI A and ExoI B).

The activities of the HL-ExoI of the invention against ssDNA was calculated as described in Example 8, with the exception that the 1× assay mix consisted of 67 mM Glycin-KOH, pH 9.5, 63.5 mM NaCl, 9.2 mM MgCl$_2$, 10 mM DTT including $^3$H dA-labelled DNA. For the commercial E. coli ExoI, the activity was taken as that stated by the manufacturers. To mimic the set-up in a PCR clean-up setting, a post PCR buffer was used as the reaction buffer. The composition of the reaction buffer was 10 mM Tris-HCl pH 8.5 (25° C.), 50 mM KCl, 1.5 mM MgCl$_2$, DyNAzyme II (Thermo Fisher Scientific™, formerly Finnzymes™) and remnants of dNTPs (initially 200 µM of each before the PCR-reaction was run), remnants of primers (initially 200 nM of each primer before the PCR-reaction was run) and template.

Each reaction received 10 U ExoI, giving a final reaction volume of 7 µl. The experiment contained both an activity control for all ExoI, as well as a check for residual activity following heat incubation. For the activity control, reaction buffer, ExoI and 5 pmol substrate (GCTAACTACCACCT-GATTAC; SEQ ID No 21) were mixed and incubated for 15 minutes at 30° C. followed by 95° C. for 20 minutes. For samples to be analysed with respect to inactivation at 80° C., substrate was added following 1 minute incubation at 80° C. and subsequent cooling. These samples were subsequently incubated for 15 minutes at 30° C. followed by 95° C. for 20 minutes. Following all incubation steps, TBE-Urea Sample buffer was added and samples were applied to a precast 20% acrylamide/7 M urea gel and run at 180 V for approximately 45 minutes.

Results are shown in FIG. 19. All Exo I had adequate activity in this assay. Only the HL-ExoI were inactivated following 1 minute incubation at 80° C., while the two commercially available E. coli Exo I showed adequate residual activity degrading 100% of the substrate. The HL-ExoI, but not the commercial ExoI, compatible with a rapid 5 minute PCR clean-up protocol.

To further compare the ease of inactivation of HL-ExoI (Sh) with that of two commercially available E. coli ExoI, 10 U of each ExoI was incubated for 1, 5, 10 or 20 minutes at 80° C. before cooling and addition of 5 pmol of a 5' FAM labeled substrate (GCTAACTACCACCTGATTAC; SEQ ID No 21). The samples were further incubated for 15 minutes at 30° C. followed by 20 minutes at 95° C. Reaction set-up was otherwise identical to the above experiment, using the same post-PCR buffer as reaction buffer. An activity control was included for the three ExoI, and these samples were not subjected to heat incubation prior to incubation at 30° C. for 15 minutes. Residual activity was visualized on a Urea-PAGE gel as described above.

Results are shown in FIG. 20. Substantial residual activity was observed in both commercially available ExoI following heat treatment at 80° C. for nearly all time durations. In comparison, no residual activity could be detected in the samples treated with HL-ExoI (Sh) which had been treated at 80° C. for even a single minute.

Example 14

Demonstration of the Utility of HL-ExoI in a Rapid One-tube PCR Clean-up Prior to Nucleic Acid Sequencing This example was performed to show functionality of certain HL-ExoI of the invention in a PCR clean-up situation. The experimental set-up was very similar to Experiment 4. As in Example 4, to the post PCR solution under test was added excess primers (10 pmol) following the PCR. However, unlike Example 4 only one PCR buffer (GoTaq, Promega) was used, the incubation temperature for samples treated with HL-ExoI was reduced from 37° C. to 30° C. and only the regular 30 minutes protocol was tested for ExoSAP-IT.

Prior to initiating the experiment, the activity of each HL-ExoI was calculated as described in Example 8, with the exception that the 1× assay mix consisted of 67 mM Glycin-KOH, pH 9.5, 63.5 mM NaCl, 9.2 mM MgCl$_2$, 10 mM DTT including $^3$H dA-labelled DNA. Samples treated with HL-ExoI received the amount of primers as stated above, before the addition of 2 µl premixed HL-ExoI (10-20 U/µl) and SAP (1.5 U/µl). Total volume for each clean-up reaction was 7 µl. Samples were incubated 4 minutes at 30° C. followed by 1 minute at 80° C. Samples were set up as triplicates For comparison and positive control, samples were treated with a leading brand of enzymatic PCR clean-up; ExoSAP-IT™ (Affymetrix™). Samples treated with ExoSAP-IT were handled according to manufacturer protocol. Following addition of primers to the PCR solution, samples received 2 µl of the PCR clean-up reagent, giving a final volume of 7 µl. ExoSAP-IT-treated samples were incubated 15 minutes at 37° C. followed by 15 minutes at 80° C. Samples were set up as triplicates.

Negative controls were set up and these received the same amount of primers as treated samples. Instead of enzymatic clean-up solution, these samples received 2 µl water. Samples were set up as triplicates.

Example 4 should be referred to for more details.

Sequences were delivered to the DNA Sequencing core Facility at University of Tromso for purification and sequencing using Applied Biosystems 3500xl Genetic Analyzer. Results were analyzed using the Sequence Scanner Software v2.0 (LifeTech)

Selected results are shown in FIG. 21, where the sequence plots are representative examples of the results from sequences spiked with reverse primers in the GoTaq PCR buffer. It was evident from the negative controls that lack of functional PCR clean-up strongly compromised the length and quality of the sequence. Samples treated with either ExoSAP-IT (30 minutes protocol) or HL-ExoI/SAP (5 minutes protocol) showed very good sequence quality.

---

The invention claimed is:

1. A method of removing single stranded DNA from a sample, said method comprising contacting the sample with an exonuclease or enzymatically active fragment thereof under conditions which permit the digestion of at least a portion of any single stranded DNA present in the sample and then heating the exonuclease treated sample to inactivate said exonuclease or enzymatically active fragment thereof, wherein said exonuclease has the amino acid sequence of SEQ ID NO:1 or an amino acid sequence which is at least about 85% identical thereto, wherein said enzymatically active fragment of said exonuclease is at least about 85% identical to the amino acid sequence of said exonuclease, wherein said exonuclease or enzymatically active fragment thereof (i) is at least 90% irreversibly inactivated by heating at a temperature of about 55° C. for 10 mins in a buffer consisting of 10 mM Tris-HCl, pH 8.5 at 25° C., 50 mM KCl and 5 mM MgCl$_2$;
   (ii) has activity against double stranded DNA that is equal to or less than 15% of its activity against an equivalent amount of single stranded DNA under the same assay conditions; and
   (iii) has a 3'-5' exonuclease activity.

2. A method of removing single stranded DNA from a sample, said method comprising contacting the sample with an exonuclease or enzymatically active fragment thereof under conditions which permit the digestion of at least a portion of any single stranded DNA present in the sample and then heating the exonuclease treated sample to inactivate said exonuclease or enzymatically active fragment thereof, wherein said exonuclease has an amino acid sequence selected from:
   SEQ ID NO:1 or an amino acid sequence which is at least 85% identical thereto,
   wherein said enzymatically active fragment of said exonuclease is at least about 85% identical to the amino acid sequence of said exonuclease,
   wherein said exonuclease or enzymatically active fragment thereof
   (i) is substantially at least 90% irreversibly inactivated by heating at a temperature of about 55° C. for 10 mins in a buffer consisting of 10 mM Tris-HCl, pH 8.5 at 25° C., 50 mM KCl and 5 mM MgCl$_2$;
   (ii) is substantially specific for has activity against double stranded DNA that is equal to or less than 15% of its activity against an equivalent amount of single stranded DNA under the same assay conditions; and
   (iii) has a 3'-5' exonuclease activity.

3. The method as claimed in claim 1, wherein said exonuclease has an amino acid sequence selected from any one of SEQ ID NO:1 and SEQ ID:11.

4. The method of claim 1, wherein said sample is the product of a nucleic acid amplification reaction or the product of a reverse transcription reaction or a sample for sequence analysis.

5. The method of claim 4, wherein said nucleic acid amplification reaction is selected from PCR, 3SR, SDA, LAR/LCR, and LAMP.

6. The method as claimed in claim 2, wherein said exonuclease has an amino acid sequence selected from any one of SEQ ID NO:1 and SEQ ID NO:11.

7. The method of claim 2, wherein said sample is the product of a nucleic acid amplification reaction or the product of a reverse transcription reaction or a sample for sequence analysis.

8. The method of claim 1, wherein said sample is a sample of biological macromolecules.

9. The method of claim 1, wherein said sample comprises a nucleic acid, a protein, a carbohydrate polymer or a lipid.

10. The method of claim 1, wherein said sample comprises a double stranded nucleic acid, a DNA:RNA duplex of interest or a recombinantly produced protein.

11. The method of claim 2, wherein said sample is a sample of biological macromolecules.

12. The method of claim 2, wherein said sample comprises a nucleic acid, a protein, a carbohydrate polymer or a lipid.

13. The method of claim 6, wherein said sample comprises a double stranded nucleic acid, a DNA:RNA duplex of interest or a recombinantly produced protein.

14. The method of claim 7, wherein said nucleic acid amplification reaction is selected from PCR, 3SR, SDA, LAR/LCR, and LAMP.

* * * * *